US009140692B1

(12) United States Patent
Nudelman

(10) Patent No.: US 9,140,692 B1
(45) Date of Patent: Sep. 22, 2015

(54) METHODS OF IDENTIFYING GLYCOPEPTIDES RECOGNIZED BY DISEASE-ASSOCIATED AUTO-ANTIBODIES

(75) Inventor: Edward Nudelman, Beverly, MA (US)

(73) Assignee: Glycozym, Inc., Beverly, MA (US)

( * ) Notice: Subject to any disclaimer, the term of this patent is extended or adjusted under 35 U.S.C. 154(b) by 271 days.

(21) Appl. No.: 12/987,034

(22) Filed: Jan. 7, 2011

Related U.S. Application Data

(60) Provisional application No. 61/293,583, filed on Jan. 8, 2010, provisional application No. 61/294,477, filed on Jan. 12, 2010.

(51) Int. Cl.
*G01N 33/53* (2006.01)

(52) U.S. Cl.
CPC ...................................... *G01N 33/53* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,132,405 A | 7/1992 | Huston et al. | |
| 5,476,786 A | 12/1995 | Huston | |
| 5,876,716 A | 3/1999 | Hansen et al. | |
| 6,465,220 B1 | 10/2002 | Hassan et al. | |
| 7,332,279 B2 | 2/2008 | Clausen et al. | |
| 2013/0059744 A1* | 3/2013 | Wandall et al. | 506/9 |

FOREIGN PATENT DOCUMENTS

| | | | |
|---|---|---|---|
| WO | 89/12690 A1 | | 12/1989 |
| WO | WO0190197 | * | 11/2001 |
| WO | WO03099193 | * | 12/2003 |
| WO | WO2005015206 | * | 2/2005 |

OTHER PUBLICATIONS

Backlund et al., "Glycosylation of type II collagen is of major importance for T cell tolerance and pathology in collagen-induced arthritis", Eur J Immunol, 32:3776-3784 (2002).
Bennett et al., "cDNA cloning and expression of a novel human UDP-N-acetyl-alpha-D-galactosamine—Polypeptide N-acetylgalactosaminyltransferase, GalNAc-T3", Journal of Biological Chemistry, 271:17006-1701 (1996).
Bennett et al., "Cloning of a human UDP-N-acetyl-alpha-D-Galactosamine:polypeptide N-acetylgalactosaminyltransferase that complements other GalNAc-transferases in complete O-glycosylation of the MUC1 tandem repeat", J Biol Chem, 273:30472-30481 (1998).
Blixt et al., "Printed covalent glycan array for ligand profiling of diverse glycan binding proteins", Proc Natl Acad Sci., 101(49):17033-17038 (Nov. 24, 2004).
Brandlein et al., "CFR-1 receptor as target for tumor-specific apoptosis induced by the natural human monoclonal antibody PAM-1", Oncol Rep 11:777-784. (2004b).
Cote et al., "Generation of human monoclonal antibodies reactive with cellular antigens", Immunology: PNAS. USA., 80(7):2026-2030 (Apr. 1, 1983).
Danielczyk et al., "PankoMab: a potent new generation anti-tumour MUC1 antibody", Cancer Immunol Immunother, 55:1337-1347. (2006).
Dian et al., "Evaluation of a novel anti-mucin 1 (MUC1) antibody (PankoMab) as a potential diagnostic tool in human ductal breast cancer; comparison with two established antibodies", Onkologie, 32:238-244. (2009).
Gahring et al., "Granzyme B proteolysis of a neuronal glutamate receptor generates an autoantigen and is modulated by glycosylation", J Immunol, 166:1433-1438. (2001).
Hanisch et al., "Monoclonal-Antibody Bw835 Defines a Site-Specific Thomsen-Friedenreich Disaccharide Linked to Threonine Within the Vtsa Motif of Muc1 Tandem Repeats", Cancer Research, 55:4036-4040(1995).
Hellstrom et al., "Anti-mesothelin antibodies and circulating mesothelin relate to the clinical state in ovarian cancer patients", Cancer Epidemiol Biomarkers Prev, 17:1520-1526. (2008).
Iwai et al., "Molecular cloning and characterization of a novel UDP-GlcNAc:GalNAc-peptide beta1,3-N-acetylglucosaminyltransferase (beta 3Gn-T6), an enzyme synthesizing the core 3 structure of O-glycans", J Biol Chem, 277:12802-12809. (2002).
Julenius et al., "Prediction, conservation analysis, and structural characterization of mammalian mucin-type O-glycosylation sites", Glycobiology, 15:153-164. (2005).
Kawabata et al., "Antibody response against NY-ESO-1 in CHP-NY-ESO-1 vaccinated patients", Int J Cancer, 120:2178-2184. (2007).
Li et al., "Where do we place PankoMab in the reagents used to study the MUC1 superfamily?", Onkologie, 32:235-237 (2009).
Liu et al., "Proteomics-based identification of autoantibody against CDC25B as a novel serum marker in esophageal squamous cell carcinoma", Biochem Biophys Res Commun, 375:440-445. (2008).
Lu et al., "Humoral immunity directed against tumor-associated antigens as potential biomarkers for the early diagnosis of cancer", J Proteome Res, 7:1388-1394(2007).
Lubin et al., "Analysis of p53 antibodies in patients with various cancers define B-cell epitopes of human p53: distribution on primary structure and exposure on protein surface", Cancer Res, 53:5872-5876.(1993).
Pereira-Faca et al., "Identification of 14-3-3 theta as an antigen that induces a humoral response in lung cancer", Cancer Res, 67:12000-12006. (2007).

(Continued)

*Primary Examiner* — Laura B Goddard
(74) *Attorney, Agent, or Firm* — Ascenda Law Group, PC; Adda C. Gogoris

(57) ABSTRACT

Methods for identifying glycopeptides and more particularly glycopeptide epitopes that are specifically recognized by disease-associated auto-antibodies are provided. In some aspects the auto-antibodies are cancer-associated or autoimmune disease associated. In other aspects, methods of diagnosing a patient with cancer or an autoimmune disease, or for eliciting an immune response in a mammalian host directed to the glycopeptides of the invention are provided.

3 Claims, 8 Drawing Sheets

(56) References Cited

OTHER PUBLICATIONS

Rauschert et al., A new tumor-specific variant of GRP78 as target for antibody-based therapy, Lab Invest, 88:375-386 (2008).

Reis et al., Development and characterization of an antibody directed to an alpha-N-acetyl-D-galactosamine glycosylated MUC2 peptide, Glycoconj, J 15:51-62. (1998).

Sabbatini et al., Pilot study of a heptavalent vaccine-keyhole limpet hemocyanin conjugate plus QS21 in patients with epithelial ovarian, fallopian tube, or peritoneal cancer, Clin Cancer Res, 13:4170-4177. (2007).

Sahin et al., "Human neoplasms elicit multiple specific immune responses in the autologous host.", Immunology: PNAS USA, 92(23):11810-11813 (Dec. 5, 1995).

Snijdewint et al., Cellular and humoral immune responses to MUC1 mucin and tandem-repeat peptides in ovarian cancer patients and controls, Cancer Immunology Immunotherapy, 48:47-55 (1999).

Sorensen et al., Chemoenzymatically synthesized multimeric Tn/STn MUC1 glycopeptides elicit cancer-specific anti-MUC1 antibody responses and override tolerance. Glycobiology, 16:96-107 (2006).

Takeuchi et al., The epitope recognized by the unique anti-MUC1 monoclonal antibody MY.1E12 involves sialyl alpha 2-3galactosyl beta 1-3N-acetylgalactosaminide linked to a distinct threonine residue in the MUC1 tandem repeat, Journal of Immunological Methods, 270:199-209 (2002).

Tarp et al., Identification of a novel cancer-specific immunodominant glycopeptide epitope in the MUC1 tandem repeat, Glycobiology, 17:197-209. (2007).

Tarp et al., Mucin-type O-glycosylation and its potential use in drug and vaccine development, Biochim Biophys Acta, 1780:546-563 (2008).

White et al., Purification and cDNA cloning of a human UDP-N-acetyl-alpha-D-galactosamine:polypeptide N-acetylgalactosaminyltransferase. J Biol Chem 270:24156-24165. (1995).

* cited by examiner

FIG. 6A

FIG. 6B 893 (SEQ ID NO: 135)

931-C3 (SEQ ID NO: 146)

852-C3 (SEQ ID NO: 145)

SEQUENCE LISTING

```
<160> NUMBER OF SEQ ID NOS: 146

<210> SEQ ID NO 1
<211> LENGTH: 273
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
    50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
                85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
```

```
                115                 120                 125
Thr Ile Asn Val His Asp Val Glu Thr Gln Phe Asn Gln Tyr Lys Thr
            130                 135                 140
Glu Ala Ala Ser Arg Tyr Asn Leu Thr Ile Ser Asp Val Ser Val Ser
145                 150                 155                 160
Asp Val Pro Phe Pro Phe Ser Ala Gln Ser Gly Ala Gly Val Pro Gly
                165                 170                 175
Trp Gly Ile Ala Leu Leu Val Leu Val Cys Val Leu Val Ala Leu Ala
            180                 185                 190
Ile Val Tyr Leu Ile Ala Leu Ala Val Cys Gln Cys Arg Arg Lys Asn
                195                 200                 205
Tyr Gly Gln Leu Asp Ile Phe Pro Ala Arg Asp Thr Tyr His Pro Met
            210                 215                 220
Ser Glu Tyr Pro Thr Tyr His Thr His Gly Arg Tyr Val Pro Pro Ser
225                 230                 235                 240
Ser Thr Asp Arg Ser Pro Tyr Glu Lys Val Ser Ala Gly Asn Gly Gly
                245                 250                 255
Ser Ser Leu Ser Tyr Thr Asn Pro Ala Val Ala Ala Thr Ser Ala Asn
            260                 265                 270
Leu

<210> SEQ ID NO 2
<211> LENGTH: 264
<212> TYPE: PRT
<213> ORGANISM: Homo sapiens

<400> SEQUENCE: 2

Met Thr Pro Gly Thr Gln Ser Pro Phe Phe Leu Leu Leu Leu Leu Thr
1               5                   10                  15
Val Leu Thr Ala Thr Thr Ala Pro Lys Pro Ala Thr Val Val Thr Gly
            20                  25                  30
Ser Gly His Ala Ser Ser Thr Pro Gly Gly Glu Lys Glu Thr Ser Ala
        35                  40                  45
Thr Gln Arg Ser Ser Val Pro Ser Ser Thr Glu Lys Asn Ala Phe Asn
    50                  55                  60
Ser Ser Leu Glu Asp Pro Ser Thr Asp Tyr Tyr Gln Glu Leu Gln Arg
65                  70                  75                  80
Asp Ile Ser Glu Met Phe Leu Gln Ile Tyr Lys Gln Gly Gly Phe Leu
                85                  90                  95
Gly Leu Ser Asn Ile Lys Phe Arg Pro Gly Ser Val Val Val Gln Leu
            100                 105                 110
Thr Leu Ala Phe Arg Glu Gly Thr Ile Asn Val His Asp Val Glu Thr
        115                 120                 125
Gln Phe Asn Gln Tyr Lys Thr Glu Ala Ala Ser Arg Tyr Asn Leu Thr
    130                 135                 140
Ile Ser Asp Val Ser Val Ser Asp Val Pro Phe Pro Phe Ser Ala Gln
145                 150                 155                 160
Ser Gly Ala Gly Val Pro Gly Trp Gly Ile Ala Leu Leu Val Leu Val
                165                 170                 175
Cys Val Leu Val Ala Leu Ala Ile Val Tyr Leu Ile Ala Leu Ala Val
            180                 185                 190
Cys Gln Cys Arg Arg Lys Asn Tyr Gly Gln Leu Asp Ile Phe Pro Ala
        195                 200                 205
Arg Asp Thr Tyr His Pro Met Ser Glu Tyr Pro Thr Tyr His Thr His
```

```
                210               215               220
Gly Arg Tyr Val Pro Ser Ser Thr Asp Arg Ser Pro Tyr Glu Lys
225                 230               235               240

Val Ser Ala Gly Asn Gly Ser Ser Leu Ser Tyr Thr Asn Pro Ala
                245               250               255

Val Ala Ala Thr Ser Ala Asn Leu
                260
```

<210> SEQ ID NO 3
<211> LENGTH: 255
<212> TYPE: PRT
<213> ORGANISM: Homo sapiens

<400> SEQUENCE: 3

```
Met Thr Pro Gly Thr Gln Ser Pro Phe Phe Leu Leu Leu Leu Thr
1               5                 10                15

Val Leu Thr Val Val Thr Gly Ser Gly His Ala Ser Ser Thr Pro Gly
                20                25                30

Gly Glu Lys Glu Thr Ser Ala Thr Gln Arg Ser Ser Val Pro Ser Ser
                35                40                45

Thr Glu Lys Asn Ala Phe Asn Ser Ser Leu Glu Asp Pro Ser Thr Asp
50                55                60

Tyr Tyr Gln Glu Leu Gln Arg Asp Ile Ser Glu Met Phe Leu Gln Ile
65                70                75                80

Tyr Lys Gln Gly Gly Phe Leu Gly Leu Ser Asn Ile Lys Phe Arg Pro
                85                90                95

Gly Ser Val Val Val Gln Leu Thr Leu Ala Phe Arg Glu Gly Thr Ile
                100               105               110

Asn Val His Asp Val Glu Thr Gln Phe Asn Gln Tyr Lys Thr Glu Ala
                115               120               125

Ala Ser Arg Tyr Asn Leu Thr Ile Ser Asp Val Ser Val Ser Asp Val
                130               135               140

Pro Phe Pro Phe Ser Ala Gln Ser Gly Ala Gly Val Pro Gly Trp Gly
145               150               155               160

Ile Ala Leu Leu Val Leu Val Cys Val Leu Val Ala Leu Ala Ile Val
                165               170               175

Tyr Leu Ile Ala Leu Ala Val Cys Gln Cys Arg Arg Lys Asn Tyr Gly
                180               185               190

Gln Leu Asp Ile Phe Pro Ala Arg Asp Thr Tyr His Pro Met Ser Glu
                195               200               205

Tyr Pro Thr Tyr His Thr His Gly Arg Tyr Val Pro Pro Ser Ser Thr
                210               215               220

Asp Arg Ser Pro Tyr Glu Lys Val Ser Ala Gly Asn Gly Gly Ser Ser
225               230               235               240

Leu Ser Tyr Thr Asn Pro Ala Val Ala Ala Thr Ser Ala Asn Leu
                245               250               255
```

<210> SEQ ID NO 4
<211> LENGTH: 20
<212> TYPE: PRT
<213> ORGANISM: Artificial Sequence
<220> FEATURE:
<223> OTHER INFORMATION: Synthetic peptides

<400> SEQUENCE: 4

```
Thr Ser Ala Pro Asp Thr Arg Pro Ala Pro Gly Ser Thr Ala Pro Pro
1               5                 10                15
```

-continued

Ala His Gly Val
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptides

<400> SEQUENCE: 5

Ser Ala Pro Asp Thr Arg Pro Ala Pro Gly Ser Thr Ala Pro Pro Ala
1               5                   10                  15

His Gly Val Thr
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptides

<400> SEQUENCE: 6

Pro Gly Ser Thr Ala Pro Pro Ala His Gly Val Thr Ser Ala Pro Asp
1               5                   10                  15

Thr Arg Pro Ala
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptides

<400> SEQUENCE: 7

Gly Ser Thr Ala Pro Pro Ala His Gly Val Thr Ser Ala Pro Asp Thr
1               5                   10                  15

Arg Pro Ala Pro
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptides

<400> SEQUENCE: 8

Pro Pro Ala His Gly Val Thr Ser Ala Pro Asp Thr Arg Pro Ala Pro
1               5                   10                  15

Gly Ser Thr Ala
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptides

<400> SEQUENCE: 9

Phe Tyr Leu Ala Met Pro Phe Ala Thr Pro Met Glu Ala Glu Leu Ala

```
1               5                   10                  15

Arg Arg Ser Leu
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptides

<400> SEQUENCE: 10

Lys Phe Ser Glu Phe Trp Asp Leu Asp Pro Glu Val Arg Pro Thr Ser
1               5                   10                  15

Ala Val Ala Ala
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptides

<400> SEQUENCE: 11

Pro Leu Val Glu Gln Gly Arg Val Arg Ala Ala Thr Val Gly Ser Leu
1               5                   10                  15

Ala Gly Gln Pro
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptides

<400> SEQUENCE: 12

Leu Trp Ser Leu Cys Trp Ser Leu Ala Ile Ala Thr Pro Leu Pro Pro
1               5                   10                  15

Thr Ser Ala His
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptides

<400> SEQUENCE: 13

Leu Glu Ala Cys Val Ile Gln Gly Val Gly Val Thr Glu Thr Pro Leu
1               5                   10                  15

Met Lys Glu Asp
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic peptides

<400> SEQUENCE: 14
```

Lys Lys Trp Val Gln Asp Ser Met Lys Tyr Leu Asp Gln Lys Ser Pro
1               5                   10                  15

Thr Pro Lys Pro
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic peptides

<400> SEQUENCE: 15

Ser His His Ser Asp Glu Ser Asp Glu Leu Val Thr Asp Phe Pro Thr
1               5                   10                  15

Asp Leu Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic peptides

<400> SEQUENCE: 16

Asp Glu Ser Asp Glu Leu Val Thr Asp Phe Pro Thr Asp Leu Pro Ala
1               5                   10                  15

Thr Glu Val Phe
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic peptides

<400> SEQUENCE: 17

Phe Pro Thr Asp Phe Pro Thr Asp Leu Pro Ala Thr Glu Val Phe Thr
1               5                   10                  15

Pro Val Val Pro
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptides

<400> SEQUENCE: 18

Phe Pro Thr Asp Leu Pro Ala Thr Glu Val Phe Thr Pro Val Val Pro
1               5                   10                  15

Thr Val Asp Thr
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptides

<400> SEQUENCE: 19

```
Pro Ala Thr Glu Val Phe Thr Pro Val Val Pro Thr Val Asp Thr Tyr
1               5                   10                  15

Asp Gly Arg Gly
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic peptides

<400> SEQUENCE: 20

Pro Gly Ala Gln Gly Leu Pro Gly Val Gly Leu Thr Pro Ser Ala Ala
1               5                   10                  15

Gln Thr Ala Arg
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptides

<400> SEQUENCE: 21

Arg Gly Glu Thr Arg Cys Glu Gln Asp Arg Pro Ser Pro Thr Thr Ala
1               5                   10                  15

Pro Pro Ala Pro
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptides

<400> SEQUENCE: 22

Glu Thr Arg Cys Glu Gln Asp Arg Pro Ser Pro Thr Thr Ala Pro Pro
1               5                   10                  15

Ala Pro Pro Ser
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptides

<400> SEQUENCE: 23

Thr Arg Cys Glu Gln Asp Arg Pro Ser Pro Thr Thr Ala Pro Pro Ala
1               5                   10                  15

Pro Pro Ser Pro
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptides
```

```
<400> SEQUENCE: 24

Pro Ser Pro Thr Thr Ala Pro Pro Ala Pro Pro Ser Pro Ser Pro Ser
1               5                   10                  15

Pro Val Pro Lys
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic peptides

<400> SEQUENCE: 25

Pro Thr Thr Ala Pro Pro Ala Pro Pro Ser Pro Ser Pro Ser Pro Val
1               5                   10                  15

Pro Lys Ser Pro
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptides

<400> SEQUENCE: 26

Thr Ala Pro Pro Ala Pro Pro Ser Pro Ser Pro Ser Pro Val Pro Lys
1               5                   10                  15

Ser Pro Ser Val
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptides

<400> SEQUENCE: 27

Ser Thr Asn Glu Phe Leu Cys Asp Lys Asp Lys Thr Ser Thr Val Ala
1               5                   10                  15

Pro Thr Ile His
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptides

<400> SEQUENCE: 28

Asn Glu Phe Leu Cys Asp Lys Asp Lys Thr Ser Thr Val Ala Pro Thr
1               5                   10                  15

Ile His Thr Thr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptides
```

<400> SEQUENCE: 29

Cys Asp Lys Asp Lys Thr Ser Thr Val Ala Pro Thr Ile His Thr Thr
1               5                   10                  15

Val Pro Ser Pro
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic peptides

<400> SEQUENCE: 30

Asp Lys Thr Ser Thr Val Ala Pro Thr Ile His Thr Thr Val Pro Ser
1               5                   10                  15

Pro Thr Thr Thr
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic peptides

<400> SEQUENCE: 31

Lys Thr Ser Thr Val Ala Pro Thr Ile His Thr Thr Val Pro Ser Pro
1               5                   10                  15

Thr Thr Thr Pro
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic peptides

<400> SEQUENCE: 32

Thr Val Ala Pro Thr Ile His Thr Thr Val Pro Ser Pro Thr Thr Thr
1               5                   10                  15

Pro Thr Pro Lys
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic peptides

<400> SEQUENCE: 33

Ala Pro Thr Ile His Thr Thr Val Pro Ser Pro Thr Thr Thr Pro Thr
1               5                   10                  15

Pro Lys Glu Lys
            20

<210> SEQ ID NO 34
<211> LENGTH: 20
<212> TYPE: PRT
<213> ORGANISM: Artificial Sequence
<220> FEATURE:

<223> OTHER INFORMATION: Synthetic peptides

<400> SEQUENCE: 34

Pro Thr Ile His Thr Thr Val Pro Ser Pro Thr Thr Pro Thr Pro
1               5                   10                  15

Lys Glu Lys Pro
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic peptides

<400> SEQUENCE: 35

Thr Ile His Thr Thr Val Pro Ser Pro Thr Thr Thr Pro Thr Pro Lys
1               5                   10                  15

Glu Lys Pro Glu
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic peptides

<400> SEQUENCE: 36

Thr Pro Thr Pro Lys Glu Lys Pro Glu Ala Gly Thr Tyr Ser Val Asn
1               5                   10                  15

Asn Gly Asn Asp
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic peptides

<400> SEQUENCE: 37

Ala Cys Leu Ala Val Ser Ala Gly Pro Val Pro Thr Pro Pro Asp Asn
1               5                   10                  15

Ile Gln Val Gln
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptides

<400> SEQUENCE: 38

Arg Arg Ala Val Leu Pro Gln Glu Glu Glu Gly Ser Gly Gly Gly Gln
1               5                   10                  15

Leu Val Thr Glu
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic peptides

<400> SEQUENCE: 39

Leu Asn Ala Val Asn Asn Ser Leu Thr Pro Gln Ser Thr Lys Val Pro
1               5                   10                  15

Ser Leu Phe Glu
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic peptides

<400> SEQUENCE: 40

Asn Ala Val Asn Asn Ser Leu Thr Pro Gln Ser Thr Lys Val Pro Ser
1               5                   10                  15

Leu Phe Glu Phe
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic peptides

<400> SEQUENCE: 41

Thr Phe Val Leu Ser Ala Leu Gln Pro Ser Pro Thr His Ser Ser Ser
1               5                   10                  15

Asn Thr Gln Arg
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptides

<400> SEQUENCE: 42

Arg Gln Gly Trp Ala Leu Arg Pro Val Leu Pro Thr Gln Ser Ala His
1               5                   10                  15

Asp Pro Pro Ala
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic peptides

<400> SEQUENCE: 43

Gln Lys Lys Ala Lys Asn Leu Asp Ala Ile Thr Thr Pro Asp Pro Thr
1               5                   10                  15

Thr Asn Ala Ser
            20

<210> SEQ ID NO 44
<211> LENGTH: 20
<212> TYPE: PRT

<213> ORGANISM: Artificial Sequence
<220> FEATURE:
<223> OTHER INFORMATION: Synthetic peptides

<400> SEQUENCE: 44

Phe Leu Ser Leu Ser Gln Gly Gln Glu Ser Gln Thr Glu Leu Pro Asn
1               5                   10                  15

Pro Arg Ile Ser
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic peptides

<400> SEQUENCE: 45

Leu Ser Leu Ala Leu Val Thr Asn Ser Ala Pro Thr Ser Ser Ser Thr
1               5                   10                  15

Lys Lys Thr Gln
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic peptides

<400> SEQUENCE: 46

Leu Ile Ser Pro Leu Ala Gln Ala Val Arg Ser Ser Arg Thr Pro
1               5                   10                  15

Ser Asp Lys Pro
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic peptides

<400> SEQUENCE: 47

Asp Asp Glu Asn Thr Ala Gln Phe Val His Val Ser Glu Ser Phe Pro
1               5                   10                  15

His Pro Gly Phe
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic peptides

<400> SEQUENCE: 48

Ser Glu Ser Phe Pro His Pro Gly Phe Asn Met Ser Leu Leu Glu Asn
1               5                   10                  15

His Thr Arg Gln
            20

<210> SEQ ID NO 49
<211> LENGTH: 20

```
<212> TYPE: PRT
<213> ORGANISM: Artificial Sequence
<220> FEATURE:
<223> OTHER INFORMATION: Synthetic peptides

<400> SEQUENCE: 49

Ser Gly Trp Gly Ser Ile Glu Pro Glu Asn Phe Ser Phe Pro Asp Asp
1               5                   10                  15

Leu Gln Cys Val
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic peptides

<400> SEQUENCE: 50

Arg Ile Gln Arg Gly Pro Gly Arg Ala Phe Val Thr Ile Gly Lys Ile
1               5                   10                  15

Gly Asn Met Arg
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic peptides

<400> SEQUENCE: 51

Glu Met Ser Arg His Ser Leu Glu Gln Lys Pro Thr Asp Ala Pro Pro
1               5                   10                  15

Lys Val Leu Thr
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptides

<400> SEQUENCE: 52

Cys Ser Glu Ser Leu Glu Leu Glu Asp Pro Ser Ser Gly Leu Gly Val
1               5                   10                  15

Thr Lys Gln Asp
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic peptides

<400> SEQUENCE: 53

Leu Leu Glu Phe Tyr Leu Ala Met Pro Phe Ala Thr Pro Met Glu Ala
1               5                   10                  15

Glu Leu Ala Arg
            20

<210> SEQ ID NO 54
```

```
<211> LENGTH: 203
<212> TYPE: PRT
<213> ORGANISM: Homo sapiens

<400> SEQUENCE: 54

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Ile Pro Ala Pro Thr Thr Thr Lys Ser Cys Arg
50                  55                  60

Glu Thr Phe Leu Lys Cys Phe Cys Arg Phe Ile Asn Lys Gly Val Phe
65                  70                  75                  80

Trp Ala Ser Pro Ile Leu Ser Ser Val Ser Asp Val Pro Phe Pro Phe
                85                  90                  95

Ser Ala Gln Ser Gly Ala Gly Val Pro Gly Trp Gly Ile Ala Leu Leu
            100                 105                 110

Val Leu Val Cys Val Leu Val Ala Leu Ala Ile Val Tyr Leu Ile Ala
        115                 120                 125

Leu Ala Val Cys Gln Cys Arg Arg Lys Asn Tyr Gly Gln Leu Asp Ile
130                 135                 140

Phe Pro Ala Arg Asp Thr Tyr His Pro Met Ser Glu Tyr Pro Thr Tyr
145                 150                 155                 160

His Thr His Gly Arg Tyr Val Pro Pro Ser Thr Asp Arg Ser Pro Tyr
                165                 170                 175

Glu Lys Val Ser Ala Gly Asn Gly Gly Ser Ser Leu Ser Tyr Thr Asn
            180                 185                 190

Pro Ala Val Ala Ala Thr Ser Ala Asn Leu
        195                 200

<210> SEQ ID NO 55
<211> LENGTH: 150
<212> TYPE: PRT
<213> ORGANISM: Homo sapiens

<400> SEQUENCE: 55

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Phe Asn Ser Ser Leu Glu Asp Pro Ser Thr Asp
50                  55                  60

Tyr Tyr Gln Glu Leu Gln Arg Asp Ile Ser Glu Met Ala Val Cys Gln
65                  70                  75                  80

Cys Arg Arg Lys Asn Tyr Gly Gln Leu Asp Ile Phe Pro Ala Arg Asp
                85                  90                  95

Thr Tyr His Pro Met Ser Glu Tyr Pro Thr Tyr His Thr His Gly Arg
            100                 105                 110

Tyr Val Pro Pro Ser Ser Thr Asp Arg Ser Pro Tyr Glu Lys Val Ser
        115                 120                 125

Ala Gly Asn Gly Gly Ser Ser Leu Ser Tyr Thr Asn Pro Ala Val Ala
130                 135                 140
```

```
Ala Thr Ser Ala Asn Leu
145                 150

<210> SEQ ID NO 56
<211> LENGTH: 159
<212> TYPE: PRT
<213> ORGANISM: Homo sapiens

<400> SEQUENCE: 56

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Ala Val Cys Gln Cys Arg Arg Lys Asn Tyr Gly
                85                  90                  95

Gln Leu Asp Ile Phe Pro Ala Arg Asp Thr Tyr His Pro Met Ser Glu
            100                 105                 110

Tyr Pro Thr Tyr His Thr His Gly Arg Tyr Val Pro Pro Ser Ser Thr
        115                 120                 125

Asp Arg Ser Pro Tyr Glu Lys Val Ser Ala Gly Asn Gly Gly Ser Ser
    130                 135                 140

Leu Ser Tyr Thr Asn Pro Ala Val Ala Ala Thr Ser Ala Asn Leu
145                 150                 155

<210> SEQ ID NO 57
<211> LENGTH: 14507
<212> TYPE: PRT
<213> ORGANISM: Homo sapiens

<400> SEQUENCE: 57

Met Leu Lys Pro Ser Gly Leu Pro Gly Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
    130                 135                 140

Ser Thr Tyr Thr Leu Thr Val Glu Thr Ser Gly Pro Val Thr Glu
145                 150                 155                 160
```

-continued

Lys Tyr Thr Val Pro Thr Glu Thr Ser Thr Thr Gly Asp Ser Thr
                165                 170                 175

Glu Thr Pro Trp Asp Thr Arg Tyr Ile Pro Val Lys Ile Thr Ser Pro
                180                 185                 190

Met Lys Thr Phe Ala Asp Ser Thr Ala Ser Lys Glu Asn Ala Pro Val
                195                 200                 205

Ser Met Thr Pro Ala Glu Thr Thr Val Thr Asp Ser His Thr Pro Gly
            210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
                260                 265                 270

Ala Gly His Ser Arg Ile Ser Thr Ser Ala Pro Leu Ser Ser Ser Ala
            275                 280                 285

Ser Val Leu Asp Asn Lys Ile Ser Glu Thr Ser Ile Phe Ser Gly Gln
            290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
                340                 345                 350

Pro Ser Ile Ser Thr Lys Gln Thr Ala Glu Thr Ile Leu Thr Phe His
                355                 360                 365

Ala Phe Ala Glu Thr Met Asp Ile Pro Ser Thr His Ile Ala Lys Thr
            370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
                420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
            530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

-continued

```
Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
        595                 600                 605

Ile Ser Met Thr Gly Gly Ser Ser Thr Arg Gly Ser Gln Gly Thr Thr
    610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
        675                 680                 685

Ala Phe Arg Glu Gly Thr Ser Leu Gly Leu Thr Pro Leu Asn Thr Arg
    690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
        755                 760                 765

Val Leu Ser Ser Met Thr Leu Ser Asn Ala Ala Thr Ser Pro Glu Arg
    770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
        835                 840                 845

Thr Phe Ser Ser Ser Thr Pro Ser Thr His Leu Phe Thr Ser Gly Glu
    850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
        915                 920                 925

Thr Asn Ser Thr Gly Ser Ala Leu Pro Lys Ile Ser His Leu Thr Gly
    930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Thr Val Ser Thr Ser Ala Thr Ser Leu
            980                 985                 990

Ser Ala Thr Val Met Val Ser Lys  Phe Thr Ser Pro Ala  Thr Ser Ser
```

-continued

```
            995                 1000                1005
Met Glu Ala Thr Ser Ile Arg Glu Pro Ser Thr Thr Ile Leu Thr
    1010                1015                1020

Thr Glu Thr Thr Asn Gly Pro Gly Ser Met Ala Val Ala Ser Thr
    1025                1030                1035

Asn Ile Pro Ile Gly Lys Gly Tyr Ile Thr Glu Gly Arg Leu Asp
    1040                1045                1050

Thr Ser His Leu Pro Ile Gly Thr Thr Ala Ser Ser Glu Thr Ser
    1055                1060                1065

Met Asp Phe Thr Met Ala Lys Glu Ser Val Ser Met Ser Val Ser
    1070                1075                1080

Pro Ser Gln Ser Met Asp Ala Ala Gly Ser Ser Thr Pro Gly Arg
    1085                1090                1095

Thr Ser Gln Phe Val Asp Thr Phe Ser Asp Asp Val Tyr His Leu
    1100                1105                1110

Thr Ser Arg Glu Ile Thr Ile Pro Arg Asp Gly Thr Ser Ser Ala
    1115                1120                1125

Leu Thr Pro Gln Met Thr Ala Thr His Pro Pro Ser Pro Asp Pro
    1130                1135                1140

Gly Ser Ala Arg Ser Thr Trp Leu Gly Ile Leu Ser Ser Ser Pro
    1145                1150                1155

Ser Ser Pro Thr Pro Lys Val Thr Met Ser Ser Thr Phe Ser Thr
    1160                1165                1170

Gln Arg Val Thr Thr Ser Met Ile Met Asp Thr Val Glu Thr Ser
    1175                1180                1185

Arg Trp Asn Met Pro Asn Leu Pro Ser Thr Thr Ser Leu Thr Pro
    1190                1195                1200

Ser Asn Ile Pro Thr Ser Gly Ala Ile Gly Lys Ser Thr Leu Val
    1205                1210                1215

Pro Leu Asp Thr Pro Ser Pro Ala Thr Ser Leu Glu Ala Ser Glu
    1220                1225                1230

Gly Gly Leu Pro Thr Leu Ser Thr Tyr Pro Glu Ser Thr Asn Thr
    1235                1240                1245

Pro Ser Ile His Leu Gly Ala His Ala Ser Ser Glu Ser Pro Ser
    1250                1255                1260

Thr Ile Lys Leu Thr Met Ala Ser Val Val Lys Pro Gly Ser Tyr
    1265                1270                1275

Thr Pro Leu Thr Phe Pro Ser Ile Glu Thr His Ile His Val Ser
    1280                1285                1290

Thr Ala Arg Met Ala Tyr Ser Ser Gly Ser Ser Pro Glu Met Thr
    1295                1300                1305

Ala Pro Gly Glu Thr Asn Thr Gly Ser Thr Trp Asp Pro Thr Thr
    1310                1315                1320

Tyr Ile Thr Thr Thr Asp Pro Lys Asp Thr Ser Ser Ala Gln Val
    1325                1330                1335

Ser Thr Pro His Ser Val Arg Thr Leu Arg Thr Thr Glu Asn His
    1340                1345                1350

Pro Lys Thr Glu Ser Ala Thr Pro Ala Ala Tyr Ser Gly Ser Pro
    1355                1360                1365

Lys Ile Ser Ser Ser Pro Asn Leu Thr Ser Pro Ala Thr Lys Ala
    1370                1375                1380

Trp Thr Ile Thr Asp Thr Thr Glu His Ser Thr Gln Leu His Tyr
    1385                1390                1395
```

```
Thr Lys Leu Ala Glu Lys Ser Ser Gly Phe Glu Thr Gln Ser Ala
    1400            1405            1410

Pro Gly Pro Val Ser Val Val Ile Pro Thr Ser Pro Thr Ile Gly
    1415            1420            1425

Ser Ser Thr Leu Glu Leu Thr Ser Asp Val Pro Gly Glu Pro Leu
    1430            1435            1440

Val Leu Ala Pro Ser Glu Gln Thr Thr Ile Thr Leu Pro Met Ala
    1445            1450            1455

Thr Trp Leu Ser Thr Ser Leu Thr Glu Glu Met Ala Ser Thr Asp
    1460            1465            1470

Leu Asp Ile Ser Ser Pro Ser Ser Pro Met Ser Thr Phe Ala Ile
    1475            1480            1485

Phe Pro Pro Met Ser Thr Pro Ser His Glu Leu Ser Lys Ser Glu
    1490            1495            1500

Ala Asp Thr Ser Ala Ile Arg Asn Thr Asp Ser Thr Thr Leu Asp
    1505            1510            1515

Gln His Leu Gly Ile Arg Ser Leu Gly Arg Thr Gly Asp Leu Thr
    1520            1525            1530

Thr Val Pro Ile Thr Pro Leu Thr Thr Thr Trp Thr Ser Val Ile
    1535            1540            1545

Glu His Ser Thr Gln Ala Gln Asp Thr Leu Ser Ala Thr Met Ser
    1550            1555            1560

Pro Thr His Val Thr Gln Ser Leu Lys Asp Gln Thr Ser Ile Pro
    1565            1570            1575

Ala Ser Ala Ser Pro Ser His Leu Thr Glu Val Tyr Pro Glu Leu
    1580            1585            1590

Gly Thr Gln Gly Arg Ser Ser Ser Glu Ala Thr Thr Phe Trp Lys
    1595            1600            1605

Pro Ser Thr Asp Thr Leu Ser Arg Glu Ile Glu Thr Gly Pro Thr
    1610            1615            1620

Asn Ile Gln Ser Thr Pro Pro Met Asp Asn Thr Thr Thr Gly Ser
    1625            1630            1635

Ser Ser Ser Gly Val Thr Leu Gly Ile Ala His Leu Pro Ile Gly
    1640            1645            1650

Thr Ser Ser Pro Ala Glu Thr Ser Thr Asn Met Ala Leu Glu Arg
    1655            1660            1665

Arg Ser Ser Thr Ala Thr Val Ser Met Ala Gly Thr Met Gly Leu
    1670            1675            1680

Leu Val Thr Ser Ala Pro Gly Arg Ser Ile Ser Gln Ser Leu Gly
    1685            1690            1695

Arg Val Ser Ser Val Leu Ser Glu Ser Thr Thr Glu Gly Val Thr
    1700            1705            1710

Asp Ser Ser Lys Gly Ser Ser Pro Arg Leu Asn Thr Gln Gly Asn
    1715            1720            1725

Thr Ala Leu Ser Ser Ser Leu Glu Pro Ser Tyr Ala Glu Gly Ser
    1730            1735            1740

Gln Met Ser Thr Ser Ile Pro Leu Thr Ser Ser Pro Thr Thr Pro
    1745            1750            1755

Asp Val Glu Phe Ile Gly Gly Ser Thr Phe Trp Thr Lys Glu Val
    1760            1765            1770

Thr Thr Val Met Thr Ser Asp Ile Ser Lys Ser Ser Ala Arg Thr
    1775            1780            1785
```

-continued

```
Glu Ser Ser Ser Ala Thr Leu Met Ser Thr Ala Leu Gly Ser Thr
1790                1795                1800

Glu Asn Thr Gly Lys Glu Lys Leu Arg Thr Ala Ser Met Asp Leu
1805                1810                1815

Pro Ser Pro Thr Pro Ser Met Glu Val Thr Pro Trp Ile Ser Leu
1820                1825                1830

Thr Leu Ser Asn Ala Pro Asn Thr Thr Asp Ser Leu Asp Leu Ser
1835                1840                1845

His Gly Val His Thr Ser Ser Ala Gly Thr Leu Ala Thr Asp Arg
1850                1855                1860

Ser Leu Asn Thr Gly Val Thr Arg Ala Ser Arg Leu Glu Asn Gly
1865                1870                1875

Ser Asp Thr Ser Ser Lys Ser Leu Ser Met Gly Asn Ser Thr His
1880                1885                1890

Thr Ser Met Thr Tyr Thr Glu Lys Ser Glu Val Ser Ser Ser Ile
1895                1900                1905

His Pro Arg Pro Glu Thr Ser Ala Pro Gly Ala Glu Thr Thr Leu
1910                1915                1920

Thr Ser Thr Pro Gly Asn Arg Ala Ile Ser Leu Thr Leu Pro Phe
1925                1930                1935

Ser Ser Ile Pro Val Glu Glu Val Ile Ser Thr Gly Ile Thr Ser
1940                1945                1950

Gly Pro Asp Ile Asn Ser Ala Pro Met Thr His Ser Pro Ile Thr
1955                1960                1965

Pro Pro Thr Ile Val Trp Thr Ser Thr Gly Thr Ile Glu Gln Ser
1970                1975                1980

Thr Gln Pro Leu His Ala Val Ser Ser Glu Lys Val Ser Val Gln
1985                1990                1995

Thr Gln Ser Thr Pro Tyr Val Asn Ser Val Ala Val Ser Ala Ser
2000                2005                2010

Pro Thr His Glu Asn Ser Val Ser Ser Gly Ser Ser Thr Ser Ser
2015                2020                2025

Pro Tyr Ser Ser Ala Ser Leu Glu Ser Leu Asp Ser Thr Ile Ser
2030                2035                2040

Arg Arg Asn Ala Ile Thr Ser Trp Leu Trp Asp Leu Thr Thr Ser
2045                2050                2055

Leu Pro Thr Thr Thr Trp Pro Ser Thr Ser Leu Ser Glu Ala Leu
2060                2065                2070

Ser Ser Gly His Ser Gly Val Ser Asn Pro Ser Ser Thr Thr Thr
2075                2080                2085

Glu Phe Pro Leu Phe Ser Ala Ala Ser Thr Ser Ala Ala Lys Gln
2090                2095                2100

Arg Asn Pro Glu Thr Glu Thr His Gly Pro Gln Asn Thr Ala Ala
2105                2110                2115

Ser Thr Leu Asn Thr Asp Ala Ser Ser Val Thr Gly Leu Ser Glu
2120                2125                2130

Thr Pro Val Gly Ala Ser Ile Ser Ser Glu Val Pro Leu Pro Met
2135                2140                2145

Ala Ile Thr Ser Arg Ser Asp Val Ser Gly Leu Thr Ser Glu Ser
2150                2155                2160

Thr Ala Asn Pro Ser Leu Gly Thr Ala Ser Ser Ala Gly Thr Lys
2165                2170                2175

Leu Thr Arg Thr Ile Ser Leu Pro Thr Ser Glu Ser Leu Val Ser
```

```
            2180                2185                2190

Phe Arg Met Asn Lys Asp Pro Trp Thr Val Ser Ile Pro Leu Gly
    2195                2200                2205

Ser His Pro Thr Thr Asn Thr Glu Thr Ser Ile Pro Val Asn Ser
    2210                2215                2220

Ala Gly Pro Pro Gly Leu Ser Thr Val Ala Ser Asp Val Ile Asp
    2225                2230                2235

Thr Pro Ser Asp Gly Ala Glu Ser Ile Pro Thr Val Ser Phe Ser
    2240                2245                2250

Pro Ser Pro Asp Thr Glu Val Thr Thr Ile Ser His Phe Pro Glu
    2255                2260                2265

Lys Thr Thr His Ser Phe Arg Thr Ile Ser Ser Leu Thr His Glu
    2270                2275                2280

Leu Thr Ser Arg Val Thr Pro Ile Pro Gly Asp Trp Met Ser Ser
    2285                2290                2295

Ala Met Ser Thr Lys Pro Thr Gly Ala Ser Pro Ser Ile Thr Leu
    2300                2305                2310

Gly Glu Arg Arg Thr Ile Thr Ser Ala Ala Pro Thr Thr Ser Pro
    2315                2320                2325

Ile Val Leu Thr Ala Ser Phe Thr Glu Thr Ser Thr Val Ser Leu
    2330                2335                2340

Asp Asn Glu Thr Thr Val Lys Thr Ser Asp Ile Leu Asp Ala Arg
    2345                2350                2355

Lys Thr Asn Glu Leu Pro Ser Asp Ser Ser Ser Ser Asp Leu
    2360                2365                2370

Ile Asn Thr Ser Ile Ala Ser Ser Thr Met Asp Val Thr Lys Thr
    2375                2380                2385

Ala Ser Ile Ser Pro Thr Ser Ile Ser Gly Met Thr Ala Ser Ser
    2390                2395                2400

Ser Pro Ser Leu Phe Ser Ser Asp Arg Pro Gln Val Pro Thr Ser
    2405                2410                2415

Thr Thr Glu Thr Asn Thr Ala Thr Ser Pro Ser Val Ser Ser Asn
    2420                2425                2430

Thr Tyr Ser Leu Asp Gly Gly Ser Asn Val Gly Gly Thr Pro Ser
    2435                2440                2445

Thr Leu Pro Pro Phe Thr Ile Thr His Pro Val Glu Thr Ser Ser
    2450                2455                2460

Ala Leu Leu Ala Trp Ser Arg Pro Val Arg Thr Phe Ser Thr Met
    2465                2470                2475

Val Ser Thr Asp Thr Ala Ser Gly Glu Asn Pro Thr Ser Ser Asn
    2480                2485                2490

Ser Val Val Thr Ser Val Pro Ala Pro Gly Thr Trp Thr Ser Val
    2495                2500                2505

Gly Ser Thr Thr Asp Leu Pro Ala Met Gly Phe Leu Lys Thr Ser
    2510                2515                2520

Pro Ala Gly Glu Ala His Ser Leu Leu Ala Ser Thr Ile Glu Pro
    2525                2530                2535

Ala Thr Ala Phe Thr Pro His Leu Ser Ala Ala Val Val Thr Gly
    2540                2545                2550

Ser Ser Ala Thr Ser Glu Ala Ser Leu Leu Thr Thr Ser Glu Ser
    2555                2560                2565

Lys Ala Ile His Ser Ser Pro Gln Thr Pro Thr Thr Pro Thr Ser
    2570                2575                2580
```

```
Gly Ala Asn Trp Glu Thr Ser Ala Thr Pro Glu Ser Leu Leu Val
         2585            2590            2595

Val Thr Glu Thr Ser Asp Thr Thr Leu Thr Ser Lys Ile Leu Val
    2600            2605            2610

Thr Asp Thr Ile Leu Phe Ser Thr Val Ser Thr Pro Pro Ser Lys
    2615            2620            2625

Phe Pro Ser Thr Gly Thr Leu Ser Gly Ala Ser Phe Pro Thr Leu
    2630            2635            2640

Leu Pro Asp Thr Pro Ala Ile Pro Leu Thr Ala Thr Glu Pro Thr
    2645            2650            2655

Ser Ser Leu Ala Thr Ser Phe Asp Ser Thr Pro Leu Val Thr Ile
    2660            2665            2670

Ala Ser Asp Ser Leu Gly Thr Val Pro Glu Thr Thr Leu Thr Met
    2675            2680            2685

Ser Glu Thr Ser Asn Gly Asp Ala Leu Val Leu Lys Thr Val Ser
    2690            2695            2700

Asn Pro Asp Arg Ser Ile Pro Gly Ile Thr Ile Gln Gly Val Thr
    2705            2710            2715

Glu Ser Pro Leu His Pro Ser Ser Thr Ser Pro Ser Lys Ile Val
    2720            2725            2730

Ala Pro Arg Asn Thr Thr Tyr Glu Gly Ser Ile Thr Val Ala Leu
    2735            2740            2745

Ser Thr Leu Pro Ala Gly Thr Thr Gly Ser Leu Val Phe Ser Gln
    2750            2755            2760

Ser Ser Glu Asn Ser Glu Thr Thr Ala Leu Val Asp Ser Ser Ala
    2765            2770            2775

Gly Leu Glu Arg Ala Ser Val Met Pro Leu Thr Thr Gly Ser Gln
    2780            2785            2790

Gly Met Ala Ser Ser Gly Gly Ile Arg Ser Gly Ser Thr His Ser
    2795            2800            2805

Thr Gly Thr Lys Thr Phe Ser Ser Leu Pro Leu Thr Met Asn Pro
    2810            2815            2820

Gly Glu Val Thr Ala Met Ser Glu Ile Thr Thr Asn Arg Leu Thr
    2825            2830            2835

Ala Thr Gln Ser Thr Ala Pro Lys Gly Ile Pro Val Lys Pro Thr
    2840            2845            2850

Ser Ala Glu Ser Gly Leu Leu Thr Pro Val Ser Ala Ser Ser Ser
    2855            2860            2865

Pro Ser Lys Ala Phe Ala Ser Leu Thr Thr Ala Pro Pro Thr Trp
    2870            2875            2880

Gly Ile Pro Gln Ser Thr Leu Thr Phe Glu Phe Ser Glu Val Pro
    2885            2890            2895

Ser Leu Asp Thr Lys Ser Ala Ser Leu Pro Thr Pro Gly Gln Ser
    2900            2905            2910

Leu Asn Thr Ile Pro Asp Ser Asp Ala Ser Thr Ala Ser Ser Ser
    2915            2920            2925

Leu Ser Lys Ser Pro Glu Lys Asn Pro Arg Ala Arg Met Met Thr
    2930            2935            2940

Ser Thr Lys Ala Ile Ser Ala Ser Ser Phe Gln Ser Thr Gly Phe
    2945            2950            2955

Thr Glu Thr Pro Glu Gly Ser Ala Ser Pro Ser Met Ala Gly His
    2960            2965            2970
```

-continued

| | | | | | | | | | | | | | |
|---|---|---|---|---|---|---|---|---|---|---|---|---|---|
|Glu|Pro|Arg|Val|Pro|Thr|Ser|Gly|Thr|Gly|Asp|Pro|Arg|Tyr|Ala|
|2975| | | | |2980| | | | |2985| | | |

Ser Glu Ser Met Ser Tyr Pro Asp Pro Ser Lys Ala Ser Ser Ala
2990          2995              3000

Met Thr Ser Thr Ser Leu Ala Ser Lys Leu Thr Thr Leu Phe Ser
3005          3010              3015

Thr Gly Gln Ala Ala Arg Ser Gly Ser Ser Ser Ser Pro Ile Ser
3020          3025              3030

Leu Ser Thr Glu Lys Glu Thr Ser Phe Leu Ser Pro Thr Ala Ser
3035          3040              3045

Thr Ser Arg Lys Thr Ser Leu Phe Leu Gly Pro Ser Met Ala Arg
3050          3055              3060

Gln Pro Asn Ile Leu Val His Leu Gln Thr Ser Ala Leu Thr Leu
3065          3070              3075

Ser Pro Thr Ser Thr Leu Asn Met Ser Gln Glu Glu Pro Pro Glu
3080          3085              3090

Leu Thr Ser Ser Gln Thr Ile Ala Glu Glu Glu Gly Thr Thr Ala
3095          3100              3105

Glu Thr Gln Thr Leu Thr Phe Thr Pro Ser Glu Thr Pro Thr Ser
3110          3115              3120

Leu Leu Pro Val Ser Ser Pro Thr Glu Pro Thr Ala Arg Arg Lys
3125          3130              3135

Ser Ser Pro Glu Thr Trp Ala Ser Ser Ile Ser Val Pro Ala Lys
3140          3145              3150

Thr Ser Leu Val Glu Thr Thr Asp Gly Thr Leu Val Thr Thr Ile
3155          3160              3165

Lys Met Ser Ser Gln Ala Ala Gln Gly Asn Ser Thr Trp Pro Ala
3170          3175              3180

Pro Ala Glu Glu Thr Gly Ser Ser Pro Ala Gly Thr Ser Pro Gly
3185          3190              3195

Ser Pro Glu Met Ser Thr Thr Leu Lys Ile Met Ser Ser Lys Glu
3200          3205              3210

Pro Ser Ile Ser Pro Glu Ile Arg Ser Thr Val Arg Asn Ser Pro
3215          3220              3225

Trp Lys Thr Pro Glu Thr Thr Val Pro Met Glu Thr Thr Val Glu
3230          3235              3240

Pro Val Thr Leu Gln Ser Thr Ala Leu Gly Ser Gly Ser Thr Ser
3245          3250              3255

Ile Ser His Leu Pro Thr Gly Thr Thr Ser Pro Thr Lys Ser Pro
3260          3265              3270

Thr Glu Asn Met Leu Ala Thr Glu Arg Val Ser Leu Ser Pro Ser
3275          3280              3285

Pro Pro Glu Ala Trp Thr Asn Leu Tyr Ser Gly Thr Pro Gly Gly
3290          3295              3300

Thr Arg Gln Ser Leu Ala Thr Met Ser Ser Val Ser Leu Glu Ser
3305          3310              3315

Pro Thr Ala Arg Ser Ile Thr Gly Thr Gly Gln Gln Ser Ser Pro
3320          3325              3330

Glu Leu Val Ser Lys Thr Thr Gly Met Glu Phe Ser Met Trp His
3335          3340              3345

Gly Ser Thr Gly Gly Thr Thr Gly Asp Thr His Val Ser Leu Ser
3350          3355              3360

Thr Ser Ser Asn Ile Leu Glu Asp Pro Val Thr Ser Pro Asn Ser

-continued

```
              3365                3370                3375
Val Ser Ser Leu Thr Asp Lys Ser Lys His Lys Thr Glu Thr Trp
    3380                3385                3390
Val Ser Thr Thr Ala Ile Pro Ser Thr Val Leu Asn Asn Lys Ile
    3395                3400                3405
Met Ala Ala Glu Gln Gln Thr Ser Arg Ser Val Asp Glu Ala Tyr
    3410                3415                3420
Ser Ser Thr Ser Ser Trp Ser Asp Gln Thr Ser Gly Ser Asp Ile
    3425                3430                3435
Thr Leu Gly Ala Ser Pro Asp Val Thr Asn Thr Leu Tyr Ile Thr
    3440                3445                3450
Ser Thr Ala Gln Thr Thr Ser Leu Val Ser Leu Pro Ser Gly Asp
    3455                3460                3465
Gln Gly Ile Thr Ser Leu Thr Asn Pro Ser Gly Gly Lys Thr Ser
    3470                3475                3480
Ser Ala Ser Ser Val Thr Ser Pro Ser Ile Gly Leu Glu Thr Leu
    3485                3490                3495
Arg Ala Asn Val Ser Ala Val Lys Ser Asp Ile Ala Pro Thr Ala
    3500                3505                3510
Gly His Leu Ser Gln Thr Ser Ser Pro Ala Glu Val Ser Ile Leu
    3515                3520                3525
Asp Val Thr Thr Ala Pro Thr Pro Gly Ile Ser Thr Thr Ile Thr
    3530                3535                3540
Thr Met Gly Thr Asn Ser Ile Ser Thr Thr Thr Pro Asn Pro Glu
    3545                3550                3555
Val Gly Met Ser Thr Met Asp Ser Thr Pro Ala Thr Glu Arg Arg
    3560                3565                3570
Thr Thr Ser Thr Glu His Pro Ser Thr Trp Ser Ser Thr Ala Ala
    3575                3580                3585
Ser Asp Ser Trp Thr Val Thr Asp Met Thr Ser Asn Leu Lys Val
    3590                3595                3600
Ala Arg Ser Pro Gly Thr Ile Ser Thr Met His Thr Thr Ser Phe
    3605                3610                3615
Leu Ala Ser Ser Thr Glu Leu Asp Ser Met Ser Thr Pro His Gly
    3620                3625                3630
Arg Ile Thr Val Ile Gly Thr Ser Leu Val Thr Pro Ser Ser Asp
    3635                3640                3645
Ala Ser Ala Val Lys Thr Glu Thr Ser Thr Ser Glu Arg Thr Leu
    3650                3655                3660
Ser Pro Ser Asp Thr Thr Ala Ser Thr Pro Ile Ser Thr Phe Ser
    3665                3670                3675
Arg Val Gln Arg Met Ser Ile Ser Val Pro Asp Ile Leu Ser Thr
    3680                3685                3690
Ser Trp Thr Pro Ser Ser Thr Glu Ala Glu Asp Val Pro Val Ser
    3695                3700                3705
Met Val Ser Thr Asp His Ala Ser Thr Lys Thr Asp Pro Asn Thr
    3710                3715                3720
Pro Leu Ser Thr Phe Leu Phe Asp Ser Leu Ser Thr Leu Asp Trp
    3725                3730                3735
Asp Thr Gly Arg Ser Leu Ser Ser Ala Thr Ala Thr Thr Ser Ala
    3740                3745                3750
Pro Gln Gly Ala Thr Thr Pro Gln Glu Leu Thr Leu Glu Thr Met
    3755                3760                3765
```

```
Ile Ser Pro Ala Thr Ser Gln Leu Pro Phe Ser Ile Gly His Ile
    3770            3775            3780

Thr Ser Ala Val Thr Pro Ala Ala Met Ala Arg Ser Ser Gly Val
    3785            3790            3795

Thr Phe Ser Arg Pro Asp Pro Thr Ser Lys Lys Ala Glu Gln Thr
    3800            3805            3810

Ser Thr Gln Leu Pro Thr Thr Ser Ala His Pro Gly Gln Val
    3815            3820            3825

Pro Arg Ser Ala Ala Thr Thr Leu Asp Val Ile Pro His Thr Ala
    3830            3835            3840

Lys Thr Pro Asp Ala Thr Phe Gln Arg Gln Gly Gln Thr Ala Leu
    3845            3850            3855

Thr Thr Glu Ala Arg Ala Thr Ser Asp Ser Trp Asn Glu Lys Glu
    3860            3865            3870

Lys Ser Thr Pro Ser Ala Pro Trp Ile Thr Glu Met Met Asn Ser
    3875            3880            3885

Val Ser Glu Asp Thr Ile Lys Glu Val Thr Ser Ser Ser Ser Val
    3890            3895            3900

Leu Arg Thr Leu Asn Thr Leu Asp Ile Asn Leu Glu Ser Gly Thr
    3905            3910            3915

Thr Ser Ser Pro Ser Trp Lys Ser Ser Pro Tyr Glu Arg Ile Ala
    3920            3925            3930

Pro Ser Glu Ser Thr Thr Asp Lys Glu Ala Ile His Pro Ser Thr
    3935            3940            3945

Asn Thr Val Glu Thr Thr Gly Trp Val Thr Ser Ser Glu His Ala
    3950            3955            3960

Ser His Ser Thr Ile Pro Ala His Ser Ala Ser Ser Lys Leu Thr
    3965            3970            3975

Ser Pro Val Val Thr Thr Ser Thr Arg Glu Gln Ala Ile Val Ser
    3980            3985            3990

Met Ser Thr Thr Thr Trp Pro Glu Ser Thr Arg Ala Arg Thr Glu
    3995            4000            4005

Pro Asn Ser Phe Leu Thr Ile Glu Leu Arg Asp Val Ser Pro Tyr
    4010            4015            4020

Met Asp Thr Ser Ser Thr Gln Thr Ser Ile Ile Ser Ser Pro
    4025            4030            4035

Gly Ser Thr Ala Ile Thr Lys Gly Pro Arg Thr Glu Ile Thr Ser
    4040            4045            4050

Ser Lys Arg Ile Ser Ser Ser Phe Leu Ala Gln Ser Met Arg Ser
    4055            4060            4065

Ser Asp Ser Pro Ser Glu Ala Ile Thr Arg Leu Ser Asn Phe Pro
    4070            4075            4080

Ala Met Thr Glu Ser Gly Gly Met Ile Leu Ala Met Gln Thr Ser
    4085            4090            4095

Pro Pro Gly Ala Thr Ser Leu Ser Ala Pro Thr Leu Asp Thr Ser
    4100            4105            4110

Ala Thr Ala Ser Trp Thr Gly Thr Pro Leu Ala Thr Thr Gln Arg
    4115            4120            4125

Phe Thr Tyr Ser Glu Lys Thr Thr Leu Phe Ser Lys Gly Pro Glu
    4130            4135            4140

Asp Thr Ser Gln Pro Ser Pro Pro Ser Val Glu Glu Thr Ser Ser
    4145            4150            4155
```

-continued

```
Ser Ser  Ser Leu Val Pro Ile His Ala Thr Thr Ser  Pro Ser Asn
    4160             4165                4170

Ile Leu  Leu Thr Ser Gln Gly His Ser Pro Ser Ser  Thr Pro Pro
    4175             4180                4185

Val Thr  Ser Val Phe Leu Ser Glu Thr Ser Gly Leu  Gly Lys Thr
    4190             4195                4200

Thr Asp  Met Ser Arg Ile Ser Leu Glu Pro Gly Thr  Ser Leu Pro
    4205             4210                4215

Pro Asn  Leu Ser Ser Thr Ala Gly Glu Ala Leu Ser  Thr Tyr Glu
    4220             4225                4230

Ala Ser  Arg Asp Thr Lys Ala Ile His His Ser Ala  Asp Thr Ala
    4235             4240                4245

Val Thr  Asn Met Glu Ala Thr Ser Ser Glu Tyr Ser  Pro Ile Pro
    4250             4255                4260

Gly His  Thr Lys Pro Ser Lys Ala Thr Ser Pro Leu  Val Thr Ser
    4265             4270                4275

His Ile  Met Gly Asp Ile Thr Ser Ser Thr Ser Val  Phe Gly Ser
    4280             4285                4290

Ser Glu  Thr Thr Glu Ile Glu Thr Val Ser Ser Val  Asn Gln Gly
    4295             4300                4305

Leu Gln  Glu Arg Ser Thr Ser Gln Val Ala Ser Ser  Ala Thr Glu
    4310             4315                4320

Thr Ser  Thr Val Ile Thr His Val Ser Ser Gly Asp  Ala Thr Thr
    4325             4330                4335

His Val  Thr Lys Thr Gln Ala Thr Phe Ser Ser Gly  Thr Ser Ile
    4340             4345                4350

Ser Ser  Pro His Gln Phe Ile Thr Ser Thr Asn Thr  Phe Thr Asp
    4355             4360                4365

Val Ser  Thr Asn Pro Ser Thr Ser Leu Ile Met Thr  Glu Ser Ser
    4370             4375                4380

Gly Val  Thr Ile Thr Thr Gln Thr Gly Pro Thr Gly  Ala Ala Thr
    4385             4390                4395

Gln Gly  Pro Tyr Leu Leu Asp Thr Ser Thr Met Pro  Tyr Leu Thr
    4400             4405                4410

Glu Thr  Pro Leu Ala Val Thr Pro Asp Phe Met Gln  Ser Glu Lys
    4415             4420                4425

Thr Thr  Leu Ile Ser Lys Gly Pro Lys Asp Val Ser  Trp Thr Ser
    4430             4435                4440

Pro Pro  Ser Val Ala Glu Thr Ser Tyr Pro Ser Ser  Leu Thr Pro
    4445             4450                4455

Phe Leu  Val Thr Thr Ile Pro Pro Ala Thr Ser Thr  Leu Gln Gly
    4460             4465                4470

Gln His  Thr Ser Ser Pro Val Ser Ala Thr Ser Val  Leu Thr Ser
    4475             4480                4485

Gly Leu  Val Lys Thr Thr Asp Met Leu Asn Thr Ser  Met Glu Pro
    4490             4495                4500

Val Thr  Asn Ser Pro Gln Asn Leu Asn Asn Pro Ser  Asn Glu Ile
    4505             4510                4515

Leu Ala  Thr Leu Ala Ala Thr Thr Asp Ile Glu Thr  Ile His Pro
    4520             4525                4530

Ser Ile  Asn Lys Ala Val Thr Asn Met Gly Thr Ala  Ser Ser Ala
    4535             4540                4545

His Val  Leu His Ser Thr Leu Pro Val Ser Ser Glu  Pro Ser Thr
```

-continued

```
                4550                4555                4560
Ala Thr Ser Pro Met Val Pro Ala Ser Ser Met Gly Asp Ala Leu
            4565                4570                4575
Ala Ser Ile Ser Ile Pro Gly Ser Glu Thr Thr Asp Ile Glu Gly
            4580                4585                4590
Glu Pro Thr Ser Ser Leu Thr Ala Gly Arg Lys Glu Asn Ser Thr
            4595                4600                4605
Leu Gln Glu Met Asn Ser Thr Thr Glu Ser Asn Ile Ile Leu Ser
            4610                4615                4620
Asn Val Ser Val Gly Ala Ile Thr Glu Ala Thr Lys Met Glu Val
            4625                4630                4635
Pro Ser Phe Asp Ala Thr Phe Ile Pro Thr Pro Ala Gln Ser Thr
            4640                4645                4650
Lys Phe Pro Asp Ile Phe Ser Val Ala Ser Ser Arg Leu Ser Asn
            4655                4660                4665
Ser Pro Pro Met Thr Ile Ser Thr His Met Thr Thr Thr Gln Thr
            4670                4675                4680
Gly Ser Ser Gly Ala Thr Ser Lys Ile Pro Leu Ala Leu Asp Thr
            4685                4690                4695
Ser Thr Leu Glu Thr Ser Ala Gly Thr Pro Ser Val Val Thr Glu
            4700                4705                4710
Gly Phe Ala His Ser Lys Ile Thr Thr Ala Met Asn Asn Asp Val
            4715                4720                4725
Lys Asp Val Ser Gln Thr Asn Pro Pro Phe Gln Asp Glu Ala Ser
            4730                4735                4740
Ser Pro Ser Ser Gln Ala Pro Val Leu Val Thr Thr Leu Pro Ser
            4745                4750                4755
Ser Val Ala Phe Thr Pro Gln Trp His Ser Thr Ser Ser Pro Val
            4760                4765                4770
Ser Met Ser Ser Val Leu Thr Ser Ser Leu Val Lys Thr Ala Gly
            4775                4780                4785
Lys Val Asp Thr Ser Leu Glu Thr Val Thr Ser Ser Pro Gln Ser
            4790                4795                4800
Met Ser Asn Thr Leu Asp Asp Ile Ser Val Thr Ser Ala Ala Thr
            4805                4810                4815
Thr Asp Ile Glu Thr Thr His Pro Ser Ile Asn Thr Val Val Thr
            4820                4825                4830
Asn Val Gly Thr Thr Gly Ser Ala Phe Glu Ser His Ser Thr Val
            4835                4840                4845
Ser Ala Tyr Pro Glu Pro Ser Lys Val Thr Ser Pro Asn Val Thr
            4850                4855                4860
Thr Ser Thr Met Glu Asp Thr Thr Ile Ser Arg Ser Ile Pro Lys
            4865                4870                4875
Ser Ser Lys Thr Thr Arg Thr Glu Thr Glu Thr Ser Ser Leu
            4880                4885                4890
Thr Pro Lys Leu Arg Glu Thr Ser Ile Ser Gln Glu Ile Thr Ser
            4895                4900                4905
Ser Thr Glu Thr Ser Thr Val Pro Tyr Lys Glu Leu Thr Gly Ala
            4910                4915                4920
Thr Thr Glu Val Ser Arg Thr Asp Val Thr Ser Ser Ser Ser Thr
            4925                4930                4935
Ser Phe Pro Gly Pro Asp Gln Ser Thr Val Ser Leu Asp Ile Ser
            4940                4945                4950
```

-continued

```
Thr Glu Thr Asn Thr Arg Leu Ser Thr Ser Pro Ile Met Thr Glu
    4955            4960                4965

Ser Ala Glu Ile Thr Ile Thr Thr Gln Thr Gly Pro His Gly Ala
    4970            4975                4980

Thr Ser Gln Asp Thr Phe Thr Met Asp Pro Ser Asn Thr Thr Pro
    4985            4990                4995

Gln Ala Gly Ile His Ser Ala Met Thr His Gly Phe Ser Gln Leu
    5000            5005                5010

Asp Val Thr Thr Leu Met Ser Arg Ile Pro Gln Asp Val Ser Trp
    5015            5020                5025

Thr Ser Pro Pro Ser Val Asp Lys Thr Ser Pro Ser Ser Phe
    5030            5035                5040

Leu Ser Ser Pro Ala Met Thr Thr Pro Ser Leu Ile Ser Ser Thr
    5045            5050                5055

Leu Pro Glu Asp Lys Leu Ser Ser Pro Met Thr Ser Leu Leu Thr
    5060            5065                5070

Ser Gly Leu Val Lys Ile Thr Asp Ile Leu Arg Thr Arg Leu Glu
    5075            5080                5085

Pro Val Thr Ser Ser Leu Pro Asn Phe Ser Thr Ser Asp Lys
    5090            5095                5100

Ile Leu Ala Thr Ser Lys Asp Ser Lys Asp Thr Lys Glu Ile Phe
    5105            5110                5115

Pro Ser Ile Asn Thr Glu Glu Thr Asn Val Lys Ala Asn Asn Ser
    5120            5125                5130

Gly His Glu Ser His Ser Pro Ala Leu Ala Asp Ser Glu Thr Pro
    5135            5140                5145

Lys Ala Thr Thr Gln Met Val Ile Thr Thr Thr Val Gly Asp Pro
    5150            5155                5160

Ala Pro Ser Thr Ser Met Pro Val His Gly Ser Ser Glu Thr Thr
    5165            5170                5175

Asn Ile Lys Arg Glu Pro Thr Tyr Phe Leu Thr Pro Arg Leu Arg
    5180            5185                5190

Glu Thr Ser Thr Ser Gln Glu Ser Ser Phe Pro Thr Asp Thr Ser
    5195            5200                5205

Phe Leu Leu Ser Lys Val Pro Thr Gly Thr Ile Thr Glu Val Ser
    5210            5215                5220

Ser Thr Gly Val Asn Ser Ser Ser Lys Ile Ser Thr Pro Asp His
    5225            5230                5235

Asp Lys Ser Thr Val Pro Pro Asp Thr Phe Thr Gly Glu Ile Pro
    5240            5245                5250

Arg Val Phe Thr Ser Ser Ile Lys Thr Lys Ser Ala Glu Met Thr
    5255            5260                5265

Ile Thr Thr Gln Ala Ser Pro Pro Glu Ser Ala Ser His Ser Thr
    5270            5275                5280

Leu Pro Leu Asp Thr Ser Thr Thr Leu Ser Gln Gly Gly Thr His
    5285            5290                5295

Ser Thr Val Thr Gln Gly Phe Pro Tyr Ser Glu Val Thr Thr Leu
    5300            5305                5310

Met Gly Met Gly Pro Gly Asn Val Ser Trp Met Thr Thr Pro Pro
    5315            5320                5325

Val Glu Glu Thr Ser Ser Val Ser Ser Leu Met Ser Ser Pro Ala
    5330            5335                5340
```

```
Met Thr Ser Pro Ser Pro Val Ser Ser Thr Ser Pro Gln Ser Ile
5345                5350                5355

Pro Ser Ser Pro Leu Pro Val Thr Ala Leu Pro Thr Ser Val Leu
5360                5365                5370

Val Thr Thr Thr Asp Val Leu Gly Thr Thr Ser Pro Glu Ser Val
5375                5380                5385

Thr Ser Ser Pro Pro Asn Leu Ser Ser Ile Thr His Glu Arg Pro
5390                5395                5400

Ala Thr Tyr Lys Asp Thr Ala His Thr Glu Ala Ala Met His His
5405                5410                5415

Ser Thr Asn Thr Ala Val Thr Asn Val Gly Thr Ser Gly Ser Gly
5420                5425                5430

His Lys Ser Gln Ser Ser Val Leu Ala Asp Ser Glu Thr Ser Lys
5435                5440                5445

Ala Thr Pro Leu Met Ser Thr Thr Ser Thr Leu Gly Asp Thr Ser
5450                5455                5460

Val Ser Thr Ser Thr Pro Asn Ile Ser Gln Thr Asn Gln Ile Gln
5465                5470                5475

Thr Glu Pro Thr Ala Ser Leu Ser Pro Arg Leu Arg Glu Ser Ser
5480                5485                5490

Thr Ser Glu Lys Thr Ser Ser Thr Thr Glu Thr Asn Thr Ala Phe
5495                5500                5505

Ser Tyr Val Pro Thr Gly Ala Ile Thr Gln Ala Ser Arg Thr Glu
5510                5515                5520

Ile Ser Ser Ser Arg Thr Ser Ile Ser Asp Leu Asp Arg Pro Thr
5525                5530                5535

Ile Ala Pro Asp Ile Ser Thr Gly Met Ile Thr Arg Leu Phe Thr
5540                5545                5550

Ser Pro Ile Met Thr Lys Ser Ala Glu Met Thr Val Thr Thr Gln
5555                5560                5565

Thr Thr Thr Pro Gly Ala Thr Ser Gln Gly Ile Leu Pro Trp Asp
5570                5575                5580

Thr Ser Thr Thr Leu Phe Gln Gly Gly Thr His Ser Thr Val Ser
5585                5590                5595

Gln Gly Phe Pro His Ser Glu Ile Thr Thr Leu Arg Ser Arg Thr
5600                5605                5610

Pro Gly Asp Val Ser Trp Met Thr Thr Pro Pro Val Glu Glu Thr
5615                5620                5625

Ser Ser Gly Phe Ser Leu Met Ser Pro Ser Met Thr Ser Pro Ser
5630                5635                5640

Pro Val Ser Ser Thr Ser Pro Glu Ser Ile Pro Ser Ser Pro Leu
5645                5650                5655

Pro Val Thr Ala Leu Leu Thr Ser Val Leu Val Thr Thr Thr Asn
5660                5665                5670

Val Leu Gly Thr Thr Ser Pro Glu Pro Val Thr Ser Ser Pro Pro
5675                5680                5685

Asn Leu Ser Ser Pro Thr Gln Glu Arg Leu Thr Thr Tyr Lys Asp
5690                5695                5700

Thr Ala His Thr Glu Ala Met His Ala Ser Met His Thr Asn Thr
5705                5710                5715

Ala Val Ala Asn Val Gly Thr Ser Ile Ser Gly His Glu Ser Gln
5720                5725                5730

Ser Ser Val Pro Ala Asp Ser His Thr Ser Lys Ala Thr Ser Pro
```

-continued

```
            5735                5740                5745
Met Gly Ile Thr Phe Ala Met Gly Asp Thr Ser Val Ser Thr Ser
            5750                5755                5760
Thr Pro Ala Phe Phe Glu Thr Arg Ile Gln Thr Glu Ser Thr Ser
            5765                5770                5775
Ser Leu Ile Pro Gly Leu Arg Asp Thr Arg Thr Ser Glu Glu Ile
            5780                5785                5790
Asn Thr Val Thr Glu Thr Ser Thr Val Leu Ser Glu Val Pro Thr
            5795                5800                5805
Thr Thr Thr Thr Glu Val Ser Arg Thr Glu Val Ile Thr Ser Ser
            5810                5815                5820
Arg Thr Thr Ile Ser Gly Pro Asp His Ser Lys Met Ser Pro Tyr
            5825                5830                5835
Ile Ser Thr Glu Thr Ile Thr Arg Leu Ser Thr Phe Pro Phe Val
            5840                5845                5850
Thr Gly Ser Thr Glu Met Ala Ile Thr Asn Gln Thr Gly Pro Ile
            5855                5860                5865
Gly Thr Ile Ser Gln Ala Thr Leu Thr Leu Asp Thr Ser Ser Thr
            5870                5875                5880
Ala Ser Trp Glu Gly Thr His Ser Pro Val Thr Gln Arg Phe Pro
            5885                5890                5895
His Ser Glu Glu Thr Thr Thr Met Ser Arg Ser Thr Lys Gly Val
            5900                5905                5910
Ser Trp Gln Ser Pro Pro Ser Val Glu Glu Thr Ser Ser Pro Ser
            5915                5920                5925
Ser Pro Val Pro Leu Pro Ala Ile Thr Ser His Ser Ser Leu Tyr
            5930                5935                5940
Ser Ala Val Ser Gly Ser Ser Pro Thr Ser Ala Leu Pro Val Thr
            5945                5950                5955
Ser Leu Leu Thr Ser Gly Arg Arg Lys Thr Ile Asp Met Leu Asp
            5960                5965                5970
Thr His Ser Glu Leu Val Thr Ser Ser Leu Pro Ser Ala Ser Ser
            5975                5980                5985
Phe Ser Gly Glu Ile Leu Thr Ser Glu Ala Ser Thr Asn Thr Glu
            5990                5995                6000
Thr Ile His Phe Ser Glu Asn Thr Ala Glu Thr Asn Met Gly Thr
            6005                6010                6015
Thr Asn Ser Met His Lys Leu His Ser Ser Val Ser Ile His Ser
            6020                6025                6030
Gln Pro Ser Gly His Thr Pro Pro Lys Val Thr Gly Ser Met Met
            6035                6040                6045
Glu Asp Ala Ile Val Ser Thr Ser Thr Pro Gly Ser Pro Glu Thr
            6050                6055                6060
Lys Asn Val Asp Arg Asp Ser Thr Ser Pro Leu Thr Pro Glu Leu
            6065                6070                6075
Lys Glu Asp Ser Thr Ala Leu Val Met Asn Ser Thr Thr Glu Ser
            6080                6085                6090
Asn Thr Val Phe Ser Ser Val Ser Leu Asp Ala Ala Thr Glu Val
            6095                6100                6105
Ser Arg Ala Glu Val Thr Tyr Tyr Asp Pro Thr Phe Met Pro Ala
            6110                6115                6120
Ser Ala Gln Ser Thr Lys Ser Pro Asp Ile Ser Pro Glu Ala Ser
            6125                6130                6135
```

-continued

```
Ser Ser His Ser Asn Ser Pro Pro Leu Thr Ile Ser  Thr His Lys
    6140            6145                6150

Thr Ile Ala Thr Gln Thr Gly Pro Ser Gly Val Thr  Ser Leu Gly
    6155            6160                6165

Gln Leu Thr Leu Asp Thr Ser Thr Ile Ala Thr Ser  Ala Gly Thr
    6170            6175                6180

Pro Ser Ala Arg Thr Gln Asp Phe Val Asp Ser Glu  Thr Thr Ser
    6185            6190                6195

Val Met Asn Asn Asp Leu Asn Asp Val Leu Lys Thr  Ser Pro Phe
    6200            6205                6210

Ser Ala Glu Glu Ala Asn Ser Leu Ser Ser Gln Ala  Pro Leu Leu
    6215            6220                6225

Val Thr Thr Ser Pro Ser Pro Val Thr Ser Thr Leu  Gln Glu His
    6230            6235                6240

Ser Thr Ser Ser Leu Val Ser Val Thr Ser Val Pro  Thr Pro Thr
    6245            6250                6255

Leu Ala Lys Ile Thr Asp Met Asp Thr Asn Leu Glu  Pro Val Thr
    6260            6265                6270

Arg Ser Pro Gln Asn Leu Arg Asn Thr Leu Ala Thr  Ser Glu Ala
    6275            6280                6285

Thr Thr Asp Thr His Thr Met His Pro Ser Ile Asn  Thr Ala Val
    6290            6295                6300

Ala Asn Val Gly Thr Thr Ser Ser Pro Asn Glu Phe  Tyr Phe Thr
    6305            6310                6315

Val Ser Pro Asp Ser Asp Pro Tyr Lys Ala Thr Ser  Ala Val Val
    6320            6325                6330

Ile Thr Ser Thr Ser Gly Asp Ser Ile Val Ser Thr  Ser Met Pro
    6335            6340                6345

Arg Ser Ser Ala Met Lys Lys Ile Glu Ser Glu Thr  Thr Phe Ser
    6350            6355                6360

Leu Ile Phe Arg Leu Arg Glu Thr Ser Thr Ser Gln  Lys Ile Gly
    6365            6370                6375

Ser Ser Ser Asp Thr Ser Thr Val Phe Asp Lys Ala  Phe Thr Ala
    6380            6385                6390

Ala Thr Thr Glu Val Ser Arg Thr Glu Leu Thr Ser  Ser Ser Arg
    6395            6400                6405

Thr Ser Ile Gln Gly Thr Glu Lys Pro Thr Met Ser  Pro Asp Thr
    6410            6415                6420

Ser Thr Arg Ser Val Thr Met Leu Ser Thr Phe Ala  Gly Leu Thr
    6425            6430                6435

Lys Ser Glu Glu Arg Thr Ile Ala Thr Gln Thr Gly  Pro His Arg
    6440            6445                6450

Ala Thr Ser Gln Gly Thr Leu Thr Trp Asp Thr Ser  Ile Thr Thr
    6455            6460                6465

Ser Gln Ala Gly Thr His Ser Ala Met Thr His Gly  Phe Ser Gln
    6470            6475                6480

Leu Asp Leu Ser Thr Leu Thr Ser Arg Val Pro Glu  Tyr Ile Ser
    6485            6490                6495

Gly Thr Ser Pro Pro Ser Val Glu Lys Thr Ser Ser  Ser Ser Ser
    6500            6505                6510

Leu Leu Ser Leu Pro Ala Ile Thr Ser Pro Ser Pro  Val Pro Thr
    6515            6520                6525
```

```
Thr Leu Pro Glu Ser Arg Pro Ser Ser Pro Val His Leu Thr Ser
    6530            6535            6540

Leu Pro Thr Ser Gly Leu Val Lys Thr Thr Asp Met Leu Ala Ser
    6545            6550            6555

Val Ala Ser Leu Pro Pro Asn Leu Gly Ser Thr Ser His Lys Ile
    6560            6565            6570

Pro Thr Thr Ser Glu Asp Ile Lys Asp Thr Glu Lys Met Tyr Pro
    6575            6580            6585

Ser Thr Asn Ile Ala Val Thr Asn Val Gly Thr Thr Thr Ser Glu
    6590            6595            6600

Lys Glu Ser Tyr Ser Ser Val Pro Ala Tyr Ser Glu Pro Pro Lys
    6605            6610            6615

Val Thr Ser Pro Met Val Thr Ser Phe Asn Ile Arg Asp Thr Ile
    6620            6625            6630

Val Ser Thr Ser Met Pro Gly Ser Ser Glu Ile Thr Arg Ile Glu
    6635            6640            6645

Met Glu Ser Thr Phe Ser Leu Ala His Gly Leu Lys Gly Thr Ser
    6650            6655            6660

Thr Ser Gln Asp Pro Ile Val Ser Thr Glu Lys Ser Ala Val Leu
    6665            6670            6675

His Lys Leu Thr Thr Gly Ala Thr Glu Thr Ser Arg Thr Glu Val
    6680            6685            6690

Ala Ser Ser Arg Arg Thr Ser Ile Pro Gly Pro Asp His Ser Thr
    6695            6700            6705

Glu Ser Pro Asp Ile Ser Thr Glu Val Ile Pro Ser Leu Pro Ile
    6710            6715            6720

Ser Leu Gly Ile Thr Glu Ser Ser Asn Met Thr Ile Ile Thr Arg
    6725            6730            6735

Thr Gly Pro Pro Leu Gly Ser Thr Ser Gln Gly Thr Phe Thr Leu
    6740            6745            6750

Asp Thr Pro Thr Thr Ser Ser Arg Ala Gly Thr His Ser Met Ala
    6755            6760            6765

Thr Gln Glu Phe Pro His Ser Glu Met Thr Thr Val Met Asn Lys
    6770            6775            6780

Asp Pro Glu Ile Leu Ser Trp Thr Ile Pro Pro Ser Ile Glu Lys
    6785            6790            6795

Thr Ser Phe Ser Ser Ser Leu Met Pro Ser Pro Ala Met Thr Ser
    6800            6805            6810

Pro Pro Val Ser Ser Thr Leu Pro Lys Thr Ile His Thr Thr Pro
    6815            6820            6825

Ser Pro Met Thr Ser Leu Leu Thr Pro Ser Leu Val Met Thr Thr
    6830            6835            6840

Asp Thr Leu Gly Thr Ser Pro Glu Pro Thr Thr Ser Ser Pro Pro
    6845            6850            6855

Asn Leu Ser Ser Thr Ser His Glu Ile Leu Thr Thr Asp Glu Asp
    6860            6865            6870

Thr Thr Ala Ile Glu Ala Met His Pro Ser Thr Ser Thr Ala Ala
    6875            6880            6885

Thr Asn Val Glu Thr Thr Ser Ser Gly His Gly Ser Gln Ser Ser
    6890            6895            6900

Val Leu Ala Asp Ser Glu Lys Thr Lys Ala Thr Ala Pro Met Asp
    6905            6910            6915

Thr Thr Ser Thr Met Gly His Thr Thr Val Ser Thr Ser Met Ser
```

-continued

```
                 6920                      6925                      6930
Val  Ser  Ser  Glu  Thr  Thr  Lys  Ile  Lys  Arg  Glu  Ser  Thr  Tyr  Ser
                 6935                      6940                      6945

Leu  Thr  Pro  Gly  Leu  Arg  Glu  Thr  Ser  Ile  Ser  Gln  Asn  Ala  Ser
                 6950                      6955                      6960

Phe  Ser  Thr  Asp  Thr  Ser  Ile  Val  Leu  Ser  Glu  Val  Pro  Thr  Gly
                 6965                      6970                      6975

Thr  Thr  Ala  Glu  Val  Ser  Arg  Thr  Glu  Val  Thr  Ser  Ser  Gly  Arg
                 6980                      6985                      6990

Thr  Ser  Ile  Pro  Gly  Pro  Ser  Gln  Ser  Thr  Val  Leu  Pro  Glu  Ile
                 6995                      7000                      7005

Ser  Thr  Arg  Thr  Met  Thr  Arg  Leu  Phe  Ala  Ser  Pro  Thr  Met  Thr
                 7010                      7015                      7020

Glu  Ser  Ala  Glu  Met  Thr  Ile  Pro  Thr  Gln  Thr  Gly  Pro  Ser  Gly
                 7025                      7030                      7035

Ser  Thr  Ser  Gln  Asp  Thr  Leu  Thr  Leu  Asp  Thr  Ser  Thr  Thr  Lys
                 7040                      7045                      7050

Ser  Gln  Ala  Lys  Thr  His  Ser  Thr  Leu  Thr  Gln  Arg  Phe  Pro  His
                 7055                      7060                      7065

Ser  Glu  Met  Thr  Thr  Leu  Met  Ser  Arg  Gly  Pro  Gly  Asp  Met  Ser
                 7070                      7075                      7080

Trp  Gln  Ser  Ser  Pro  Ser  Leu  Glu  Asn  Pro  Ser  Ser  Leu  Pro  Ser
                 7085                      7090                      7095

Leu  Leu  Ser  Leu  Pro  Ala  Thr  Thr  Ser  Pro  Pro  Ile  Ser  Ser
                 7100                      7105                      7110

Thr  Leu  Pro  Val  Thr  Ile  Ser  Ser  Ser  Pro  Leu  Pro  Val  Thr  Ser
                 7115                      7120                      7125

Leu  Leu  Thr  Ser  Ser  Pro  Val  Thr  Thr  Thr  Asp  Met  Leu  His  Thr
                 7130                      7135                      7140

Ser  Pro  Glu  Leu  Val  Thr  Ser  Ser  Pro  Pro  Lys  Leu  Ser  His  Thr
                 7145                      7150                      7155

Ser  Asp  Glu  Arg  Leu  Thr  Thr  Gly  Lys  Asp  Thr  Thr  Asn  Thr  Glu
                 7160                      7165                      7170

Ala  Val  His  Pro  Ser  Thr  Asn  Thr  Ala  Ala  Ser  Asn  Val  Glu  Ile
                 7175                      7180                      7185

Pro  Ser  Ser  Gly  His  Glu  Ser  Pro  Ser  Ser  Ala  Leu  Ala  Asp  Ser
                 7190                      7195                      7200

Glu  Thr  Ser  Lys  Ala  Thr  Ser  Pro  Met  Phe  Ile  Thr  Ser  Thr  Gln
                 7205                      7210                      7215

Glu  Asp  Thr  Thr  Val  Ala  Ile  Ser  Thr  Pro  His  Phe  Leu  Glu  Thr
                 7220                      7225                      7230

Ser  Arg  Ile  Gln  Lys  Glu  Ser  Ile  Ser  Ser  Leu  Ser  Pro  Lys  Leu
                 7235                      7240                      7245

Arg  Glu  Thr  Gly  Ser  Ser  Val  Glu  Thr  Ser  Ser  Ala  Ile  Glu  Thr
                 7250                      7255                      7260

Ser  Ala  Val  Leu  Ser  Glu  Val  Ser  Ile  Gly  Ala  Thr  Thr  Glu  Ile
                 7265                      7270                      7275

Ser  Arg  Thr  Glu  Val  Thr  Ser  Ser  Ser  Arg  Thr  Ser  Ile  Ser  Gly
                 7280                      7285                      7290

Ser  Ala  Glu  Ser  Thr  Met  Leu  Pro  Glu  Ile  Ser  Thr  Thr  Arg  Lys
                 7295                      7300                      7305

Ile  Ile  Lys  Phe  Pro  Thr  Ser  Pro  Ile  Leu  Ala  Glu  Ser  Ser  Glu
                 7310                      7315                      7320
```

```
Met Thr Ile Lys Thr Gln Thr Ser Pro Pro Gly Ser Thr Ser Glu
            7325            7330            7335

Ser Thr Phe Thr Leu Asp Thr Ser Thr Pro Ser Leu Val Ile
            7340            7345            7350

Thr His Ser Thr Met Thr Gln Arg Leu Pro His Ser Glu Ile Thr
            7355            7360            7365

Thr Leu Val Ser Arg Gly Ala Gly Asp Val Pro Arg Pro Ser Ser
            7370            7375            7380

Leu Pro Val Glu Glu Thr Ser Pro Pro Ser Ser Gln Leu Ser Leu
            7385            7390            7395

Ser Ala Met Ile Ser Pro Ser Pro Val Ser Ser Thr Leu Pro Ala
            7400            7405            7410

Ser Ser His Ser Ser Ser Ala Ser Val Thr Ser Leu Leu Thr Pro
            7415            7420            7425

Gly Gln Val Lys Thr Thr Glu Val Leu Asp Ala Ser Ala Glu Pro
            7430            7435            7440

Glu Thr Ser Ser Pro Pro Ser Leu Ser Ser Thr Ser Val Glu Ile
            7445            7450            7455

Leu Ala Thr Ser Glu Val Thr Thr Asp Thr Glu Lys Ile His Pro
            7460            7465            7470

Phe Ser Asn Thr Ala Val Thr Lys Val Gly Thr Ser Ser Ser Gly
            7475            7480            7485

His Glu Ser Pro Ser Ser Val Leu Pro Asp Ser Glu Thr Thr Lys
            7490            7495            7500

Ala Thr Ser Ala Met Gly Thr Ile Ser Ile Met Gly Asp Thr Ser
            7505            7510            7515

Val Ser Thr Leu Thr Pro Ala Leu Ser Asn Thr Arg Lys Ile Gln
            7520            7525            7530

Ser Glu Pro Ala Ser Ser Leu Thr Thr Arg Leu Arg Glu Thr Ser
            7535            7540            7545

Thr Ser Glu Glu Thr Ser Leu Ala Thr Glu Ala Asn Thr Val Leu
            7550            7555            7560

Ser Lys Val Ser Thr Gly Ala Thr Thr Glu Val Ser Arg Thr Glu
            7565            7570            7575

Ala Ile Ser Phe Ser Arg Thr Ser Met Ser Gly Pro Glu Gln Ser
            7580            7585            7590

Thr Met Ser Gln Asp Ile Ser Ile Gly Thr Ile Pro Arg Ile Ser
            7595            7600            7605

Ala Ser Ser Val Leu Thr Glu Ser Ala Lys Met Thr Ile Thr Thr
            7610            7615            7620

Gln Thr Gly Pro Ser Glu Ser Thr Leu Glu Ser Thr Leu Asn Leu
            7625            7630            7635

Asn Thr Ala Thr Thr Pro Ser Trp Val Glu Thr His Ser Ile Val
            7640            7645            7650

Ile Gln Gly Phe Pro His Pro Glu Met Thr Thr Ser Met Gly Arg
            7655            7660            7665

Gly Pro Gly Gly Val Ser Trp Pro Ser Pro Phe Val Lys Glu
            7670            7675            7680

Thr Ser Pro Pro Ser Ser Pro Leu Ser Leu Pro Ala Val Thr Ser
            7685            7690            7695

Pro His Pro Val Ser Thr Thr Phe Leu Ala His Ile Pro Pro Ser
            7700            7705            7710
```

```
Pro Leu Pro Val Thr Ser Leu Leu Thr Ser Gly Pro Ala Thr Thr
7715                7720                7725

Thr Asp Ile Leu Gly Thr Ser Thr Glu Pro Gly Thr Ser Ser Ser
7730                7735                7740

Ser Ser Leu Ser Thr Thr Ser His Glu Arg Leu Thr Thr Tyr Lys
    7745                7750                7755

Asp Thr Ala His Thr Glu Ala Val His Pro Ser Thr Asn Thr Gly
7760                7765                7770

Gly Thr Asn Val Ala Thr Thr Ser Ser Gly Tyr Lys Ser Gln Ser
    7775                7780                7785

Ser Val Leu Ala Asp Ser Ser Pro Met Cys Thr Thr Ser Thr Met
    7790                7795                7800

Gly Asp Thr Ser Val Leu Thr Ser Thr Pro Ala Phe Leu Glu Thr
    7805                7810                7815

Arg Arg Ile Gln Thr Glu Leu Ala Ser Ser Leu Thr Pro Gly Leu
    7820                7825                7830

Arg Glu Ser Ser Gly Ser Glu Gly Thr Ser Ser Gly Thr Lys Met
    7835                7840                7845

Ser Thr Val Leu Ser Lys Val Pro Thr Gly Ala Thr Thr Glu Ile
    7850                7855                7860

Ser Lys Glu Asp Val Thr Ser Ile Pro Gly Pro Ala Gln Ser Thr
    7865                7870                7875

Ile Ser Pro Asp Ile Ser Thr Arg Thr Val Ser Trp Phe Ser Thr
    7880                7885                7890

Ser Pro Val Met Thr Glu Ser Ala Glu Ile Thr Met Asn Thr His
    7895                7900                7905

Thr Ser Pro Leu Gly Ala Thr Thr Gln Gly Thr Ser Thr Leu Asp
    7910                7915                7920

Thr Ser Ser Thr Thr Ser Leu Thr Met Thr His Ser Thr Ile Ser
    7925                7930                7935

Gln Gly Phe Ser His Ser Gln Met Ser Thr Leu Met Arg Arg Gly
    7940                7945                7950

Pro Glu Asp Val Ser Trp Met Ser Pro Pro Leu Leu Glu Lys Thr
    7955                7960                7965

Arg Pro Ser Phe Ser Leu Met Ser Ser Pro Ala Thr Thr Ser Pro
    7970                7975                7980

Ser Pro Val Ser Ser Thr Leu Pro Glu Ser Ile Ser Ser Ser Pro
    7985                7990                7995

Leu Pro Val Thr Ser Leu Leu Thr Ser Gly Leu Ala Lys Thr Thr
    8000                8005                8010

Asp Met Leu His Lys Ser Ser Glu Pro Val Thr Asn Ser Pro Ala
    8015                8020                8025

Asn Leu Ser Ser Thr Ser Val Glu Ile Leu Ala Thr Ser Glu Val
    8030                8035                8040

Thr Thr Asp Thr Glu Lys Thr His Pro Ser Ser Asn Arg Thr Val
    8045                8050                8055

Thr Asp Val Gly Thr Ser Ser Gly His Glu Ser Thr Ser Phe
    8060                8065                8070

Val Leu Ala Asp Ser Gln Thr Ser Lys Val Thr Ser Pro Met Val
    8075                8080                8085

Ile Thr Ser Thr Met Glu Asp Thr Ser Val Ser Thr Ser Thr Pro
    8090                8095                8100

Gly Phe Phe Glu Thr Ser Arg Ile Gln Thr Glu Pro Thr Ser Ser
```

-continued

```
              8105               8110             8115
Leu Thr Leu Gly Leu Arg Lys Thr Ser Ser Ser Glu Gly Thr Ser
              8120               8125             8130
Leu Ala Thr Glu Met Ser Thr Val Leu Ser Gly Val Pro Thr Gly
              8135               8140             8145
Ala Thr Ala Glu Val Ser Arg Thr Glu Val Thr Ser Ser Ser Arg
              8150               8155             8160
Thr Ser Ile Ser Gly Phe Ala Gln Leu Thr Val Ser Pro Glu Thr
              8165               8170             8175
Ser Thr Glu Thr Ile Thr Arg Leu Pro Thr Ser Ser Ile Met Thr
              8180               8185             8190
Glu Ser Ala Glu Met Met Ile Lys Thr Gln Thr Asp Pro Pro Gly
              8195               8200             8205
Ser Thr Pro Glu Ser Thr His Thr Val Asp Ile Ser Thr Thr Pro
              8210               8215             8220
Asn Trp Val Glu Thr His Ser Thr Val Thr Gln Arg Phe Ser His
              8225               8230             8235
Ser Glu Met Thr Thr Leu Val Ser Arg Ser Pro Gly Asp Met Leu
              8240               8245             8250
Trp Pro Ser Gln Ser Ser Val Glu Glu Thr Ser Ser Ala Ser Ser
              8255               8260             8265
Leu Leu Ser Leu Pro Ala Thr Thr Ser Pro Ser Pro Val Ser Ser
              8270               8275             8280
Thr Leu Val Glu Asp Phe Pro Ser Ala Ser Leu Pro Val Thr Ser
              8285               8290             8295
Leu Leu Asn Pro Gly Leu Val Ile Thr Thr Asp Arg Met Gly Ile
              8300               8305             8310
Ser Arg Glu Pro Gly Thr Ser Ser Thr Ser Asn Leu Ser Ser Thr
              8315               8320             8325
Ser His Glu Arg Leu Thr Thr Leu Glu Asp Thr Val Asp Thr Glu
              8330               8335             8340
Asp Met Gln Pro Ser Thr His Thr Ala Val Thr Asn Val Arg Thr
              8345               8350             8355
Ser Ile Ser Gly His Glu Ser Gln Ser Ser Val Leu Ser Asp Ser
              8360               8365             8370
Glu Thr Pro Lys Ala Thr Ser Pro Met Gly Thr Thr Tyr Thr Met
              8375               8380             8385
Gly Glu Thr Ser Val Ser Ile Ser Thr Ser Asp Phe Phe Glu Thr
              8390               8395             8400
Ser Arg Ile Gln Ile Glu Pro Thr Ser Ser Leu Thr Ser Gly Leu
              8405               8410             8415
Arg Glu Thr Ser Ser Ser Glu Arg Ile Ser Ser Ala Thr Glu Gly
              8420               8425             8430
Ser Thr Val Leu Ser Glu Val Pro Ser Gly Ala Thr Thr Glu Val
              8435               8440             8445
Ser Arg Thr Glu Val Ile Ser Ser Arg Gly Thr Ser Met Ser Gly
              8450               8455             8460
Pro Asp Gln Phe Thr Ile Ser Pro Asp Ile Ser Thr Glu Ala Ile
              8465               8470             8475
Thr Arg Leu Ser Thr Ser Pro Ile Met Thr Glu Ser Ala Glu Ser
              8480               8485             8490
Ala Ile Thr Ile Glu Thr Gly Ser Pro Gly Ala Thr Ser Glu Gly
              8495               8500             8505
```

-continued

| | | | | | | | | | | |
|---|---|---|---|---|---|---|---|---|---|---|
| Thr | Leu | Thr | Leu | Asp | Thr | Ser | Thr | Thr | Thr | Phe | Trp | Ser | Gly | Thr |
| | 8510 | | | | | 8515 | | | | | 8520 | | | |

Thr Leu Thr Leu Asp Thr Ser Thr Thr Thr Phe Trp Ser Gly Thr
    8510                8515                8520

His Ser Thr Ala Ser Pro Gly Phe Ser His Ser Glu Met Thr Thr
    8525                8530                8535

Leu Met Ser Arg Thr Pro Gly Asp Val Pro Trp Pro Ser Leu Pro
    8540                8545                8550

Ser Val Glu Glu Ala Ser Ser Val Ser Ser Ser Leu Ser Ser Pro
    8555                8560                8565

Ala Met Thr Ser Thr Ser Phe Phe Ser Thr Leu Pro Glu Ser Ile
    8570                8575                8580

Ser Ser Ser Pro His Pro Val Thr Ala Leu Leu Thr Leu Gly Pro
    8585                8590                8595

Val Lys Thr Thr Asp Met Leu Arg Thr Ser Ser Glu Pro Glu Thr
    8600                8605                8610

Ser Ser Pro Pro Asn Leu Ser Ser Thr Ser Ala Glu Ile Leu Ala
    8615                8620                8625

Thr Ser Glu Val Thr Lys Asp Arg Glu Lys Ile His Pro Ser Ser
    8630                8635                8640

Asn Thr Pro Val Val Asn Val Gly Thr Val Ile Tyr Lys His Leu
    8645                8650                8655

Ser Pro Ser Ser Val Leu Ala Asp Leu Val Thr Thr Lys Pro Thr
    8660                8665                8670

Ser Pro Met Ala Thr Thr Ser Thr Leu Gly Asn Thr Ser Val Ser
    8675                8680                8685

Thr Ser Thr Pro Ala Phe Pro Glu Thr Met Met Thr Gln Pro Thr
    8690                8695                8700

Ser Ser Leu Thr Ser Gly Leu Arg Glu Ile Ser Thr Ser Gln Glu
    8705                8710                8715

Thr Ser Ser Ala Thr Glu Arg Ser Ala Ser Leu Ser Gly Met Pro
    8720                8725                8730

Thr Gly Ala Thr Thr Lys Val Ser Arg Thr Glu Ala Leu Ser Leu
    8735                8740                8745

Gly Arg Thr Ser Thr Pro Gly Pro Ala Gln Ser Thr Ile Ser Pro
    8750                8755                8760

Glu Ile Ser Thr Glu Thr Ile Thr Arg Ile Ser Thr Pro Leu Thr
    8765                8770                8775

Thr Thr Gly Ser Ala Glu Met Thr Ile Thr Pro Lys Thr Gly His
    8780                8785                8790

Ser Gly Ala Ser Ser Gln Gly Thr Phe Thr Leu Asp Thr Ser Ser
    8795                8800                8805

Arg Ala Ser Trp Pro Gly Thr His Ser Ala Ala Thr His Arg Ser
    8810                8815                8820

Pro His Ser Gly Met Thr Thr Pro Met Ser Arg Gly Pro Glu Asp
    8825                8830                8835

Val Ser Trp Pro Ser Arg Pro Ser Val Glu Lys Thr Ser Pro Pro
    8840                8845                8850

Ser Ser Leu Val Ser Leu Ser Ala Val Thr Ser Pro Ser Pro Leu
    8855                8860                8865

Tyr Ser Thr Pro Ser Glu Ser Ser His Ser Ser Pro Leu Arg Val
    8870                8875                8880

Thr Ser Leu Phe Thr Pro Val Met Met Lys Thr Thr Asp Met Leu
    8885                8890                8895

```
Asp Thr Ser Leu Glu Pro Val Thr Thr Ser Pro Pro Ser Met Asn
8900                 8905                 8910

Ile Thr Ser Asp Glu Ser Leu Ala Thr Ser Lys Ala Thr Met Glu
    8915                 8920                 8925

Thr Glu Ala Ile Gln Leu Ser Glu Asn Thr Ala Val Thr Gln Met
    8930                 8935                 8940

Gly Thr Ile Ser Ala Arg Gln Glu Phe Tyr Ser Ser Tyr Pro Gly
    8945                 8950                 8955

Leu Pro Glu Pro Ser Lys Val Thr Ser Pro Val Val Thr Ser Ser
    8960                 8965                 8970

Thr Ile Lys Asp Ile Val Ser Thr Thr Ile Pro Ala Ser Ser Glu
    8975                 8980                 8985

Ile Thr Arg Ile Glu Met Glu Ser Thr Ser Thr Leu Thr Pro Thr
    8990                 8995                 9000

Pro Arg Glu Thr Ser Thr Ser Gln Glu Ile His Ser Ala Thr Lys
    9005                 9010                 9015

Pro Ser Thr Val Pro Tyr Lys Ala Leu Thr Ser Ala Thr Ile Glu
    9020                 9025                 9030

Asp Ser Met Thr Gln Val Met Ser Ser Ser Arg Gly Pro Ser Pro
    9035                 9040                 9045

Asp Gln Ser Thr Met Ser Gln Asp Ile Ser Thr Glu Val Ile Thr
    9050                 9055                 9060

Arg Leu Ser Thr Ser Pro Ile Lys Thr Glu Ser Thr Glu Met Thr
    9065                 9070                 9075

Ile Thr Thr Gln Thr Gly Ser Pro Gly Ala Thr Ser Arg Gly Thr
    9080                 9085                 9090

Leu Thr Leu Asp Thr Ser Thr Thr Phe Met Ser Gly Thr His Ser
    9095                 9100                 9105

Thr Ala Ser Gln Gly Phe Ser His Ser Gln Met Thr Ala Leu Met
    9110                 9115                 9120

Ser Arg Thr Pro Gly Asp Val Pro Trp Leu Ser His Pro Ser Val
    9125                 9130                 9135

Glu Glu Ala Ser Ser Ala Ser Phe Ser Leu Ser Ser Pro Val Met
    9140                 9145                 9150

Thr Ser Ser Ser Pro Val Ser Ser Thr Leu Pro Asp Ser Ile His
    9155                 9160                 9165

Ser Ser Ser Leu Pro Val Thr Ser Leu Leu Thr Ser Gly Leu Val
    9170                 9175                 9180

Lys Thr Thr Glu Leu Leu Gly Thr Ser Ser Glu Pro Glu Thr Ser
    9185                 9190                 9195

Ser Pro Pro Asn Leu Ser Ser Thr Ser Ala Glu Ile Leu Ala Ile
    9200                 9205                 9210

Thr Glu Val Thr Thr Asp Thr Glu Lys Leu Glu Met Thr Asn Val
    9215                 9220                 9225

Val Thr Ser Gly Tyr Thr His Glu Ser Pro Ser Ser Val Leu Ala
    9230                 9235                 9240

Asp Ser Val Thr Thr Lys Ala Thr Ser Ser Met Gly Ile Thr Tyr
    9245                 9250                 9255

Pro Thr Gly Asp Thr Asn Val Leu Thr Ser Thr Pro Ala Phe Ser
    9260                 9265                 9270

Asp Thr Ser Arg Ile Gln Thr Lys Ser Lys Leu Ser Leu Thr Pro
    9275                 9280                 9285

Gly Leu Met Glu Thr Ser Ile Ser Glu Glu Thr Ser Ser Ala Thr
```

-continued

```
               9290                  9295                  9300
Glu Lys Ser Thr Val Leu Ser  Ser Val Pro Thr Gly Ala Thr Thr
     9305                  9310                  9315
Glu Val Ser Arg Thr Glu Ala  Ile Ser Ser Arg  Thr Ser Ile
     9320                  9325                  9330
Pro Gly Pro Ala Gln Ser Thr  Met Ser Ser Asp Thr Ser Met Glu
     9335                  9340                  9345
Thr Ile Thr Arg Ile Ser Thr  Pro Leu Thr Arg Lys Glu Ser Thr
     9350                  9355                  9360
Asp Met Ala Ile Thr Pro Lys  Thr Gly Pro Ser Gly Ala Thr Ser
     9365                  9370                  9375
Gln Gly Thr Phe Thr Leu Asp  Ser Ser Ser Thr Ala Ser Trp Pro
     9380                  9385                  9390
Gly Thr His Ser Ala Thr Thr  Gln Arg Phe Pro Gln Ser Val Val
     9395                  9400                  9405
Thr Thr Pro Met Ser Arg Gly  Pro Glu Asp Val Ser Trp Pro Ser
     9410                  9415                  9420
Pro Leu Ser Val Glu Lys Asn  Ser Pro Pro Ser Ser Leu Val Ser
     9425                  9430                  9435
Ser Ser Ser Val Thr Ser Pro  Ser Pro Leu Tyr Ser Thr Pro Ser
     9440                  9445                  9450
Gly Ser Ser His Ser Ser Pro  Val Pro Val Thr Ser Leu Phe Thr
     9455                  9460                  9465
Ser Ile Met Met Lys Ala Thr  Asp Met Leu Asp Ala Ser Leu Glu
     9470                  9475                  9480
Pro Glu Thr Thr Ser Ala Pro  Asn Met Asn Ile Thr Ser Asp Glu
     9485                  9490                  9495
Ser Leu Ala Ala Ser Lys Ala  Thr Thr Glu Thr Glu Ala Ile His
     9500                  9505                  9510
Val Phe Glu Asn Thr Ala Ala  Ser His Val Glu Thr Thr Ser Ala
     9515                  9520                  9525
Thr Glu Glu Leu Tyr Ser Ser  Ser Pro Gly Phe Ser Glu Pro Thr
     9530                  9535                  9540
Lys Val Ile Ser Pro Val Val  Thr Ser Ser Ser Ile Arg Asp Asn
     9545                  9550                  9555
Met Val Ser Thr Thr Met Pro  Gly Ser Ser Gly Ile Thr Arg Ile
     9560                  9565                  9570
Glu Ile Glu Ser Met Ser Ser  Leu Thr Pro Gly Leu Arg Glu Thr
     9575                  9580                  9585
Arg Thr Ser Gln Asp Ile Thr  Ser Ser Thr Glu Thr Ser Thr Val
     9590                  9595                  9600
Leu Tyr Lys Met Pro Ser Gly  Ala Thr Pro Glu Val Ser Arg Thr
     9605                  9610                  9615
Glu Val Met Pro Ser Ser Arg  Thr Ser Ile Pro Gly Pro Ala Gln
     9620                  9625                  9630
Ser Thr Met Ser Leu Asp Ile  Ser Asp Glu Val Val Thr Arg Leu
     9635                  9640                  9645
Ser Thr Ser Pro Ile Met Thr  Glu Ser Ala Glu Ile Thr Ile Thr
     9650                  9655                  9660
Thr Gln Thr Gly Tyr Ser Leu  Ala Thr Ser Gln Val Thr Leu Pro
     9665                  9670                  9675
Leu Gly Thr Ser Met Thr Phe  Leu Ser Gly Thr His Ser Thr Met
     9680                  9685                  9690
```

```
Ser Gln Gly Leu Ser His Ser Glu Met Thr Asn Leu Met Ser Arg
    9695             9700                 9705

Gly Pro Glu Ser Leu Ser Trp Thr Ser Pro Arg Phe Val Glu Thr
    9710             9715                 9720

Thr Arg Ser Ser Ser Ser Leu Thr Ser Leu Pro Leu Thr Thr Ser
    9725             9730                 9735

Leu Ser Pro Val Ser Ser Thr Leu Leu Asp Ser Ser Pro Ser Ser
    9740             9745                 9750

Pro Leu Pro Val Thr Ser Leu Ile Leu Pro Gly Leu Val Lys Thr
    9755             9760                 9765

Thr Glu Val Leu Asp Thr Ser Ser Glu Pro Lys Thr Ser Ser Ser
    9770             9775                 9780

Pro Asn Leu Ser Ser Thr Ser Val Glu Ile Pro Ala Thr Ser Glu
    9785             9790                 9795

Ile Met Thr Asp Thr Glu Lys Ile His Pro Ser Ser Asn Thr Ala
    9800             9805                 9810

Val Ala Lys Val Arg Thr Ser Ser Ser Val His Glu Ser His Ser
    9815             9820                 9825

Ser Val Leu Ala Asp Ser Glu Thr Thr Ile Thr Ile Pro Ser Met
    9830             9835                 9840

Gly Ile Thr Ser Ala Val Asp Asp Thr Thr Val Phe Thr Ser Asn
    9845             9850                 9855

Pro Ala Phe Ser Glu Thr Arg Arg Ile Pro Thr Glu Pro Thr Phe
    9860             9865                 9870

Ser Leu Thr Pro Gly Phe Arg Glu Thr Ser Thr Ser Glu Glu Thr
    9875             9880                 9885

Thr Ser Ile Thr Glu Thr Ser Ala Val Leu Tyr Gly Val Pro Thr
    9890             9895                 9900

Ser Ala Thr Thr Glu Val Ser Met Thr Glu Ile Met Ser Ser Asn
    9905             9910                 9915

Arg Ile His Ile Pro Asp Ser Asp Gln Ser Thr Met Ser Pro Asp
    9920             9925                 9930

Ile Ile Thr Glu Val Ile Thr Arg Leu Ser Ser Ser Ser Met Met
    9935             9940                 9945

Ser Glu Ser Thr Gln Met Thr Ile Thr Thr Gln Lys Ser Ser Pro
    9950             9955                 9960

Gly Ala Thr Ala Gln Ser Thr Leu Thr Leu Ala Thr Thr Thr Ala
    9965             9970                 9975

Pro Leu Ala Arg Thr His Ser Thr Val Pro Pro Arg Phe Leu His
    9980             9985                 9990

Ser Glu Met Thr Thr Leu Met Ser Arg Ser Pro Glu Asn Pro Ser
    9995             10000                10005

Trp Lys Ser Ser Leu Phe Val Glu Lys Thr Ser Ser Ser Ser Ser
    10010            10015                10020

Leu Leu Ser Leu Pro Val Thr Thr Ser Pro Ser Val Ser Ser Thr
    10025            10030                10035

Leu Pro Gln Ser Ile Pro Ser Ser Ser Phe Ser Val Thr Ser Leu
    10040            10045                10050

Leu Thr Pro Gly Met Val Lys Thr Thr Asp Thr Ser Thr Glu Pro
    10055            10060                10065

Gly Thr Ser Leu Ser Pro Asn Leu Ser Gly Thr Ser Val Glu Ile
    10070            10075                10080
```

| | | | | | | | | | | | |
|---|---|---|---|---|---|---|---|---|---|---|---|
|Leu|Ala|Ala|Ser|Glu|Val|Thr|Thr|Asp|Thr|Glu|Lys|Ile|His|Pro|
| |10085| | | |10090| | | |10095| | | | | |
|Ser|Ser|Ser|Met|Ala|Val|Thr|Asn|Val|Gly|Thr|Thr|Ser|Ser|Gly|
| |10100| | | |10105| | | |10110| | | | | |
|His|Glu|Leu|Tyr|Ser|Ser|Val|Ser|Ile|His|Ser|Glu|Pro|Ser|Lys|
| |10115| | | |10120| | | |10125| | | | | |
|Ala|Thr|Tyr|Pro|Val|Gly|Thr|Pro|Ser|Ser|Met|Ala|Glu|Thr|Ser|
| |10130| | | |10135| | | |10140| | | | | |
|Ile|Ser|Thr|Ser|Met|Pro|Ala|Asn|Phe|Glu|Thr|Thr|Gly|Phe|Glu|
| |10145| | | |10150| | | |10155| | | | | |
|Ala|Glu|Pro|Phe|Ser|His|Leu|Thr|Ser|Gly|Phe|Arg|Lys|Thr|Asn|
| |10160| | | |10165| | | |10170| | | | | |
|Met|Ser|Leu|Asp|Thr|Ser|Ser|Val|Thr|Pro|Thr|Asn|Thr|Pro|Ser|
| |10175| | | |10180| | | |10185| | | | | |
|Ser|Pro|Gly|Ser|Thr|His|Leu|Leu|Gln|Ser|Ser|Lys|Thr|Asp|Phe|
| |10190| | | |10195| | | |10200| | | | | |
|Thr|Ser|Ser|Ala|Lys|Thr|Ser|Ser|Pro|Asp|Trp|Pro|Pro|Ala|Ser|
| |10205| | | |10210| | | |10215| | | | | |
|Gln|Tyr|Thr|Glu|Ile|Pro|Val|Asp|Ile|Ile|Thr|Pro|Phe|Asn|Ala|
| |10220| | | |10225| | | |10230| | | | | |
|Ser|Pro|Ser|Ile|Thr|Glu|Ser|Thr|Gly|Ile|Thr|Ser|Phe|Pro|Glu|
| |10235| | | |10240| | | |10245| | | | | |
|Ser|Arg|Phe|Thr|Met|Ser|Val|Thr|Glu|Ser|Thr|His|His|Leu|Ser|
| |10250| | | |10255| | | |10260| | | | | |
|Thr|Asp|Leu|Leu|Pro|Ser|Ala|Glu|Thr|Ile|Ser|Thr|Gly|Thr|Val|
| |10265| | | |10270| | | |10275| | | | | |
|Met|Pro|Ser|Leu|Ser|Glu|Ala|Met|Thr|Ser|Phe|Ala|Thr|Thr|Gly|
| |10280| | | |10285| | | |10290| | | | | |
|Val|Pro|Arg|Ala|Ile|Ser|Gly|Ser|Gly|Ser|Pro|Phe|Ser|Arg|Thr|
| |10295| | | |10300| | | |10305| | | | | |
|Glu|Ser|Gly|Pro|Gly|Asp|Ala|Thr|Leu|Ser|Thr|Ile|Ala|Glu|Ser|
| |10310| | | |10315| | | |10320| | | | | |
|Leu|Pro|Ser|Ser|Thr|Pro|Val|Pro|Phe|Ser|Ser|Ser|Thr|Phe|Thr|
| |10325| | | |10330| | | |10335| | | | | |
|Thr|Thr|Asp|Ser|Ser|Thr|Ile|Pro|Ala|Leu|His|Glu|Ile|Thr|Ser|
| |10340| | | |10345| | | |10350| | | | | |
|Ser|Ser|Ala|Thr|Pro|Tyr|Arg|Val|Asp|Thr|Ser|Leu|Gly|Thr|Glu|
| |10355| | | |10360| | | |10365| | | | | |
|Ser|Ser|Thr|Thr|Glu|Gly|Arg|Leu|Val|Met|Val|Ser|Thr|Leu|Asp|
| |10370| | | |10375| | | |10380| | | | | |
|Thr|Ser|Ser|Gln|Pro|Gly|Arg|Thr|Ser|Ser|Ser|Pro|Ile|Leu|Asp|
| |10385| | | |10390| | | |10395| | | | | |
|Thr|Arg|Met|Thr|Glu|Ser|Val|Glu|Leu|Gly|Thr|Val|Thr|Ser|Ala|
| |10400| | | |10405| | | |10410| | | | | |
|Tyr|Gln|Val|Pro|Ser|Leu|Ser|Thr|Arg|Leu|Thr|Arg|Thr|Asp|Gly|
| |10415| | | |10420| | | |10425| | | | | |
|Ile|Met|Glu|His|Ile|Thr|Lys|Ile|Pro|Asn|Glu|Ala|Ala|His|Arg|
| |10430| | | |10435| | | |10440| | | | | |
|Gly|Thr|Ile|Arg|Pro|Val|Lys|Gly|Pro|Gln|Thr|Ser|Thr|Ser|Pro|
| |10445| | | |10450| | | |10455| | | | | |
|Ala|Ser|Pro|Lys|Gly|Leu|His|Thr|Gly|Gly|Thr|Lys|Arg|Met|Glu|
| |10460| | | |10465| | | |10470| | | | | |
|Thr|Thr|Thr|Thr|Ala|Leu|Lys|Thr|Thr|Thr|Thr|Ala|Leu|Lys|Thr|

-continued

```
        10475                10480                10485
Thr Ser Arg Ala Thr Leu Thr  Thr Ser Val Tyr Thr  Pro Thr Leu
        10490                10495                10500
Gly Thr Leu Thr Pro Leu Asn  Ala Ser Met Gln Met  Ala Ser Thr
        10505                10510                10515
Ile Pro Thr Glu Met Met Ile  Thr Thr Pro Tyr Val  Phe Pro Asp
        10520                10525                10530
Val Pro Glu Thr Thr Ser Ser  Leu Ala Thr Ser Leu  Gly Ala Glu
        10535                10540                10545
Thr Ser Thr Ala Leu Pro Arg  Thr Thr Pro Ser Val  Phe Asn Arg
        10550                10555                10560
Glu Ser Glu Thr Thr Ala Ser  Leu Val Ser Arg Ser  Gly Ala Glu
        10565                10570                10575
Arg Ser Pro Val Ile Gln Thr  Leu Asp Val Ser Ser  Ser Glu Pro
        10580                10585                10590
Asp Thr Thr Ala Ser Trp Val  Ile His Pro Ala Glu  Thr Ile Pro
        10595                10600                10605
Thr Val Ser Lys Thr Thr Pro  Asn Phe Phe His Ser  Glu Leu Asp
        10610                10615                10620
Thr Val Ser Ser Thr Ala Thr  Ser His Gly Ala Asp  Val Ser Ser
        10625                10630                10635
Ala Ile Pro Thr Asn Ile Ser  Pro Ser Glu Leu Asp  Ala Leu Thr
        10640                10645                10650
Pro Leu Val Thr Ile Ser Gly  Thr Asp Thr Ser Thr  Thr Phe Pro
        10655                10660                10665
Thr Leu Thr Lys Ser Pro His  Glu Thr Glu Thr Arg  Thr Thr Trp
        10670                10675                10680
Leu Thr His Pro Ala Glu Thr  Ser Ser Thr Ile Pro  Arg Thr Ile
        10685                10690                10695
Pro Asn Phe Ser His His Glu  Ser Asp Ala Thr Pro  Ser Ile Ala
        10700                10705                10710
Thr Ser Pro Gly Ala Glu Thr  Ser Ser Ala Ile Pro  Ile Met Thr
        10715                10720                10725
Val Ser Pro Gly Ala Glu Asp  Leu Val Thr Ser Gln  Val Thr Ser
        10730                10735                10740
Ser Gly Thr Asp Arg Asn Met  Thr Ile Pro Thr Leu  Thr Leu Ser
        10745                10750                10755
Pro Gly Glu Pro Lys Thr Ile  Ala Ser Leu Val Thr  His Pro Glu
        10760                10765                10770
Ala Gln Thr Ser Ser Ala Ile  Pro Thr Ser Thr Ile  Ser Pro Ala
        10775                10780                10785
Val Ser Arg Leu Val Thr Ser  Met Val Thr Ser Leu  Ala Ala Lys
        10790                10795                10800
Thr Ser Thr Thr Asn Arg Ala  Leu Thr Asn Ser Pro  Gly Glu Pro
        10805                10810                10815
Ala Thr Thr Val Ser Leu Val  Thr His Pro Ala Gln  Thr Ser Pro
        10820                10825                10830
Thr Val Pro Trp Thr Thr Ser  Ile Phe Phe His Ser  Lys Ser Asp
        10835                10840                10845
Thr Thr Pro Ser Met Thr Thr  Ser His Gly Ala Glu  Ser Ser Ser
        10850                10855                10860
Ala Val Pro Thr Pro Thr Val  Ser Thr Glu Val Pro  Gly Val Val
        10865                10870                10875
```

```
Thr Pro Leu Val Thr Ser Ser Arg Ala Val Ile Ser Thr Thr Ile
    10880           10885               10890

Pro Ile Leu Thr Leu Ser Pro Gly Glu Pro Glu Thr Thr Pro Ser
    10895           10900               10905

Met Ala Thr Ser His Gly Glu Glu Ala Ser Ser Ala Ile Pro Thr
    10910           10915               10920

Pro Thr Val Ser Pro Gly Val Pro Gly Val Val Thr Ser Leu Val
    10925           10930               10935

Thr Ser Ser Arg Ala Val Thr Ser Thr Thr Ile Pro Ile Leu Thr
    10940           10945               10950

Phe Ser Leu Gly Glu Pro Glu Thr Thr Pro Ser Met Ala Thr Ser
    10955           10960               10965

His Gly Thr Glu Ala Gly Ser Ala Val Pro Thr Val Leu Pro Glu
    10970           10975               10980

Val Pro Gly Met Val Thr Ser Leu Val Ala Ser Ser Arg Ala Val
    10985           10990               10995

Thr Ser Thr Thr Leu Pro Thr Leu Thr Leu Ser Pro Gly Glu Pro
    11000           11005               11010

Glu Thr Thr Pro Ser Met Ala Thr Ser His Gly Ala Glu Ala Ser
    11015           11020               11025

Ser Thr Val Pro Thr Val Ser Pro Glu Val Pro Gly Val Val Thr
    11030           11035               11040

Ser Leu Val Thr Ser Ser Ser Gly Val Asn Ser Thr Ser Ile Pro
    11045           11050               11055

Thr Leu Ile Leu Ser Pro Gly Glu Leu Glu Thr Thr Pro Ser Met
    11060           11065               11070

Ala Thr Ser His Gly Ala Glu Ala Ser Ser Ala Val Pro Thr Pro
    11075           11080               11085

Thr Val Ser Pro Gly Val Ser Gly Val Val Thr Pro Leu Val Thr
    11090           11095               11100

Ser Ser Arg Ala Val Thr Ser Thr Thr Ile Pro Ile Leu Thr Leu
    11105           11110               11115

Ser Ser Ser Glu Pro Glu Thr Thr Pro Ser Met Ala Thr Ser His
    11120           11125               11130

Gly Val Glu Ala Ser Ser Ala Val Leu Thr Val Ser Pro Glu Val
    11135           11140               11145

Pro Gly Met Val Thr Ser Leu Val Thr Ser Ser Arg Ala Val Thr
    11150           11155               11160

Ser Thr Thr Ile Pro Thr Leu Thr Ile Ser Ser Asp Glu Pro Glu
    11165           11170               11175

Thr Thr Thr Ser Leu Val Thr His Ser Glu Ala Lys Met Ile Ser
    11180           11185               11190

Ala Ile Pro Thr Leu Ala Val Ser Pro Thr Val Gln Gly Leu Val
    11195           11200               11205

Thr Ser Leu Val Thr Ser Ser Gly Ser Glu Thr Ser Ala Phe Ser
    11210           11215               11220

Asn Leu Thr Val Ala Ser Ser Gln Pro Glu Thr Ile Asp Ser Trp
    11225           11230               11235

Val Ala His Pro Gly Thr Glu Ala Ser Ser Val Val Pro Thr Leu
    11240           11245               11250

Thr Val Ser Thr Gly Glu Pro Phe Thr Asn Ile Ser Leu Val Thr
    11255           11260               11265
```

```
His Pro Ala Glu Ser Ser Ser     Thr Leu Pro Arg Thr     Thr Ser Arg
    11270               11275                   11280
Phe Ser His Ser Glu Leu Asp     Thr Met Pro Ser Thr     Val Thr Ser
    11285               11290                   11295
Pro Glu Ala Glu Ser Ser Ser     Ala Ile Ser Thr Thr     Ile Ser Pro
    11300               11305                   11310
Gly Ile Pro Gly Val Leu Thr     Ser Leu Val Thr Ser     Ser Gly Arg
    11315               11320                   11325
Asp Ile Ser Ala Thr Phe Pro     Thr Val Pro Glu Ser     Pro His Glu
    11330               11335                   11340
Ser Glu Ala Thr Ala Ser Trp     Val Thr His Pro Ala     Val Thr Ser
    11345               11350                   11355
Thr Thr Val Pro Arg Thr Thr     Pro Asn Tyr Ser His     Ser Glu Pro
    11360               11365                   11370
Asp Thr Thr Pro Ser Ile Ala     Thr Ser Pro Gly Ala     Glu Ala Thr
    11375               11380                   11385
Ser Asp Phe Pro Thr Ile Thr     Val Ser Pro Asp Val     Pro Asp Met
    11390               11395                   11400
Val Thr Ser Gln Val Thr Ser     Ser Gly Thr Asp Thr     Ser Ile Thr
    11405               11410                   11415
Ile Pro Thr Leu Thr Leu Ser     Ser Gly Glu Pro Glu     Thr Thr Thr
    11420               11425                   11430
Ser Phe Ile Thr Tyr Ser Glu     Thr His Thr Ser Ser     Ala Ile Pro
    11435               11440                   11445
Thr Leu Pro Val Ser Pro Gly     Ala Ser Lys Met Leu     Thr Ser Leu
    11450               11455                   11460
Val Ile Ser Ser Gly Thr Asp     Ser Thr Thr Thr Phe     Pro Thr Leu
    11465               11470                   11475
Thr Glu Thr Pro Tyr Glu Pro     Glu Thr Thr Ala Ile     Gln Leu Ile
    11480               11485                   11490
His Pro Ala Glu Thr Asn Thr     Met Val Pro Arg Thr     Thr Pro Lys
    11495               11500                   11505
Phe Ser His Ser Lys Ser Asp     Thr Thr Leu Pro Val     Ala Ile Thr
    11510               11515                   11520
Ser Pro Gly Pro Glu Ala Ser     Ser Ala Val Ser Thr     Thr Thr Ile
    11525               11530                   11535
Ser Pro Asp Met Ser Asp Leu     Val Thr Ser Leu Val     Pro Ser Ser
    11540               11545                   11550
Gly Thr Asp Thr Ser Thr Thr     Phe Pro Thr Leu Ser     Glu Thr Pro
    11555               11560                   11565
Tyr Glu Pro Glu Thr Thr Ala     Thr Trp Leu Thr His     Pro Ala Glu
    11570               11575                   11580
Thr Ser Thr Thr Val Ser Gly     Thr Ile Pro Asn Phe     Ser His Arg
    11585               11590                   11595
Gly Ser Asp Thr Ala Pro Ser     Met Val Thr Ser Pro     Gly Val Asp
    11600               11605                   11610
Thr Arg Ser Gly Val Pro Thr     Thr Thr Ile Pro Pro     Ser Ile Pro
    11615               11620                   11625
Gly Val Val Thr Ser Gln Val     Thr Ser Ser Ala Thr     Asp Thr Ser
    11630               11635                   11640
Thr Ala Ile Pro Thr Leu Thr     Pro Ser Pro Gly Glu     Pro Glu Thr
    11645               11650                   11655
Thr Ala Ser Ser Ala Thr His     Pro Gly Thr Gln Thr     Gly Phe Thr
```

```
                              11660               11665               11670

Val Pro Ile Arg Thr Val Pro Ser Ser Glu Pro Asp Thr Met Ala
                11675               11680               11685

Ser Trp Val Thr His Pro Pro Gln Thr Ser Thr Pro Val Ser Arg
                11690               11695               11700

Thr Thr Ser Ser Phe Ser His Ser Ser Pro Asp Ala Thr Pro Val
                11705               11710               11715

Met Ala Thr Ser Pro Arg Thr Glu Ala Ser Ser Ala Val Leu Thr
                11720               11725               11730

Thr Ile Ser Pro Gly Ala Pro Glu Met Val Thr Ser Gln Ile Thr
                11735               11740               11745

Ser Ser Gly Ala Ala Thr Ser Thr Thr Val Pro Thr Leu Thr His
                11750               11755               11760

Ser Pro Gly Met Pro Glu Thr Thr Ala Leu Leu Ser Thr His Pro
                11765               11770               11775

Arg Thr Glu Thr Ser Lys Thr Phe Pro Ala Ser Thr Val Phe Pro
                11780               11785               11790

Gln Val Ser Glu Thr Thr Ala Ser Leu Thr Ile Arg Pro Gly Ala
                11795               11800               11805

Glu Thr Ser Thr Ala Leu Pro Thr Gln Thr Thr Ser Ser Leu Phe
                11810               11815               11820

Thr Leu Leu Val Thr Gly Thr Ser Arg Val Asp Leu Ser Pro Thr
                11825               11830               11835

Ala Ser Pro Gly Val Ser Ala Lys Thr Ala Pro Leu Ser Thr His
                11840               11845               11850

Pro Gly Thr Glu Thr Ser Thr Met Ile Pro Thr Ser Thr Leu Ser
                11855               11860               11865

Leu Gly Leu Leu Glu Thr Thr Gly Leu Leu Ala Thr Ser Ser Ser
                11870               11875               11880

Ala Glu Thr Ser Thr Ser Thr Leu Thr Leu Thr Val Ser Pro Ala
                11885               11890               11895

Val Ser Gly Leu Ser Ser Ala Ser Ile Thr Thr Asp Lys Pro Gln
                11900               11905               11910

Thr Val Thr Ser Trp Asn Thr Glu Thr Ser Pro Ser Val Thr Ser
                11915               11920               11925

Val Gly Pro Pro Glu Phe Ser Arg Thr Val Thr Gly Thr Thr Met
                11930               11935               11940

Thr Leu Ile Pro Ser Glu Met Pro Thr Pro Pro Lys Thr Ser His
                11945               11950               11955

Gly Glu Gly Val Ser Pro Thr Thr Ile Leu Arg Thr Thr Met Val
                11960               11965               11970

Glu Ala Thr Asn Leu Ala Thr Thr Gly Ser Ser Pro Thr Val Ala
                11975               11980               11985

Lys Thr Thr Thr Thr Phe Asn Thr Leu Ala Gly Ser Leu Phe Thr
                11990               11995               12000

Pro Leu Thr Thr Pro Gly Met Ser Thr Leu Ala Ser Glu Ser Val
                12005               12010               12015

Thr Ser Arg Thr Ser Tyr Asn His Arg Ser Trp Ile Ser Thr Thr
                12020               12025               12030

Ser Ser Tyr Asn Arg Arg Tyr Trp Thr Pro Ala Thr Ser Thr Pro
                12035               12040               12045

Val Thr Ser Thr Phe Ser Pro Gly Ile Ser Thr Ser Ser Ile Pro
                12050               12055               12060
```

-continued

```
Ser Ser Thr Ala Ala Thr Val Pro Phe Met Val Pro Phe Thr Leu
12065               12070               12075

Asn Phe Thr Ile Thr Asn Leu Gln Tyr Glu Glu Asp Met Arg His
12080               12085               12090

Pro Gly Ser Arg Lys Phe Asn Ala Thr Glu Arg Glu Leu Gln Gly
12095               12100               12105

Leu Leu Lys Pro Leu Phe Arg Asn Ser Ser Leu Glu Tyr Leu Tyr
12110               12115               12120

Ser Gly Cys Arg Leu Ala Ser Leu Arg Pro Glu Lys Asp Ser Ser
12125               12130               12135

Ala Thr Ala Val Asp Ala Ile Cys Thr His Arg Pro Asp Pro Glu
12140               12145               12150

Asp Leu Gly Leu Asp Arg Glu Arg Leu Tyr Trp Glu Leu Ser Asn
12155               12160               12165

Leu Thr Asn Gly Ile Gln Glu Leu Gly Pro Tyr Thr Leu Asp Arg
12170               12175               12180

Asn Ser Leu Tyr Val Asn Gly Phe Thr His Arg Ser Ser Met Pro
12185               12190               12195

Thr Thr Ser Thr Pro Gly Thr Ser Thr Val Asp Val Gly Thr Ser
12200               12205               12210

Gly Thr Pro Ser Ser Ser Pro Ser Pro Thr Thr Ala Gly Pro Leu
12215               12220               12225

Leu Met Pro Phe Thr Leu Asn Phe Thr Ile Thr Asn Leu Gln Tyr
12230               12235               12240

Glu Glu Asp Met Arg Arg Thr Gly Ser Arg Lys Phe Asn Thr Met
12245               12250               12255

Glu Ser Val Leu Gln Gly Leu Leu Lys Pro Leu Phe Lys Asn Thr
12260               12265               12270

Ser Val Gly Pro Leu Tyr Ser Gly Cys Arg Leu Thr Leu Leu Arg
12275               12280               12285

Pro Glu Lys Asp Gly Ala Ala Thr Gly Val Asp Ala Ile Cys Thr
12290               12295               12300

His Arg Leu Asp Pro Lys Ser Pro Gly Leu Asn Arg Glu Gln Leu
12305               12310               12315

Tyr Trp Glu Leu Ser Lys Leu Thr Asn Asp Ile Glu Glu Leu Gly
12320               12325               12330

Pro Tyr Thr Leu Asp Arg Asn Ser Leu Tyr Val Asn Gly Phe Thr
12335               12340               12345

His Gln Ser Ser Val Ser Thr Thr Ser Thr Pro Gly Thr Ser Thr
12350               12355               12360

Val Asp Leu Arg Thr Ser Gly Thr Pro Ser Ser Leu Ser Ser Pro
12365               12370               12375

Thr Ile Met Ala Ala Gly Pro Leu Leu Val Pro Phe Thr Leu Asn
12380               12385               12390

Phe Thr Ile Thr Asn Leu Gln Tyr Gly Glu Asp Met Gly His Pro
12395               12400               12405

Gly Ser Arg Lys Phe Asn Thr Thr Glu Arg Val Leu Gln Gly Leu
12410               12415               12420

Leu Gly Pro Ile Phe Lys Asn Thr Ser Val Gly Pro Leu Tyr Ser
12425               12430               12435

Gly Cys Arg Leu Thr Ser Leu Arg Ser Glu Lys Asp Gly Ala Ala
12440               12445               12450
```

```
Thr Gly Val Asp Ala Ile Cys    Ile His His Leu Asp    Pro Lys Ser
    12455               12460                12465

Pro Gly Leu Asn Arg Glu Arg    Leu Tyr Trp Glu Leu    Ser Gln Leu
    12470               12475                12480

Thr Asn Gly Ile Lys Glu Leu    Gly Pro Tyr Thr Leu    Asp Arg Asn
    12485               12490                12495

Ser Leu Tyr Val Asn Gly Phe    Thr His Arg Thr Ser    Val Pro Thr
    12500               12505                12510

Ser Ser Thr Pro Gly Thr Ser    Thr Val Asp Leu Gly    Thr Ser Gly
    12515               12520                12525

Thr Pro Phe Ser Leu Pro Ser    Pro Ala Thr Ala Gly    Pro Leu Leu
    12530               12535                12540

Val Leu Phe Thr Leu Asn Phe    Thr Ile Thr Asn Leu    Lys Tyr Glu
    12545               12550                12555

Glu Asp Met His Arg Pro Gly    Ser Arg Lys Phe Asn    Thr Thr Glu
    12560               12565                12570

Arg Val Leu Gln Thr Leu Leu    Gly Pro Met Phe Lys    Asn Thr Ser
    12575               12580                12585

Val Gly Leu Leu Tyr Ser Gly    Cys Arg Leu Thr Leu    Leu Arg Ser
    12590               12595                12600

Glu Lys Asp Gly Ala Ala Thr    Gly Val Asp Ala Ile    Cys Thr His
    12605               12610                12615

Arg Leu Asp Pro Lys Ser Pro    Gly Val Asp Arg Glu    Gln Leu Tyr
    12620               12625                12630

Trp Glu Leu Ser Gln Leu Thr    Asn Gly Ile Lys Glu    Leu Gly Pro
    12635               12640                12645

Tyr Thr Leu Asp Arg Asn Ser    Leu Tyr Val Asn Gly    Phe Thr His
    12650               12655                12660

Trp Ile Pro Val Pro Thr Ser    Ser Thr Pro Gly Thr    Ser Thr Val
    12665               12670                12675

Asp Leu Gly Ser Gly Thr Pro    Ser Ser Leu Pro Ser    Pro Thr Thr
    12680               12685                12690

Ala Gly Pro Leu Leu Val Pro    Phe Thr Leu Asn Phe    Thr Ile Thr
    12695               12700                12705

Asn Leu Lys Tyr Glu Glu Asp    Met His Cys Pro Gly    Ser Arg Lys
    12710               12715                12720

Phe Asn Thr Thr Glu Arg Val    Leu Gln Ser Leu Leu    Gly Pro Met
    12725               12730                12735

Phe Lys Asn Thr Ser Val Gly    Pro Leu Tyr Ser Gly    Cys Arg Leu
    12740               12745                12750

Thr Leu Leu Arg Ser Glu Lys    Asp Gly Ala Ala Thr    Gly Val Asp
    12755               12760                12765

Ala Ile Cys Thr His Arg Leu    Asp Pro Lys Ser Pro    Gly Val Asp
    12770               12775                12780

Arg Glu Gln Leu Tyr Trp Glu    Leu Ser Gln Leu Thr    Asn Gly Ile
    12785               12790                12795

Lys Glu Leu Gly Pro Tyr Thr    Leu Asp Arg Asn Ser    Leu Tyr Val
    12800               12805                12810

Asn Gly Phe Thr His Gln Thr    Ser Ala Pro Asn Thr    Ser Thr Pro
    12815               12820                12825

Gly Thr Ser Thr Val Asp Leu    Gly Thr Ser Gly Thr    Pro Ser Ser
    12830               12835                12840

Leu Pro Ser Pro Thr Ser Ala    Gly Pro Leu Leu Val    Pro Phe Thr
```

```
             12845               12850               12855

Leu Asn Phe Thr Ile Thr Asn Leu Gln Tyr Glu Glu Asp Met His
        12860               12865               12870

His Pro Gly Ser Arg Lys Phe Asn Thr Thr Glu Arg Val Leu Gln
        12875               12880               12885

Gly Leu Leu Gly Pro Met Phe Lys Asn Thr Ser Val Gly Leu Leu
        12890               12895               12900

Tyr Ser Gly Cys Arg Leu Thr Leu Leu Arg Pro Glu Lys Asn Gly
        12905               12910               12915

Ala Ala Thr Gly Met Asp Ala Ile Cys Ser His Arg Leu Asp Pro
        12920               12925               12930

Lys Ser Pro Gly Leu Asn Arg Glu Gln Leu Tyr Trp Glu Leu Ser
        12935               12940               12945

Gln Leu Thr His Gly Ile Lys Glu Leu Gly Pro Tyr Thr Leu Asp
        12950               12955               12960

Arg Asn Ser Leu Tyr Val Asn Gly Phe Thr His Arg Ser Ser Val
        12965               12970               12975

Ala Pro Thr Ser Thr Pro Gly Thr Ser Thr Val Asp Leu Gly Thr
        12980               12985               12990

Ser Gly Thr Pro Ser Ser Leu Pro Ser Pro Thr Thr Ala Val Pro
        12995               13000               13005

Leu Leu Val Pro Phe Thr Leu Asn Phe Thr Ile Thr Asn Leu Gln
        13010               13015               13020

Tyr Gly Glu Asp Met Arg His Pro Gly Ser Arg Lys Phe Asn Thr
        13025               13030               13035

Thr Glu Arg Val Leu Gln Gly Leu Leu Gly Pro Leu Phe Lys Asn
        13040               13045               13050

Ser Ser Val Gly Pro Leu Tyr Ser Gly Cys Arg Leu Ile Ser Leu
        13055               13060               13065

Arg Ser Glu Lys Asp Gly Ala Ala Thr Gly Val Asp Ala Ile Cys
        13070               13075               13080

Thr His His Leu Asn Pro Gln Ser Pro Gly Leu Asp Arg Glu Gln
        13085               13090               13095

Leu Tyr Trp Gln Leu Ser Gln Met Thr Asn Gly Ile Lys Glu Leu
        13100               13105               13110

Gly Pro Tyr Thr Leu Asp Arg Asn Ser Leu Tyr Val Asn Gly Phe
        13115               13120               13125

Thr His Arg Ser Ser Gly Leu Thr Thr Ser Thr Pro Trp Thr Ser
        13130               13135               13140

Thr Val Asp Leu Gly Thr Ser Gly Thr Pro Ser Pro Val Pro Ser
        13145               13150               13155

Pro Thr Thr Thr Gly Pro Leu Leu Val Pro Phe Thr Leu Asn Phe
        13160               13165               13170

Thr Ile Thr Asn Leu Gln Tyr Glu Glu Asn Met Gly His Pro Gly
        13175               13180               13185

Ser Arg Lys Phe Asn Ile Thr Glu Ser Val Leu Gln Gly Leu Leu
        13190               13195               13200

Lys Pro Leu Phe Lys Ser Thr Ser Val Gly Pro Leu Tyr Ser Gly
        13205               13210               13215

Cys Arg Leu Thr Leu Leu Arg Pro Glu Lys Asp Gly Val Ala Thr
        13220               13225               13230

Arg Val Asp Ala Ile Cys Thr His Arg Pro Asp Pro Lys Ile Pro
        13235               13240               13245
```

| | | | | | | | | | | |
|---|---|---|---|---|---|---|---|---|---|---|
| Gly | Leu | Asp | Arg | Gln | Gln | Leu | Tyr | Trp | Glu | Leu | Ser | Gln | Leu | Thr |
| | 13250 | | | | 13255 | | | | | 13260 | | | | |
| His | Ser | Ile | Thr | Glu | Leu | Gly | Pro | Tyr | Thr | Leu | Asp | Arg | Asp | Ser |
| | 13265 | | | | 13270 | | | | | 13275 | | | | |
| Leu | Tyr | Val | Asn | Gly | Phe | Thr | Gln | Arg | Ser | Ser | Val | Pro | Thr | Thr |
| | 13280 | | | | 13285 | | | | | 13290 | | | | |
| Ser | Thr | Pro | Gly | Thr | Phe | Thr | Val | Gln | Pro | Glu | Thr | Ser | Glu | Thr |
| | 13295 | | | | 13300 | | | | | 13305 | | | | |
| Pro | Ser | Ser | Leu | Pro | Gly | Pro | Thr | Ala | Thr | Gly | Pro | Val | Leu | Leu |
| | 13310 | | | | 13315 | | | | | 13320 | | | | |
| Pro | Phe | Thr | Leu | Asn | Phe | Thr | Ile | Thr | Asn | Leu | Gln | Tyr | Glu | Glu |
| | 13325 | | | | 13330 | | | | | 13335 | | | | |
| Asp | Met | Arg | Arg | Pro | Gly | Ser | Arg | Lys | Phe | Asn | Thr | Thr | Glu | Arg |
| | 13340 | | | | 13345 | | | | | 13350 | | | | |
| Val | Leu | Gln | Gly | Leu | Leu | Met | Pro | Leu | Phe | Lys | Asn | Thr | Ser | Val |
| | 13355 | | | | 13360 | | | | | 13365 | | | | |
| Ser | Ser | Leu | Tyr | Ser | Gly | Cys | Arg | Leu | Thr | Leu | Leu | Arg | Pro | Glu |
| | 13370 | | | | 13375 | | | | | 13380 | | | | |
| Lys | Asp | Gly | Ala | Ala | Thr | Arg | Val | Asp | Ala | Val | Cys | Thr | His | Arg |
| | 13385 | | | | 13390 | | | | | 13395 | | | | |
| Pro | Asp | Pro | Lys | Ser | Pro | Gly | Leu | Asp | Arg | Glu | Arg | Leu | Tyr | Trp |
| | 13400 | | | | 13405 | | | | | 13410 | | | | |
| Lys | Leu | Ser | Gln | Leu | Thr | His | Gly | Ile | Thr | Glu | Leu | Gly | Pro | Tyr |
| | 13415 | | | | 13420 | | | | | 13425 | | | | |
| Thr | Leu | Asp | Arg | His | Ser | Leu | Tyr | Val | Asn | Gly | Phe | Thr | His | Gln |
| | 13430 | | | | 13435 | | | | | 13440 | | | | |
| Ser | Ser | Met | Thr | Thr | Thr | Arg | Thr | Pro | Asp | Thr | Ser | Thr | Met | His |
| | 13445 | | | | 13450 | | | | | 13455 | | | | |
| Leu | Ala | Thr | Ser | Arg | Thr | Pro | Ala | Ser | Leu | Ser | Gly | Pro | Met | Thr |
| | 13460 | | | | 13465 | | | | | 13470 | | | | |
| Ala | Ser | Pro | Leu | Leu | Val | Leu | Phe | Thr | Ile | Asn | Phe | Thr | Ile | Thr |
| | 13475 | | | | 13480 | | | | | 13485 | | | | |
| Asn | Leu | Arg | Tyr | Glu | Glu | Asn | Met | His | His | Pro | Gly | Ser | Arg | Lys |
| | 13490 | | | | 13495 | | | | | 13500 | | | | |
| Phe | Asn | Thr | Thr | Glu | Arg | Val | Leu | Gln | Gly | Leu | Leu | Arg | Pro | Val |
| | 13505 | | | | 13510 | | | | | 13515 | | | | |
| Phe | Lys | Asn | Thr | Ser | Val | Gly | Pro | Leu | Tyr | Ser | Gly | Cys | Arg | Leu |
| | 13520 | | | | 13525 | | | | | 13530 | | | | |
| Thr | Leu | Leu | Arg | Pro | Lys | Lys | Asp | Gly | Ala | Ala | Thr | Lys | Val | Asp |
| | 13535 | | | | 13540 | | | | | 13545 | | | | |
| Ala | Ile | Cys | Thr | Tyr | Arg | Pro | Asp | Pro | Lys | Ser | Pro | Gly | Leu | Asp |
| | 13550 | | | | 13555 | | | | | 13560 | | | | |
| Arg | Glu | Gln | Leu | Tyr | Trp | Glu | Leu | Ser | Gln | Leu | Thr | His | Ser | Ile |
| | 13565 | | | | 13570 | | | | | 13575 | | | | |
| Thr | Glu | Leu | Gly | Pro | Tyr | Thr | Leu | Asp | Arg | Asp | Ser | Leu | Tyr | Val |
| | 13580 | | | | 13585 | | | | | 13590 | | | | |
| Asn | Gly | Phe | Thr | Gln | Arg | Ser | Ser | Val | Pro | Thr | Thr | Ser | Ile | Pro |
| | 13595 | | | | 13600 | | | | | 13605 | | | | |
| Gly | Thr | Pro | Thr | Val | Asp | Leu | Gly | Thr | Ser | Gly | Thr | Pro | Val | Ser |
| | 13610 | | | | 13615 | | | | | 13620 | | | | |
| Lys | Pro | Gly | Pro | Ser | Ala | Ala | Ser | Pro | Leu | Leu | Val | Leu | Phe | Thr |
| | 13625 | | | | 13630 | | | | | 13635 | | | | |

```
Leu Asn  Phe Thr Ile Thr Asn  Leu Arg Tyr Glu Glu  Asn Met Gln
    13640            13645                13650

His Pro  Gly Ser Arg Lys Phe  Asn Thr Thr Glu Arg  Val Leu Gln
    13655            13660                13665

Gly Leu  Leu Arg Ser Leu Phe  Lys Ser Thr Ser Val  Gly Pro Leu
    13670            13675                13680

Tyr Ser  Gly Cys Arg Leu Thr  Leu Leu Arg Pro Glu  Lys Asp Gly
    13685            13690                13695

Thr Ala  Thr Gly Val Asp Ala  Ile Cys Thr His His  Pro Asp Pro
    13700            13705                13710

Lys Ser  Pro Arg Leu Asp Arg  Glu Gln Leu Tyr Trp  Glu Leu Ser
    13715            13720                13725

Gln Leu  Thr His Asn Ile Thr  Glu Leu Gly Pro Tyr  Ala Leu Asp
    13730            13735                13740

Asn Asp  Ser Leu Phe Val Asn  Gly Phe Thr His Arg  Ser Ser Val
    13745            13750                13755

Ser Thr  Thr Ser Thr Pro Gly  Thr Pro Thr Val Tyr  Leu Gly Ala
    13760            13765                13770

Ser Lys  Thr Pro Ala Ser Ile  Phe Gly Pro Ser Ala  Ala Ser His
    13775            13780                13785

Leu Leu  Ile Leu Phe Thr Leu  Asn Phe Thr Ile Thr  Asn Leu Arg
    13790            13795                13800

Tyr Glu  Glu Asn Met Trp Pro  Gly Ser Arg Lys Phe  Asn Thr Thr
    13805            13810                13815

Glu Arg  Val Leu Gln Gly Leu  Leu Arg Pro Leu Phe  Lys Asn Thr
    13820            13825                13830

Ser Val  Gly Pro Leu Tyr Ser  Gly Cys Arg Leu Thr  Leu Leu Arg
    13835            13840                13845

Pro Glu  Lys Asp Gly Glu Ala  Thr Gly Val Asp Ala  Ile Cys Thr
    13850            13855                13860

His Arg  Pro Asp Pro Thr Gly  Pro Gly Leu Asp Arg  Glu Gln Leu
    13865            13870                13875

Tyr Leu  Glu Leu Ser Gln Leu  Thr His Ser Ile Thr  Glu Leu Gly
    13880            13885                13890

Pro Tyr  Thr Leu Asp Arg Asp  Ser Leu Tyr Val Asn  Gly Phe Thr
    13895            13900                13905

His Arg  Ser Ser Val Pro Thr  Thr Ser Thr Gly Val  Val Ser Glu
    13910            13915                13920

Glu Pro  Phe Thr Leu Asn Phe  Thr Ile Asn Asn Leu  Arg Tyr Met
    13925            13930                13935

Ala Asp  Met Gly Gln Pro Gly  Ser Leu Lys Phe Asn  Ile Thr Asp
    13940            13945                13950

Asn Val  Met Gln His Leu Leu  Ser Pro Leu Phe Gln  Arg Ser Ser
    13955            13960                13965

Leu Gly  Ala Arg Tyr Thr Gly  Cys Arg Val Ile Ala  Leu Arg Ser
    13970            13975                13980

Val Lys  Asn Gly Ala Glu Thr  Arg Val Asp Leu Leu  Cys Thr Tyr
    13985            13990                13995

Leu Gln  Pro Leu Ser Gly Pro  Gly Leu Pro Ile Lys  Gln Val Phe
    14000            14005                14010

His Glu  Leu Ser Gln Gln Thr  His Gly Ile Thr Arg  Leu Gly Pro
    14015            14020                14025

Tyr Ser  Leu Asp Lys Asp Ser  Leu Tyr Leu Asn Gly  Tyr Asn Glu
```

|  |  |  |  |  |  |  |  |  |  |
|---|---|---|---|---|---|---|---|---|---|
| 14030 | | | 14035 | | | 14040 | | | |
| Pro | Gly | Pro | Asp | Glu | Pro | Pro | Thr | Thr | Pro | Lys | Pro | Ala | Thr | Thr |
| | | 14045 | | | | 14050 | | | | 14055 |

```
              14030               14035               14040
Pro Gly Pro Asp Glu Pro     Thr Thr Pro Lys Pro     Ala Thr Thr
          14045                   14050                   14055
Phe Leu Pro Pro Leu Ser Glu     Ala Thr Thr Ala Met     Gly Tyr His
          14060                   14065                   14070
Leu Lys Thr Leu Thr Leu Asn     Phe Thr Ile Ser Asn     Leu Gln Tyr
          14075                   14080                   14085
Ser Pro Asp Met Gly Lys Gly     Ser Ala Thr Phe Asn     Ser Thr Glu
          14090                   14095                   14100
Gly Val Leu Gln His Leu Leu     Arg Pro Leu Phe Gln     Lys Ser Ser
          14105                   14110                   14115
Met Gly Pro Phe Tyr Leu Gly     Cys Gln Leu Ile Ser     Leu Arg Pro
          14120                   14125                   14130
Glu Lys Asp Gly Ala Ala Thr     Gly Val Asp Thr Thr     Cys Thr Tyr
          14135                   14140                   14145
His Pro Asp Pro Val Gly Pro     Gly Leu Asp Ile Gln     Gln Leu Tyr
          14150                   14155                   14160
Trp Glu Leu Ser Gln Leu Thr     His Gly Val Thr Gln     Leu Gly Phe
          14165                   14170                   14175
Tyr Val Leu Asp Arg Asp Ser     Leu Phe Ile Asn Gly     Tyr Ala Pro
          14180                   14185                   14190
Gln Asn Leu Ser Ile Arg Gly     Glu Tyr Gln Ile Asn     Phe His Ile
          14195                   14200                   14205
Val Asn Trp Asn Leu Ser Asn     Pro Asp Pro Thr Ser     Ser Glu Tyr
          14210                   14215                   14220
Ile Thr Leu Leu Arg Asp Ile     Gln Asp Lys Val Thr     Thr Leu Tyr
          14225                   14230                   14235
Lys Gly Ser Gln Leu His Asp     Thr Phe Arg Phe Cys     Leu Val Thr
          14240                   14245                   14250
Asn Leu Thr Met Asp Ser Val     Leu Val Thr Val Lys     Ala Leu Phe
          14255                   14260                   14265
Ser Ser Asn Leu Asp Pro Ser     Leu Val Glu Gln Val     Phe Leu Asp
          14270                   14275                   14280
Lys Thr Leu Asn Ala Ser Phe     His Trp Leu Gly Ser     Thr Tyr Gln
          14285                   14290                   14295
Leu Val Asp Ile His Val Thr     Glu Met Glu Ser Ser     Val Tyr Gln
          14300                   14305                   14310
Pro Thr Ser Ser Ser Ser Thr     Gln His Phe Tyr Leu     Asn Phe Thr
          14315                   14320                   14325
Ile Thr Asn Leu Pro Tyr Ser     Gln Asp Lys Ala Gln     Pro Gly Thr
          14330                   14335                   14340
Thr Asn Tyr Gln Arg Asn Lys     Arg Asn Ile Glu Asp     Ala Leu Asn
          14345                   14350                   14355
Gln Leu Phe Arg Asn Ser Ser     Ile Lys Ser Tyr Phe     Ser Asp Cys
          14360                   14365                   14370
Gln Val Ser Thr Phe Arg Ser     Val Pro Asn Arg His     His Thr Gly
          14375                   14380                   14385
Val Asp Ser Leu Cys Asn Phe     Ser Pro Leu Ala Arg     Arg Val Asp
          14390                   14395                   14400
Arg Val Ala Ile Tyr Glu Glu     Phe Leu Arg Met Thr     Arg Asn Gly
          14405                   14410                   14415
Thr Gln Leu Gln Asn Phe Thr     Leu Asp Arg Ser Ser     Val Leu Val
          14420                   14425                   14430
```

```
Asp Gly  Tyr Ser Pro Asn Arg  Asn Glu Pro Leu Thr  Gly Asn Ser
    14435            14440                14445

Asp Leu  Pro Phe Trp Ala Val  Ile Leu Ile Gly Leu  Ala Gly Leu
    14450            14455                14460

Leu Gly  Val Ile Thr Cys Leu  Ile Cys Gly Val Leu  Val Thr Thr
    14465            14470                14475

Arg Arg  Arg Lys Lys Glu Gly  Glu Tyr Asn Val Gln  Gln Gln Cys
    14480            14485                14490

Pro Gly  Tyr Tyr Gln Ser His  Leu Asp Leu Glu Asp  Leu Gln
    14495            14500                14505

<210> SEQ ID NO 58
<211> LENGTH: 630
<212> TYPE: PRT
<213> ORGANISM: Homo sapiens

<400> SEQUENCE: 58

Met Ala Leu Pro Thr Ala Arg Pro Leu Leu Gly Ser Cys Gly Thr Pro
 1               5                  10                  15

Ala Leu Gly Ser Leu Leu Phe Leu Leu Phe Ser Leu Gly Trp Val Gln
             20                  25                  30

Pro Ser Arg Thr Leu Ala Gly Glu Thr Gly Gln Glu Ala Ala Pro Leu
         35                  40                  45

Asp Gly Val Leu Ala Asn Pro Pro Asn Ile Ser Ser Leu Ser Pro Arg
     50                  55                  60

Gln Leu Leu Gly Phe Pro Cys Ala Glu Val Ser Gly Leu Ser Thr Glu
 65                  70                  75                  80

Arg Val Arg Glu Leu Ala Val Ala Leu Ala Gln Lys Asn Val Lys Leu
                 85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
```

```
                290                 295                 300
Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
        370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
                420                 425                 430

Leu Asp Lys Asp Thr Leu Asp Thr Leu Thr Ala Phe Tyr Pro Gly Tyr
            435                 440                 445

Leu Cys Ser Leu Ser Pro Glu Leu Ser Ser Val Pro Pro Ser Ser
        450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
                500                 505                 510

Thr Glu Asp Leu Lys Ala Leu Ser Gln Gln Asn Val Ser Met Asp Leu
            515                 520                 525

Ala Thr Phe Met Lys Leu Arg Thr Asp Ala Val Leu Pro Leu Thr Val
        530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
                580                 585                 590

Gly Tyr Leu Val Leu Asp Leu Ser Met Gln Glu Ala Leu Ser Gly Thr
            595                 600                 605

Pro Cys Leu Leu Gly Pro Gly Pro Val Leu Thr Val Leu Ala Leu Leu
        610                 615                 620

Leu Ala Ser Thr Leu Ala
625                 630

<210> SEQ ID NO 59
<211> LENGTH: 622
<212> TYPE: PRT
<213> ORGANISM: Homo sapiens

<400> SEQUENCE: 59

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30
```

```
Pro Ser Arg Thr Leu Ala Gly Glu Thr Gly Gln Glu Ala Ala Pro Leu
         35                  40                  45

Asp Gly Val Leu Ala Asn Pro Asn Ile Ser Ser Leu Ser Pro Arg
 50                  55                  60

Gln Leu Leu Gly Phe Pro Cys Ala Glu Val Ser Gly Leu Ser Thr Glu
 65                  70                  75                  80

Arg Val Arg Glu Leu Ala Val Ala Leu Ala Gln Lys Asn Val Lys Leu
                 85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
```

```
            450                 455                 460
Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
            515                 520                 525

Asp Ala Val Leu Pro Leu Thr Val Ala Glu Val Gln Lys Leu Leu Gly
        530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
            595                 600                 605

Val Leu Thr Val Leu Ala Leu Leu Ala Ser Thr Leu Ala
610                 615                 620

<210> SEQ ID NO 60
<211> LENGTH: 300
<212> TYPE: PRT
<213> ORGANISM: Homo sapiens

<400> SEQUENCE: 60

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205
```

```
Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Asp Lys His Leu Lys Phe Arg Ile
            275                 280                 285

Ser His Glu Leu Asp Ser Ala Ser Ser Glu Val Asn
    290                 295                 300

<210> SEQ ID NO 61
<211> LENGTH: 314
<212> TYPE: PRT
<213> ORGANISM: Homo sapiens

<400> SEQUENCE: 61

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285
```

```
Pro Lys Ser Lys Glu Glu Asp Lys His Leu Lys Phe Arg Ile Ser His
    290                 295                 300

Glu Leu Asp Ser Ala Ser Ser Glu Val Asn
305                 310
```

<210> SEQ ID NO 62
<211> LENGTH: 287
<212> TYPE: PRT
<213> ORGANISM: Homo sapiens

<400> SEQUENCE: 62

```
Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Asn
            20                  25                  30

Ala Val Ser Ser Glu Glu Thr Asn Asp Phe Lys Gln Glu Thr Leu Pro
        35                  40                  45

Ser Lys Ser Asn Glu Ser His Asp His Met Asp Asp Met Asp Asp Glu
    50                  55                  60

Asp Asp Asp Asp His Val Asp Ser Gln Asp Ser Ile Asp Ser Asn Asp
65                  70                  75                  80

Ser Asp Asp Val Asp Asp Thr Asp Asp Ser His Gln Ser Asp Glu Ser
                85                  90                  95

His His Ser Asp Glu Ser Asp Glu Leu Val Thr Asp Phe Pro Thr Asp
            100                 105                 110

Leu Pro Ala Thr Glu Val Phe Thr Pro Val Val Pro Thr Val Asp Thr
        115                 120                 125

Tyr Asp Gly Arg Gly Asp Ser Val Val Tyr Gly Leu Arg Ser Lys Ser
    130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
                165                 170                 175

Ala Ile Pro Val Ala Gln Asp Leu Asn Ala Pro Ser Asp Trp Asp Ser
            180                 185                 190

Arg Gly Lys Asp Ser Tyr Glu Thr Ser Gln Leu Asp Asp Gln Ser Ala
        195                 200                 205

Glu Thr His Ser His Lys Gln Ser Arg Leu Tyr Lys Arg Lys Ala Asn
    210                 215                 220

Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
                245                 250                 255

Met Leu Val Val Asp Pro Lys Ser Lys Glu Glu Asp Lys His Leu Lys
            260                 265                 270

Phe Arg Ile Ser His Glu Leu Asp Ser Ala Ser Ser Glu Val Asn
        275                 280                 285
```

<210> SEQ ID NO 63
<211> LENGTH: 411
<212> TYPE: PRT
<213> ORGANISM: Homo sapiens

<400> SEQUENCE: 63

```
Met Val Cys Phe Arg Leu Phe Pro Val Pro Gly Ser Gly Leu Val Leu
1               5                   10                  15
```

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
                100                 105                 110

Ser Val Ser Phe Ser Tyr Asn Thr Gly Asp Asn Thr Thr Phe Pro Asp
                115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
                180                 185                 190

Lys Thr Ser Thr Val Ala Pro Thr Ile His Thr Thr Val Pro Ser Pro
                195                 200                 205

Thr Thr Thr Pro Thr Pro Lys Glu Lys Pro Glu Ala Gly Thr Tyr Ser
        210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
                260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
                340                 345                 350

Gln Pro Phe Asn Val Thr Gln Gly Lys Tyr Ser Thr Ala Glu Glu Cys
        355                 360                 365

Ser Ala Asp Ser Asp Leu Asn Phe Leu Ile Pro Val Ala Gly Val
    370                 375                 380

Ala Leu Gly Phe Leu Ile Ile Val Val Phe Ile Ser Tyr Met Ile Gly
385                 390                 395                 400

Arg Arg Lys Ser Arg Thr Gly Tyr Gln Ser Val
                405                 410

<210> SEQ ID NO 64
<211> LENGTH: 410

<212> TYPE: PRT
<213> ORGANISM: Homo sapiens

<400> SEQUENCE: 64

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400
```

-continued

```
Lys His His His Ala Gly Tyr Glu Gln Phe
            405                 410

<210> SEQ ID NO 65
<211> LENGTH: 410
<212> TYPE: PRT
<213> ORGANISM: Homo sapiens

<400> SEQUENCE: 65

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
            35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
            115                 120                 125

Ala Glu Asp Lys Gly Ile Leu Thr Val Asp Leu Leu Ala Ile Arg
        130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
```

```
              355                 360                 365
Ser Leu Asp Asp Asp Thr Ile Leu Ile Pro Ile Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410

<210> SEQ ID NO 66
<211> LENGTH: 262
<212> TYPE: PRT
<213> ORGANISM: Homo sapiens

<400> SEQUENCE: 66

Met Trp Phe Leu Val Leu Cys Leu Ala Leu Ser Leu Gly Gly Thr Gly
1               5                   10                  15

Ala Ala Pro Pro Ile Gln Ser Arg Ile Val Gly Gly Trp Glu Cys Glu
                20                  25                  30

Gln His Ser Gln Pro Trp Gln Ala Ala Leu Tyr His Phe Ser Thr Phe
            35                  40                  45

Gln Cys Gly Gly Ile Leu Val His Arg Gln Trp Val Leu Thr Ala Ala
        50                  55                  60

His Cys Ile Ser Asp Asn Tyr Gln Leu Trp Leu Gly Arg His Asn Leu
65                  70                  75                  80

Phe Asp Asp Glu Asn Thr Ala Gln Phe Val His Val Ser Glu Ser Phe
                85                  90                  95

Pro His Pro Gly Phe Asn Met Ser Leu Leu Glu Asn His Thr Arg Gln
                100                 105                 110

Ala Asp Glu Asp Tyr Ser His Asp Leu Met Leu Leu Arg Leu Thr Glu
            115                 120                 125

Pro Ala Asp Thr Ile Thr Asp Ala Val Lys Val Val Glu Leu Pro Thr
        130                 135                 140

Glu Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                165                 170                 175

Leu Lys Ile Leu Pro Asn Asp Glu Cys Lys Lys Ala His Val Gln Lys
            180                 185                 190

Val Thr Asp Phe Met Leu Cys Val Gly His Leu Glu Gly Gly Lys Asp
        195                 200                 205

Thr Cys Val Gly Asp Ser Gly Gly Pro Leu Met Cys Asp Gly Val Leu
    210                 215                 220

Gln Gly Val Thr Ser Trp Gly Tyr Val Pro Cys Gly Thr Pro Asn Lys
225                 230                 235                 240

Pro Ser Val Ala Val Arg Val Leu Ser Tyr Val Lys Trp Ile Glu Asp
                245                 250                 255

Thr Ile Ala Glu Asn Ser
            260

<210> SEQ ID NO 67
<211> LENGTH: 860
<212> TYPE: PRT
<213> ORGANISM: Homo sapiens

<400> SEQUENCE: 67

Met Gly Pro Trp Gly Trp Lys Leu Arg Trp Thr Val Ala Leu Leu Leu
```

-continued

```
1               5                   10                  15
Ala Ala Ala Gly Thr Ala Val Gly Asp Arg Cys Glu Arg Asn Glu Phe
                20                  25                  30
Gln Cys Gln Asp Gly Lys Cys Ile Ser Tyr Lys Trp Val Cys Asp Gly
                35                  40                  45
Ser Ala Glu Cys Gln Asp Gly Ser Asp Glu Ser Gln Glu Thr Cys Leu
 50                  55                  60
Ser Val Thr Cys Lys Ser Gly Asp Phe Ser Cys Gly Gly Arg Val Asn
 65                  70                  75                  80
Arg Cys Ile Pro Gln Phe Trp Arg Cys Asp Gly Gln Val Asp Cys Asp
                85                  90                  95
Asn Gly Ser Asp Glu Gln Gly Cys Pro Pro Lys Thr Cys Ser Gln Asp
                100                 105                 110
Glu Phe Arg Cys His Asp Gly Lys Cys Ile Ser Arg Gln Phe Val Cys
                115                 120                 125
Asp Ser Asp Arg Asp Cys Leu Asp Gly Ser Asp Glu Ala Ser Cys Pro
                130                 135                 140
Val Leu Thr Cys Gly Pro Ala Ser Phe Gln Cys Asn Ser Ser Thr Cys
145                 150                 155                 160
Ile Pro Gln Leu Trp Ala Cys Asp Asn Asp Pro Asp Cys Glu Asp Gly
                165                 170                 175
Ser Asp Glu Trp Pro Gln Arg Cys Arg Gly Leu Tyr Val Phe Gln Gly
                180                 185                 190
Asp Ser Ser Pro Cys Ser Ala Phe Glu Phe His Cys Leu Ser Gly Glu
                195                 200                 205
Cys Ile His Ser Ser Trp Arg Cys Asp Gly Gly Pro Asp Cys Lys Asp
                210                 215                 220
Lys Ser Asp Glu Glu Asn Cys Ala Val Ala Thr Cys Arg Pro Asp Glu
225                 230                 235                 240
Phe Gln Cys Ser Asp Gly Asn Cys Ile His Gly Ser Arg Gln Cys Asp
                245                 250                 255
Arg Glu Tyr Asp Cys Lys Asp Met Ser Asp Glu Val Gly Cys Val Asn
                260                 265                 270
Val Thr Leu Cys Glu Gly Pro Asn Lys Phe Lys Cys His Ser Gly Glu
                275                 280                 285
Cys Ile Thr Leu Asp Lys Val Cys Asn Met Ala Arg Asp Cys Arg Asp
                290                 295                 300
Trp Ser Asp Glu Pro Ile Lys Glu Cys Gly Thr Asn Glu Cys Leu Asp
305                 310                 315                 320
Asn Asn Gly Gly Cys Ser His Val Cys Asn Asp Leu Lys Ile Gly Tyr
                325                 330                 335
Glu Cys Leu Cys Pro Asp Gly Phe Gln Leu Val Ala Gln Arg Arg Cys
                340                 345                 350
Glu Asp Ile Asp Glu Cys Gln Asp Pro Asp Thr Cys Ser Gln Leu Cys
                355                 360                 365
Val Asn Leu Glu Gly Gly Tyr Lys Cys Gln Cys Glu Glu Gly Phe Gln
                370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
                420                 425                 430
```

-continued

```
Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
    835                 840                 845
```

```
Ser Arg Gln Met Val Ser Leu Glu Asp Asp Val Ala
    850                 855                 860
```

<210> SEQ ID NO 68
<211> LENGTH: 800
<212> TYPE: PRT
<213> ORGANISM: Homo sapiens

<400> SEQUENCE: 68

```
Met Gly Thr Ser Ala Leu Trp Ala Leu Trp Leu Leu Leu Ala Leu Cys
1               5                   10                  15

Trp Ala Pro Arg Glu Ser Gly Ala Thr Gly Thr Gly Arg Lys Ala Lys
                20                  25                  30

Cys Glu Pro Ser Gln Phe Gln Cys Thr Asn Gly Arg Cys Ile Thr Leu
            35                  40                  45

Leu Trp Lys Cys Asp Gly Asp Glu Asp Cys Val Asp Gly Ser Asp Glu
    50                  55                  60

Lys Asn Cys Val Lys Lys Thr Cys Ala Glu Ser Asp Phe Val Cys Asn
65                  70                  75                  80

Asn Gly Gln Cys Val Pro Ser Arg Trp Lys Cys Asp Gly Asp Pro Asp
                85                  90                  95

Cys Glu Asp Gly Ser Asp Glu Ser Pro Glu Gln Cys His Met Arg Thr
            100                 105                 110

Cys Arg Ile His Glu Ile Ser Cys Gly Ala His Ser Thr Gln Cys Ile
        115                 120                 125

Pro Val Ser Trp Arg Cys Asp Gly Glu Asn Asp Cys Asp Ser Gly Glu
    130                 135                 140

Asp Glu Glu Asn Cys Gly Asn Ile Thr Cys Ser Pro Asp Glu Phe Thr
145                 150                 155                 160

Cys Ser Ser Gly Arg Cys Ile Ser Arg Asn Phe Val Cys Asn Gly Gln
                165                 170                 175

Asp Asp Cys Ser Asp Gly Ser Asp Glu Leu Asp Cys Ala Pro Pro Thr
            180                 185                 190

Cys Gly Ala His Glu Phe Gln Cys Ser Thr Ser Ser Cys Ile Pro Ile
        195                 200                 205

Ser Trp Val Cys Asp Asp Asp Ala Asp Cys Ser Asp Gln Ser Asp Glu
    210                 215                 220

Ser Leu Glu Gln Cys Gly Arg Gln Pro Val Ile His Thr Lys Cys Pro
225                 230                 235                 240

Ala Ser Glu Ile Gln Cys Gly Ser Gly Glu Cys Ile His Lys Lys Trp
                245                 250                 255

Arg Cys Asp Gly Asp Pro Asp Cys Lys Asp Gly Ser Asp Glu Val Asn
            260                 265                 270

Cys Pro Ser Arg Thr Cys Arg Pro Asp Gln Phe Glu Cys Glu Asp Gly
        275                 280                 285

Ser Cys Ile His Gly Ser Arg Gln Cys Asn Gly Ile Arg Asp Cys Val
    290                 295                 300

Asp Gly Ser Asp Glu Val Asn Cys Lys Asn Val Asn Gln Cys Leu Gly
305                 310                 315                 320

Pro Gly Lys Phe Lys Cys Arg Ser Gly Glu Cys Ile Asp Ile Ser Lys
                325                 330                 335

Val Cys Asn Gln Glu Gln Asp Cys Arg Asp Trp Ser Asp Glu Pro Leu
            340                 345                 350

Lys Glu Cys His Ile Asn Glu Cys Leu Val Asn Asn Gly Gly Cys Ser
        355                 360                 365
```

-continued

```
His Ile Cys Lys Asp Leu Val Ile Gly Tyr Glu Cys Asp Cys Ala Ala
            370                 375                 380

Gly Phe Glu Leu Ile Asp Arg Lys Thr Cys Gly Asp Ile Asp Glu Cys
385                 390                 395                 400

Gln Asn Pro Gly Ile Cys Ser Gln Ile Cys Ile Asn Leu Lys Gly Gly
                405                 410                 415

Tyr Lys Cys Glu Cys Ser Arg Gly Tyr Gln Met Asp Leu Ala Thr Gly
            420                 425                 430

Val Cys Lys Ala Val Gly Lys Glu Pro Ser Leu Ile Phe Thr Asn Arg
        435                 440                 445

Arg Asp Ile Arg Lys Ile Gly Leu Glu Arg Lys Glu Tyr Ile Gln Leu
    450                 455                 460

Val Glu Gln Leu Arg Asn Thr Val Ala Leu Asp Ala Asp Ile Ala Ala
465                 470                 475                 480

Gln Lys Leu Phe Trp Ala Asp Leu Ser Gln Lys Ala Ile Phe Ser Ala
                485                 490                 495

Ser Ile Asp Asp Lys Val Gly Arg His Val Lys Met Ile Asp Asn Val
            500                 505                 510

Tyr Asn Pro Ala Ile Ala Val Asp Trp Val Tyr Lys Thr Ile Tyr
        515                 520                 525

Trp Thr Asp Ala Ala Ser Lys Thr Ile Ser Val Ala Thr Leu Asp Gly
    530                 535                 540

Thr Lys Arg Lys Phe Leu Phe Asn Ser Asp Leu Arg Glu Pro Ala Ser
545                 550                 555                 560

Ile Ala Val Asp Pro Leu Ser Gly Phe Val Tyr Trp Ser Asp Trp Gly
                565                 570                 575

Glu Pro Ala Lys Ile Glu Lys Ala Gly Met Asn Gly Phe Asp Arg Arg
            580                 585                 590

Pro Leu Val Thr Ala Asp Ile Gln Trp Pro Asn Gly Ile Thr Leu Asp
        595                 600                 605

Leu Ile Lys Ser Arg Leu Tyr Trp Leu Asp Ser Lys Leu His Met Leu
    610                 615                 620

Ser Ser Val Asp Leu Asn Gly Gln Asp Arg Arg Ile Val Leu Lys Ser
625                 630                 635                 640

Leu Glu Phe Leu Ala His Pro Leu Ala Leu Thr Ile Phe Glu Asp Arg
                645                 650                 655

Val Tyr Trp Ile Asp Gly Glu Asn Glu Ala Val Tyr Gly Ala Asn Lys
            660                 665                 670

Phe Thr Gly Ser Glu Leu Ala Thr Leu Val Asn Asn Leu Asn Asp Ala
        675                 680                 685

Gln Asp Ile Ile Val Tyr His Glu Leu Val Gln Pro Ser Gly Lys Asn
    690                 695                 700

Trp Cys Glu Glu Asp Met Glu Asn Gly Gly Cys Glu Tyr Leu Cys Leu
705                 710                 715                 720

Pro Ala Pro Gln Ile Asn Asp His Ser Pro Lys Tyr Thr Cys Ser Cys
                725                 730                 735

Pro Ser Gly Tyr Asn Val Glu Asn Gly Arg Asp Cys Gln Arg Ile
            740                 745                 750

Asn Val Thr Thr Ala Val Ser Glu Val Ser Val Pro Pro Lys Gly Thr
        755                 760                 765

Ser Ala Ala Trp Ala Ile Leu Pro Leu Leu Leu Leu Val Met Ala Ala
    770                 775                 780
```

Val Gly Gly Tyr Leu Met Trp Arg Asn Trp Gln His Lys Asn Met Lys
785                 790                 795                 800

<210> SEQ ID NO 69
<211> LENGTH: 873
<212> TYPE: PRT
<213> ORGANISM: Homo sapiens

<400> SEQUENCE: 69

Met Gly Thr Ser Ala Leu Trp Ala Leu Trp Leu Leu Leu Ala Leu Cys
1               5                   10                  15

Trp Ala Pro Arg Glu Ser Gly Ala Thr Gly Thr Gly Arg Lys Ala Lys
                20                  25                  30

Cys Glu Pro Ser Gln Phe Gln Cys Thr Asn Gly Arg Cys Ile Thr Leu
            35                  40                  45

Leu Trp Lys Cys Asp Gly Asp Glu Asp Cys Val Asp Gly Ser Asp Glu
50                  55                  60

Lys Asn Cys Val Lys Lys Thr Cys Ala Glu Ser Asp Phe Val Cys Asn
65                  70                  75                  80

Asn Gly Gln Cys Val Pro Ser Arg Trp Lys Cys Asp Gly Asp Pro Asp
                85                  90                  95

Cys Glu Asp Gly Ser Asp Glu Ser Pro Glu Gln Cys His Met Arg Thr
            100                 105                 110

Cys Arg Ile His Glu Ile Ser Cys Gly Ala His Ser Thr Gln Cys Ile
        115                 120                 125

Pro Val Ser Trp Arg Cys Asp Gly Glu Asn Asp Cys Asp Ser Gly Glu
    130                 135                 140

Asp Glu Glu Asn Cys Gly Asn Ile Thr Cys Ser Pro Asp Glu Phe Thr
145                 150                 155                 160

Cys Ser Ser Gly Arg Cys Ile Ser Arg Asn Phe Val Cys Asn Gly Gln
                165                 170                 175

Asp Asp Cys Ser Asp Gly Ser Asp Glu Leu Asp Cys Ala Pro Pro Thr
            180                 185                 190

Cys Gly Ala His Glu Phe Gln Cys Ser Thr Ser Ser Cys Ile Pro Ile
        195                 200                 205

Ser Trp Val Cys Asp Asp Asp Ala Asp Cys Ser Asp Gln Ser Asp Glu
    210                 215                 220

Ser Leu Glu Gln Cys Gly Arg Gln Pro Val Ile His Thr Lys Cys Pro
225                 230                 235                 240

Ala Ser Glu Ile Gln Cys Gly Ser Gly Glu Cys Ile His Lys Lys Trp
                245                 250                 255

Arg Cys Asp Gly Asp Pro Asp Cys Lys Asp Gly Ser Asp Glu Val Asn
            260                 265                 270

Cys Pro Ser Arg Thr Cys Arg Pro Asp Gln Phe Glu Cys Glu Asp Gly
        275                 280                 285

Ser Cys Ile His Gly Ser Arg Gln Cys Asn Gly Ile Arg Asp Cys Val
    290                 295                 300

Asp Gly Ser Asp Glu Val Asn Cys Lys Asn Val Asn Gln Cys Leu Gly
305                 310                 315                 320

Pro Gly Lys Phe Lys Cys Arg Ser Gly Glu Cys Ile Asp Ile Ser Lys
                325                 330                 335

Val Cys Asn Gln Glu Gln Asp Cys Arg Asp Trp Ser Asp Glu Pro Leu
            340                 345                 350

Lys Glu Cys His Ile Asn Glu Cys Leu Val Asn Asn Gly Gly Cys Ser
        355                 360                 365

-continued

His Ile Cys Lys Asp Leu Val Ile Gly Tyr Glu Cys Asp Cys Ala Ala
    370                 375                 380

Gly Phe Glu Leu Ile Asp Arg Lys Thr Cys Gly Asp Ile Asp Glu Cys
385                 390                 395                 400

Gln Asn Pro Gly Ile Cys Ser Gln Ile Cys Ile Asn Leu Lys Gly Gly
            405                 410                 415

Tyr Lys Cys Glu Cys Ser Arg Gly Tyr Gln Met Asp Leu Ala Thr Gly
            420                 425                 430

Val Cys Lys Ala Val Gly Lys Glu Pro Ser Leu Ile Phe Thr Asn Arg
        435                 440                 445

Arg Asp Ile Arg Lys Ile Gly Leu Glu Arg Lys Glu Tyr Ile Gln Leu
    450                 455                 460

Val Glu Gln Leu Arg Asn Thr Val Ala Leu Asp Ala Asp Ile Ala Ala
465                 470                 475                 480

Gln Lys Leu Phe Trp Ala Asp Leu Ser Gln Lys Ala Ile Phe Ser Ala
            485                 490                 495

Ser Ile Asp Asp Lys Val Gly Arg His Val Lys Met Ile Asp Asn Val
            500                 505                 510

Tyr Asn Pro Ala Ile Ala Val Asp Trp Val Tyr Lys Thr Ile Tyr
        515                 520                 525

Trp Thr Asp Ala Ala Ser Lys Thr Ile Ser Val Ala Thr Leu Asp Gly
    530                 535                 540

Thr Lys Arg Lys Phe Leu Phe Asn Ser Asp Leu Arg Glu Pro Ala Ser
545                 550                 555                 560

Ile Ala Val Asp Pro Leu Ser Gly Phe Val Tyr Trp Ser Asp Trp Gly
            565                 570                 575

Glu Pro Ala Lys Ile Glu Lys Ala Gly Met Asn Gly Phe Asp Arg Arg
            580                 585                 590

Pro Leu Val Thr Ala Asp Ile Gln Trp Pro Asn Gly Ile Thr Leu Asp
        595                 600                 605

Leu Ile Lys Ser Arg Leu Tyr Trp Leu Asp Ser Lys Leu His Met Leu
    610                 615                 620

Ser Ser Val Asp Leu Asn Gly Gln Asp Arg Arg Ile Val Leu Lys Ser
625                 630                 635                 640

Leu Glu Phe Leu Ala His Pro Leu Ala Leu Thr Ile Phe Glu Asp Arg
            645                 650                 655

Val Tyr Trp Ile Asp Gly Glu Asn Glu Ala Val Tyr Gly Ala Asn Lys
            660                 665                 670

Phe Thr Gly Ser Glu Leu Ala Thr Leu Val Asn Asn Leu Asn Asp Ala
        675                 680                 685

Gln Asp Ile Ile Val Tyr His Glu Leu Val Gln Pro Ser Gly Lys Asn
    690                 695                 700

Trp Cys Glu Glu Asp Met Glu Asn Gly Gly Cys Glu Tyr Leu Cys Leu
705                 710                 715                 720

Pro Ala Pro Gln Ile Asn Asp His Ser Pro Lys Tyr Thr Cys Ser Cys
            725                 730                 735

Pro Ser Gly Tyr Asn Val Glu Asn Gly Arg Asp Cys Gln Ser Thr
            740                 745                 750

Ala Thr Thr Val Thr Tyr Ser Glu Thr Lys Asp Thr Asn Thr Thr Glu
        755                 760                 765

Ile Ser Ala Thr Ser Gly Leu Val Pro Gly Gly Ile Asn Val Thr Thr
    770                 775                 780

```
Ala Val Ser Glu Val Ser Val Pro Pro Lys Gly Thr Ser Ala Ala Trp
785                 790                 795                 800

Ala Ile Leu Pro Leu Leu Leu Val Met Ala Ala Val Gly Gly Tyr
                805                 810                 815

Leu Met Trp Arg Asn Trp Gln His Lys Asn Met Lys Ser Met Asn Phe
                820                 825                 830

Asp Asn Pro Val Tyr Leu Lys Thr Thr Glu Glu Asp Leu Ser Ile Asp
                835                 840                 845

Ile Gly Arg His Ser Ala Ser Val Gly His Thr Tyr Pro Ala Ile Ser
                850                 855                 860

Val Val Ser Thr Asp Asp Leu Ala
865                 870
```

<210> SEQ ID NO 70
<211> LENGTH: 1255
<212> TYPE: PRT
<213> ORGANISM: Homo sapiens

<400> SEQUENCE: 70

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
                35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65              70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
            275                 280                 285
```

```
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
                435                 440                 445
Gly Ile Ser Trp Leu Gly Leu Arg Ser Leu Arg Glu Leu Gly Ser Gly
                450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Pro Thr Gln Cys
                515                 520                 525
Val Asn Cys Ser Gln Phe Leu Arg Gly Gln Glu Cys Val Glu Glu Cys
                530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
                595                 600                 605
Ser Tyr Met Pro Ile Trp Lys Phe Pro Asp Glu Glu Gly Ala Cys Gln
                610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
                660                 665                 670
Ile Leu Ile Lys Arg Arg Gln Gln Lys Ile Arg Lys Tyr Thr Met Arg
                675                 680                 685
Arg Leu Leu Gln Glu Thr Glu Leu Val Glu Pro Leu Thr Pro Ser Gly
                690                 695                 700
```

-continued

```
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
        835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
        915                 920                 925
Arg Glu Ile Pro Asp Leu Leu Glu Lys Gly Glu Arg Leu Pro Gln Pro
930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
        995                 1000                1005
Leu Glu Asp Asp Asp Met Gly Asp Leu Val Asp Ala  Glu Glu Tyr
1010                1015                1020
Leu Val Pro Gln Gln Gly Phe  Phe Cys Pro Asp Pro  Ala Pro Gly
1025                1030                1035
Ala Gly Gly Met Val His His  Arg His Arg Ser  Ser Thr Arg
1040                1045                1050
Ser Gly Gly Gly Asp Leu Thr  Leu Gly Leu Glu  Pro Ser Glu Glu
1055                1060                1065
Glu Ala Pro Arg Ser Pro Leu  Ala Pro Ser Glu Gly  Ala Gly Ser
1070                1075                1080
Asp Val Phe Asp Gly Asp Leu  Gly Met Gly Ala Ala  Lys Gly Leu
1085                1090                1095
Gln Ser Leu Pro Thr His Asp  Pro Ser Pro Leu Gln  Arg Tyr Ser
1100                1105                1110
Glu Asp Pro Thr Val Pro Leu  Pro Ser Glu Thr Asp  Gly Tyr Val
```

-continued

```
              1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 71
<211> LENGTH: 1225
<212> TYPE: PRT
<213> ORGANISM: Homo sapiens

<400> SEQUENCE: 71

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220
```

```
Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Asp Gly Thr Gln Arg Cys Glu Lys Cys
290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
                340                 345                 350

Gly Asp Pro Ala Ser Asn Thr Ala Pro Leu Gln Pro Gln Leu Gln
            355                 360                 365

Val Phe Glu Thr Leu Glu Glu Ile Thr Gly Tyr Leu Tyr Ile Ser Ala
370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
            435                 440                 445

Thr Val Pro Trp Asp Gln Leu Phe Arg Asn Pro His Gln Ala Leu Leu
450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
            515                 520                 525

His Cys Leu Pro Cys His Pro Glu Cys Gln Pro Gln Asn Gly Ser Val
530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
            595                 600                 605

Asp Lys Gly Cys Pro Ala Glu Gln Arg Ala Ser Pro Leu Thr Ser Ile
            610                 615                 620

Ile Ser Ala Val Val Gly Ile Leu Leu Val Val Leu Gly Val Val
625                 630                 635                 640

Phe Gly Ile Leu Ile Lys Arg Arg Gln Gln Lys Ile Arg Lys Tyr Thr
```

-continued

```
                645                 650                 655
Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
            675                 680                 685

Glu Leu Arg Lys Val Lys Val Leu Gly Ser Gly Ala Phe Gly Thr Val
            690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
            755                 760                 765

Gln Leu Met Pro Tyr Gly Cys Leu Leu Asp His Val Arg Glu Asn Arg
770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
            835                 840                 845

Ala Asp Gly Gly Lys Val Pro Ile Lys Trp Met Ala Leu Glu Ser Ile
850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
            915                 920                 925

Trp Met Ile Asp Ser Glu Cys Arg Pro Arg Phe Arg Glu Leu Val Ser
            930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
            995                 1000                1005

Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050

Asp Val Phe Asp Gly Asp Leu Gly Met Gly Ala Ala Lys Gly Leu
    1055                1060                1065
```

```
Gln Ser Leu Pro Thr His Asp Pro Ser Pro Leu Gln Arg Tyr Ser
    1070                1075                1080
Glu Asp Pro Thr Val Pro Leu Pro Ser Glu Thr Asp Gly Tyr Val
    1085                1090                1095
Ala Pro Leu Thr Cys Ser Pro Gln Pro Glu Tyr Val Asn Gln Pro
    1100                1105                1110
Asp Val Arg Pro Gln Pro Ser Pro Arg Glu Gly Pro Leu Pro
    1115                1120                1125
Ala Ala Arg Pro Ala Gly Ala Thr Leu Glu Arg Pro Lys Thr Leu
    1130                1135                1140
Ser Pro Gly Lys Asn Gly Val Val Lys Asp Val Phe Ala Phe Gly
    1145                1150                1155
Gly Ala Val Glu Asn Pro Glu Tyr Leu Thr Pro Gln Gly Gly Ala
    1160                1165                1170
Ala Pro Gln Pro His Pro Pro Ala Phe Ser Pro Ala Phe Asp
    1175                1180                1185
Asn Leu Tyr Tyr Trp Asp Gln Asp Pro Pro Glu Arg Gly Ala Pro
    1190                1195                1200
Pro Ser Thr Phe Lys Gly Thr Pro Thr Ala Glu Asn Pro Glu Tyr
    1205                1210                1215
Leu Gly Leu Asp Val Pro Val
    1220                1225

<210> SEQ ID NO 72
<211> LENGTH: 654
<212> TYPE: PRT
<213> ORGANISM: Homo sapiens

<400> SEQUENCE: 72

Met Lys Leu Ser Leu Val Ala Ala Met Leu Leu Leu Leu Ser Ala Ala
1               5                   10                  15
Arg Ala Glu Glu Glu Asp Lys Lys Glu Asp Val Gly Thr Val Val Gly
            20                  25                  30
Ile Asp Leu Gly Thr Thr Tyr Ser Cys Val Gly Val Phe Lys Asn Gly
        35                  40                  45
Arg Val Glu Ile Ile Ala Asn Asp Gln Gly Asn Arg Ile Thr Pro Ser
    50                  55                  60
Tyr Val Ala Phe Thr Pro Glu Gly Glu Arg Leu Ile Gly Asp Ala Ala
65                  70                  75                  80
Lys Asn Gln Leu Thr Ser Asn Pro Glu Asn Thr Val Phe Asp Ala Lys
                85                  90                  95
Arg Leu Ile Gly Arg Thr Trp Asn Asp Pro Ser Val Gln Gln Asp Ile
            100                 105                 110
Lys Phe Leu Pro Phe Lys Val Val Glu Lys Lys Thr Lys Pro Tyr Ile
        115                 120                 125
Gln Val Asp Ile Gly Gly Gly Gln Thr Lys Thr Phe Ala Pro Glu Glu
    130                 135                 140
Ile Ser Ala Met Val Leu Thr Lys Met Lys Glu Thr Ala Glu Ala Tyr
145                 150                 155                 160
Leu Gly Lys Lys Val Thr His Ala Val Val Thr Val Pro Ala Tyr Phe
                165                 170                 175
Asn Asp Ala Gln Arg Gln Ala Thr Lys Asp Ala Gly Thr Ile Ala Gly
            180                 185                 190
Leu Asn Val Met Arg Ile Ile Asn Glu Pro Thr Ala Ala Ala Ile Ala
```

-continued

```
            195                 200                 205
Tyr Gly Leu Asp Lys Arg Glu Gly Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                    245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Gly Leu Asn Met Asp Leu Phe Arg
                    325                 330                 335

Ser Thr Met Lys Pro Val Gln Lys Val Leu Glu Asp Ser Asp Leu Lys
                340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                    405                 410                 415

Leu Asp Val Cys Pro Leu Thr Leu Gly Ile Glu Thr Val Gly Gly Val
                420                 425                 430

Met Thr Lys Leu Ile Pro Arg Asn Thr Val Val Pro Thr Lys Lys Ser
            435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                    485                 490                 495

Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                    565                 570                 575

Gly Asp Lys Glu Lys Leu Gly Gly Lys Leu Ser Ser Glu Asp Lys Glu
                580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
    610                 615                 620
```

```
Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
            645                 650
```

```
<210> SEQ ID NO 73
<211> LENGTH: 493
<212> TYPE: PRT
<213> ORGANISM: Homo sapiens

<400> SEQUENCE: 73
```

```
Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Met Asn Pro Thr
50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
                85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
```

```
                340                 345                 350
Phe Phe Asn Gly Lys Glu Leu Asn Lys Ser Ile Asn Pro Asp Glu Ala
            355                 360                 365

Val Ala Tyr Gly Ala Ala Val Gln Ala Ile Leu Ser Gly Asp Lys
    370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Lys Phe Glu Leu Thr Gly Met
            450                 455                 460

Pro Gly Gly Met Pro Gly Gly Phe Pro Gly Gly Ala Pro Pro Ser
465                 470                 475                 480

Gly Gly Ala Ser Ser Gly Pro Thr Ile Glu Glu Val Asp
            485                 490

<210> SEQ ID NO 74
<211> LENGTH: 646
<212> TYPE: PRT
<213> ORGANISM: Homo sapiens

<400> SEQUENCE: 74

Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Met Asn Pro Thr
    50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
                85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
    130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
    210                 215                 220
```

-continued

```
Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
            340                 345                 350

Phe Phe Asn Gly Lys Glu Leu Asn Lys Ser Ile Asn Pro Asp Glu Ala
        355                 360                 365

Val Ala Tyr Gly Ala Ala Val Gln Ala Ala Ile Leu Ser Gly Asp Lys
370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Lys Phe Glu Leu Thr Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
            500                 505                 510

Glu Asp Ile Glu Arg Met Val Gln Glu Ala Glu Lys Tyr Lys Ala Glu
        515                 520                 525

Asp Glu Lys Gln Arg Asp Lys Val Ser Ser Lys Asn Ser Leu Glu Ser
530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
            580                 585                 590

Glu His Gln Gln Lys Glu Leu Glu Lys Val Cys Asn Pro Ile Ile Thr
        595                 600                 605

Lys Leu Tyr Gln Ser Ala Gly Gly Met Pro Gly Gly Met Pro Gly Gly
610                 615                 620

Phe Pro Gly Gly Gly Ala Pro Pro Ser Gly Gly Ala Ser Ser Gly Pro
625                 630                 635                 640

Thr Ile Glu Glu Val Asp
```

645

<210> SEQ ID NO 75
<211> LENGTH: 188
<212> TYPE: PRT
<213> ORGANISM: Homo sapiens

<400> SEQUENCE: 75

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 76
<211> LENGTH: 153
<212> TYPE: PRT
<213> ORGANISM: Homo sapiens

<400> SEQUENCE: 76

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe

Cys Gln Ser Ile Ile Ser Thr Leu Thr
145                 150

<210> SEQ ID NO 77
<211> LENGTH: 407
<212> TYPE: PRT
<213> ORGANISM: Homo sapiens

<400> SEQUENCE: 77

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Pro Pro Pro Pro Pro Pro Gly Ser Pro
        35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125

His Ala Ser Pro Gly Ala Asp Gly Gln Glu Arg Val Ser Glu Ile Ile
    130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
            180                 185                 190

Ser Arg Arg Lys Val Arg Val Lys Val Tyr Phe Gln Glu Gln Gly His
        195                 200                 205

Gly Asp Arg Trp Asn Met Val Glu Lys Arg Val Asp Leu Lys Arg Ser
    210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
                245                 250                 255

Glu Leu Ala Val Val Pro Val Phe Val Asp Pro Gly Glu Glu Ser His
            260                 265                 270

Arg Pro Phe Val Val Val Gln Ala Arg Leu Gly Asp Ser Arg His Arg
        275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
            340                 345                 350

```
Ala Val Val Asn Gln Tyr Arg Met Arg Gly Leu Asn Pro Gly Thr Val
            355                 360                 365

Asn Ser Cys Cys Ile Pro Thr Lys Leu Ser Thr Met Ser Met Leu Tyr
370                 375                 380

Phe Asp Asp Glu Tyr Asn Ile Val Lys Arg Asp Val Pro Asn Met Ile
385                 390                 395                 400

Val Glu Glu Cys Gly Cys Ala
                405

<210> SEQ ID NO 78
<211> LENGTH: 582
<212> TYPE: PRT
<213> ORGANISM: Homo sapiens

<400> SEQUENCE: 78

Met Ser Pro Ala Pro Arg Pro Pro Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320
```

Gly Asn Phe Asp Thr Val Ala Met Leu Arg Gly Glu Met Phe Val Phe
            325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
            355                 360                 365

Asn Thr Ala Tyr Glu Arg Lys Asp Gly Lys Phe Val Phe Lys Gly
            370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
            405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
            435                 440                 445

Tyr Pro Lys Asn Ile Lys Val Trp Glu Gly Ile Pro Glu Ser Pro Arg
            450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
            485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Thr Glu Val Ile Ile Ile Glu
            515                 520                 525

Val Asp Glu Glu Gly Gly Gly Ala Val Ser Ala Ala Val Val Leu
530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
            565                 570                 575

Ser Leu Leu Asp Lys Val
            580

<210> SEQ ID NO 79
<211> LENGTH: 418
<212> TYPE: PRT
<213> ORGANISM: Homo sapiens

<400> SEQUENCE: 79

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
            35                  40                  45

Pro Ile Asp Thr Phe Pro Thr Asp Pro Ile Lys Glu Ser Ser Trp Pro
            50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
            85                  90                  95

Tyr Lys His Glu Gln Val Tyr Ile Arg Ser Thr Asp Val Asp Arg Thr

-continued

```
                100                 105                 110
Leu Met Ser Ala Met Thr Asn Leu Ala Ala Leu Phe Pro Pro Glu Gly
            115                 120                 125

Val Ser Ile Trp Asn Pro Ile Leu Leu Trp Gln Pro Ile Pro Val His
        130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Val Leu Lys Val Ile
370                 375                 380

Phe Ala Val Ala Phe Cys Leu Ile Ser Ala Val Leu Met Val Leu Leu
385                 390                 395                 400

Phe Ile His Ile Arg Arg Gly Leu Cys Trp Gln Arg Glu Ser Tyr Gly
                405                 410                 415

Asn Ile

<210> SEQ ID NO 80
<211> LENGTH: 386
<212> TYPE: PRT
<213> ORGANISM: Homo sapiens

<400> SEQUENCE: 80

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
```

```
                    50                  55                  60
        Gln Gly Phe Gly Gln Leu Thr Gln Leu Gly Met Glu Gln His Tyr Glu
         65                  70                  75                  80

Leu Gly Glu Tyr Ile Arg Lys Arg Tyr Arg Lys Phe Leu Asn Glu Ser
                         85                  90                  95

Tyr Lys His Glu Gln Val Tyr Ile Arg Ser Thr Asp Val Asp Arg Thr
        100                 105                 110

Leu Met Ser Ala Met Thr Asn Leu Ala Ala Leu Phe Pro Pro Glu Gly
                    115                 120                 125

Val Ser Ile Trp Asn Pro Ile Leu Leu Trp Gln Pro Ile Pro Val His
                130                 135                 140

Thr Val Pro Leu Ser Glu Asp Gln Leu Leu Tyr Leu Pro Phe Arg Asn
        145                 150                 155                 160

Cys Pro Arg Phe Gln Glu Leu Glu Ser Glu Thr Leu Lys Ser Glu Glu
                            165                 170                 175

Phe Gln Lys Arg Leu His Pro Tyr Lys Asp Phe Ile Ala Thr Leu Gly
                        180                 185                 190

Lys Leu Ser Gly Leu His Gly Gln Asp Leu Phe Gly Ile Trp Ser Lys
                    195                 200                 205

Val Tyr Asp Pro Leu Tyr Cys Glu Ser Val His Asn Phe Thr Leu Pro
                210                 215                 220

Ser Trp Ala Thr Glu Asp Thr Met Thr Lys Leu Arg Glu Leu Ser Glu
        225                 230                 235                 240

Leu Ser Leu Leu Ser Leu Tyr Gly Ile His Lys Gln Lys Glu Lys Ser
                            245                 250                 255

Arg Leu Gln Gly Gly Val Leu Val Asn Glu Ile Leu Asn His Met Lys
                        260                 265                 270

Arg Ala Thr Gln Ile Pro Ser Tyr Lys Lys Leu Ile Met Tyr Ser Ala
                    275                 280                 285

His Asp Thr Thr Val Ser Gly Leu Gln Met Ala Leu Asp Val Tyr Asn
                290                 295                 300

Gly Leu Leu Pro Pro Tyr Ala Ser Cys His Leu Thr Glu Leu Tyr Phe
        305                 310                 315                 320

Glu Lys Gly Glu Tyr Phe Val Glu Met Tyr Tyr Arg Asn Glu Thr Gln
                            325                 330                 335

His Glu Pro Tyr Pro Leu Met Leu Pro Gly Cys Ser Pro Ser Cys Pro
                        340                 345                 350

Leu Glu Arg Phe Ala Glu Leu Val Gly Pro Val Ile Pro Gln Asp Trp
                    355                 360                 365

Ser Thr Glu Cys Met Thr Thr Asn Ser His Gln Gly Thr Glu Asp Ser
                370                 375                 380

Thr Asp
        385

<210> SEQ ID NO 81
<211> LENGTH: 646
<212> TYPE: PRT
<213> ORGANISM: Homo sapiens

<400> SEQUENCE: 81

Met Gly Leu Pro Arg Leu Val Cys Ala Phe Leu Leu Ala Ala Cys Cys
          1               5                  10                  15

Cys Cys Pro Arg Val Ala Gly Val Pro Gly Glu Ala Glu Gln Pro Ala
                         20                  25                  30
```

```
Pro Glu Leu Val Glu Val Glu Val Gly Ser Thr Ala Leu Leu Lys Cys
             35                  40                  45

Gly Leu Ser Gln Ser Gln Gly Asn Leu Ser His Val Asp Trp Phe Ser
 50                  55                  60

Val His Lys Glu Lys Arg Thr Leu Ile Phe Arg Val Arg Gln Gly Gln
 65                  70                  75                  80

Gly Gln Ser Glu Pro Gly Glu Tyr Glu Gln Arg Leu Ser Leu Gln Asp
                 85                  90                  95

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
            115                 120                 125

Gln Leu Arg Val Tyr Lys Ala Pro Glu Glu Pro Asn Ile Gln Val Asn
        130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
        210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
                260                 265                 270

Leu Ala Asp Gly Asn Pro Pro His Phe Ser Ile Ser Lys Gln Asn
        275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Gly Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
```

```
                450              455             460
Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Glu Thr Gly
                485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
                515                 520                 525

Thr Thr Gly Leu Ser Thr Ser Thr Ala Ser Pro His Thr Arg Ala Asn
                530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
                580                 585                 590

Ser Gly Lys Gln Glu Ile Thr Leu Pro Pro Ser Arg Lys Ser Glu Leu
                595                 600                 605

Val Val Glu Val Lys Ser Asp Lys Leu Pro Glu Glu Met Gly Leu Leu
610                 615                 620

Gln Gly Ser Ser Gly Asp Lys Arg Ala Pro Gly Asp Gln Gly Glu Lys
625                 630                 635                 640

Tyr Ile Asp Leu Arg His
                645

<210> SEQ ID NO 82
<211> LENGTH: 20
<212> TYPE: PRT
<213> ORGANISM: Artificial Sequence
<220> FEATURE:
<223> OTHER INFORMATION: Synthetic peptides

<400> SEQUENCE: 82

Thr Lys Ala Gly Arg Gly Ala Ser Gln Pro Pro Thr Pro Thr Pro Ala
1               5                   10                  15

Ser Asp Ala Phe
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic peptides

<400> SEQUENCE: 83

Glu Glu Glu Pro Glu Glu Thr Ala Glu Asp Thr Thr Glu Asp Thr Glu
1               5                   10                  15

Gln Asp Glu Asp
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic peptides

<400> SEQUENCE: 84
```

```
Thr Ala Ser Thr Thr Ala Asn Thr Pro Phe Pro Thr Ala Thr Ser Pro
1               5                   10                  15

Ala Pro Pro Ile
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic peptides

<400> SEQUENCE: 85

Pro Ala Pro Pro Ile Ile Ser Thr His Ser Ser Ser Thr Ile Pro Thr
1               5                   10                  15

Pro Ala Pro Pro
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic peptides

<400> SEQUENCE: 86

Leu Ala Lys Met Tyr Tyr Ser Ala Val Glu Pro Thr Lys Asp Ile Phe
1               5                   10                  15

Thr Gly Leu Ile
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic peptides

<400> SEQUENCE: 87

Pro Ser Ser Thr Lys Pro Pro Ala Leu Ser His Ser Val Ser Thr Ser
1               5                   10                  15

Ser Thr Thr Lys
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic peptides

<400> SEQUENCE: 88

Leu Glu Pro Asp Tyr Phe Lys Asp Met Thr Pro Thr Ile Arg Lys Thr
1               5                   10                  15

Gln Lys Ile Val
            20

<210> SEQ ID NO 89
<211> LENGTH: 20
<212> TYPE: PRT
<213> ORGANISM: Artificial Sequence
<220> FEATURE:
<223> OTHER INFORMATION: Synthetic peptides
```

```
<400> SEQUENCE: 89

Ser Thr Met Pro Val Val Ser Ser Glu Ala Ser Thr His Ser Thr Thr
1               5                   10                  15

Pro Val Asp Thr
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic peptides

<400> SEQUENCE: 90

Ser Thr His Ser Thr Thr Pro Val Asp Thr Ser Thr Pro Val Thr Thr
1               5                   10                  15

Ser Thr Glu Ala
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic peptides

<400> SEQUENCE: 91

Ile Pro Pro Glu Asp Thr Ala Ser Thr Arg Ser Ser Phe Thr Val Gln
1               5                   10                  15

Asp Leu Lys Pro
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic peptides

<400> SEQUENCE: 92

Glu Ala Lys Thr Ser Asn Pro Thr Ser Ser Leu Thr Ser Leu Ser Val
1               5                   10                  15

Ala Pro Thr Phe
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic peptides

<400> SEQUENCE: 93

Ala Arg Thr Glu Pro Trp Glu Gly Asn Ser Ser Thr Ala Ala Thr Thr
1               5                   10                  15

Pro Glu Thr Phe
            20

<210> SEQ ID NO 94
<211> LENGTH: 20
<212> TYPE: PRT
<213> ORGANISM: Artificial Sequence
<220> FEATURE:
<223> OTHER INFORMATION: Synthetic peptides
```

-continued

<400> SEQUENCE: 94

Val Asp Pro Leu Gln Leu Gln Thr Pro Pro Gln Thr Gln Pro Gly Pro
1               5                   10                  15

Ser His Val Met
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic peptides

<400> SEQUENCE: 95

Ser Pro Lys Pro Ser Thr Thr Asn Val Phe Thr Ser Ala Val Asp Gln
1               5                   10                  15

Thr Ile Thr Pro
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic peptides

<400> SEQUENCE: 96

Pro Ala Pro Pro Ala Pro Gly Asn Ala Ser Glu Ser Glu Glu Asp Arg
1               5                   10                  15

Ser Ala Gly Ser
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic peptides

<400> SEQUENCE: 97

Ala Ser Glu Ser Glu Glu Asp Arg Ser Ala Gly Ser Val Glu Ser Pro
1               5                   10                  15

Ser Val Ser Ser
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic peptides

<400> SEQUENCE: 98

Ala Asn Leu Asn Ser Asp Lys Glu Asn Ile Thr Thr Ser Asn Leu Lys
1               5                   10                  15

Ala Ser His Ser
            20

<210> SEQ ID NO 99
<211> LENGTH: 20
<212> TYPE: PRT
<213> ORGANISM: Artificial Sequence
<220> FEATURE:

<223> OTHER INFORMATION: Synthetic peptides

<400> SEQUENCE: 99

Leu Thr Thr Asn Ser Asp Ser Phe Thr Gly Phe Thr Pro Tyr Gln Glu
1               5                   10                  15

Lys Thr Thr Leu
            20

<210> SEQ ID NO 100
<211> LENGTH: 20
<212> TYPE: PRT
<213> ORGANISM: Artificial Sequence
<220> FEATURE:
<223> OTHER INFORMATION: Synthetic peptides

<400> SEQUENCE: 100

Ser Phe Thr Gly Phe Thr Pro Tyr Gln Glu Lys Thr Thr Leu Gln Pro
1               5                   10                  15

Thr Leu Lys Phe
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic peptides

<400> SEQUENCE: 101

Ser Phe Thr Gly Phe Thr Pro Tyr Gln Glu Lys Thr Thr Leu Gln Pro
1               5                   10                  15

Thr Leu Lys Phe
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic peptides

<400> SEQUENCE: 102

Ser Pro Thr Ser Ser Ala Ser Ser Phe Ser Ser Ser Ala Pro Phe Leu
1               5                   10                  15

Ala Ser Ala Val
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic peptides

<400> SEQUENCE: 103

Thr Val Pro Cys Pro Val Pro Ser Thr Pro Pro Thr Pro Ser Pro Ser
1               5                   10                  15

Thr Pro Pro Thr
            20

<210> SEQ ID NO 104
<211> LENGTH: 20
<212> TYPE: PRT
<213> ORGANISM: Artificial Sequence
<220> FEATURE:
<223> OTHER INFORMATION: Synthetic peptides

<400> SEQUENCE: 104

Val Pro Ser Thr Pro Pro Thr Pro Ser Pro Ser Thr Pro Pro Thr Pro
1               5                   10                  15

Ser Pro Ser Cys
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic peptides

<400> SEQUENCE: 105

Ser Glu Pro Pro Lys Ala Ala Arg Pro Pro Val Thr Pro Val Leu Leu
1               5                   10                  15

Glu Lys Lys Ser
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic peptides

<400> SEQUENCE: 106

Gly Gln Ser Gln Pro Thr Val Ala Gly Gln Pro Ser Ala Arg Pro Ala
1               5                   10                  15

Ala Glu Glu Tyr
            20

<210> SEQ ID NO 107
<211> LENGTH: 20
<212> TYPE: PRT
<213> ORGANISM: Artificial Sequence
<220> FEATURE:
<223> OTHER INFORMATION: Synthetic peptides

<400> SEQUENCE: 107

Thr Pro Ala Ser Ile Thr Ala Ala Lys Thr Ser Thr Ile Thr Thr Ala
1               5                   10                  15

Phe Pro Pro Val
            20

<210> SEQ ID NO 108
<211> LENGTH: 20
<212> TYPE: PRT
<213> ORGANISM: Artificial Sequence
<220> FEATURE:
<223> OTHER INFORMATION: Synthetic peptides

<400> SEQUENCE: 108

Gly Asn Ala Ser Met Asp Ala Val Cys Thr Ser Thr Ser Pro Thr Arg
1               5                   10                  15

Ser Met Ala Pro
            20

<210> SEQ ID NO 109
<211> LENGTH: 20
<212> TYPE: PRT

```
<213> ORGANISM: Artificial Sequence
<220> FEATURE:
<223> OTHER INFORMATION: Synthetic peptides

<400> SEQUENCE: 109

Thr Asp Cys Gly Gly Pro Lys Asp His Pro Leu Thr Cys Asp Pro
1               5                   10                  15

Arg Phe Gln Ala
            20

<210> SEQ ID NO 110
<211> LENGTH: 21
<212> TYPE: PRT
<213> ORGANISM: Artificial Sequence
<220> FEATURE:
<223> OTHER INFORMATION: Synthetic peptides

<400> SEQUENCE: 110

Ala Gln Ala Ser Ser Ser Ser Lys Ala Pro Pro Ser Leu Pro Ser
1               5                   10                  15

Pro Ser Arg Leu Pro
            20

<210> SEQ ID NO 111
<211> LENGTH: 20
<212> TYPE: PRT
<213> ORGANISM: Artificial Sequence
<220> FEATURE:
<223> OTHER INFORMATION: Synthetic peptides

<400> SEQUENCE: 111

Pro Leu Ser Glu Leu Glu Ser Gly Glu Gln Pro Ser Asp Glu Gln Pro
1               5                   10                  15

Ser Gly Glu His
            20

<210> SEQ ID NO 112
<211> LENGTH: 20
<212> TYPE: PRT
<213> ORGANISM: Artificial Sequence
<220> FEATURE:
<223> OTHER INFORMATION: Synthetic peptides

<400> SEQUENCE: 112

Pro Gln Arg Ser Ser Thr Ala Ile Leu Gln Val Ser Val Thr Asp Thr
1               5                   10                  15

Asn Asp Asn His
            20

<210> SEQ ID NO 113
<211> LENGTH: 20
<212> TYPE: PRT
<213> ORGANISM: Artificial Sequence
<220> FEATURE:
<223> OTHER INFORMATION: Synthetic peptides

<400> SEQUENCE: 113

Gly Ala Leu Pro Gly Thr Ser Val Met Glu Val Thr Ala Thr Asp Ala
1               5                   10                  15

Asp Asp Asp Val
            20

<210> SEQ ID NO 114
<211> LENGTH: 20
```

```
<212> TYPE: PRT
<213> ORGANISM: Artificial Sequence
<220> FEATURE:
<223> OTHER INFORMATION: Synthetic peptides

<400> SEQUENCE: 114

Glu Gln Glu Pro Pro Ser Thr Asp Val Pro Pro Ser Pro Glu Ala Gly
1               5                   10                  15

Gly Thr Thr Gly
            20

<210> SEQ ID NO 115
<211> LENGTH: 20
<212> TYPE: PRT
<213> ORGANISM: Artificial Sequence
<220> FEATURE:
<223> OTHER INFORMATION: Synthetic peptides

<400> SEQUENCE: 115

Arg Pro Glu Ala Thr Pro Phe Leu Val Ala His Thr Arg Thr Arg Pro
1               5                   10                  15

Pro Ser Gly Gly
            20

<210> SEQ ID NO 116
<211> LENGTH: 20
<212> TYPE: PRT
<213> ORGANISM: Artificial Sequence
<220> FEATURE:
<223> OTHER INFORMATION: Synthetic peptides

<400> SEQUENCE: 116

Pro Gly Thr Ser Thr Thr Pro Ser Gln Pro Asn Ser Ala Gly Val Gln
1               5                   10                  15

Asp Thr Glu Met
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic peptides

<400> SEQUENCE: 117

Glu Val Ala Pro Glu Ala Ser Thr Ser Ser Ala Ser Gln Val Ile Ala
1               5                   10                  15

Pro Thr Gln Val
            20

<210> SEQ ID NO 118
<211> LENGTH: 20
<212> TYPE: PRT
<213> ORGANISM: Artificial Sequence
<220> FEATURE:
<223> OTHER INFORMATION: Synthetic peptides

<400> SEQUENCE: 118

Gln Pro Pro Asp Phe Ala Leu Ala Tyr Arg Pro Ser Phe Pro Glu Asp
1               5                   10                  15

Arg Glu Pro Gln
            20

<210> SEQ ID NO 119
```

```
<211> LENGTH: 20
<212> TYPE: PRT
<213> ORGANISM: Artificial Sequence
<220> FEATURE:
<223> OTHER INFORMATION: Synthetic peptides

<400> SEQUENCE: 119

Leu Ser Val Thr Arg Pro Val Val Val Ser Ala Thr His Pro Thr Leu
1               5                   10                  15

Pro Ser Ala His
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic peptides

<400> SEQUENCE: 120

Pro Ser Ala His Gln Pro Pro Val Ile Pro Ala Thr His Pro Ala Leu
1               5                   10                  15

Ser Arg Asp His
            20

<210> SEQ ID NO 121
<211> LENGTH: 20
<212> TYPE: PRT
<213> ORGANISM: Artificial Sequence
<220> FEATURE:
<223> OTHER INFORMATION: Synthetic peptides

<400> SEQUENCE: 121

Ala Pro Asp Ala Leu Val Leu Arg Thr Gln Ala Thr Gln Leu Pro Ile
1               5                   10                  15

Ile Pro Thr Ala
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic peptides

<400> SEQUENCE: 122

Gly Ala Leu Phe Pro Gly Pro Gly Asn Ala Gln Thr Ser Val Ser Pro
1               5                   10                  15

Ser Lys Val Ile
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic peptides

<400> SEQUENCE: 123

His Leu Ala Leu Gly Asp Gln Arg Leu Asn Pro Thr Val Thr Tyr Gly
1               5                   10                  15

Asn Asp Ser Phe
            20
```

```
<210> SEQ ID NO 124
<211> LENGTH: 20
<212> TYPE: PRT
<213> ORGANISM: Artificial Sequence
<220> FEATURE:
<223> OTHER INFORMATION: Synthetic peptides

<400> SEQUENCE: 124

His Leu Ala Leu Gly Asp Gln Arg Leu Asn Pro Thr Val Thr Tyr Gly
1               5                   10                  15

Asn Asp Ser Phe
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic peptides

<400> SEQUENCE: 125

Pro Ala Thr Glu Pro Ala Ser Gly Ser Ala Ala Thr Trp Gly Gln Asp
1               5                   10                  15

Val Thr Ser Val
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic peptides

<400> SEQUENCE: 126

Val Pro Val Thr Arg Pro Ala Leu Gly Ser Thr Thr Pro Pro Ala His
1               5                   10                  15

Asp Val Thr Ser
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic peptides

<400> SEQUENCE: 127

Asn Val Thr Ser Ala Ser Gly Ser Ala Ser Gly Ser Ala Ser Thr Leu
1               5                   10                  15

Val His Asn Gly
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic peptides

<400> SEQUENCE: 128

Asn Val Thr Ser Ala Ser Gly Ser Ala Ser Gly Ser Ala Ser Thr Leu
1               5                   10                  15

Val His Asn Gly
            20
```

<210> SEQ ID NO 129
<211> LENGTH: 20
<212> TYPE: PRT
<213> ORGANISM: Artificial Sequence
<220> FEATURE:
<223> OTHER INFORMATION: Synthetic peptides

<400> SEQUENCE: 129

Gly Thr Ser Ala Arg Ala Thr Thr Thr Pro Ala Ser Lys Ser Thr Pro
1               5                   10                  15

Phe Ser Ile Pro
            20

<210> SEQ ID NO 130
<211> LENGTH: 20
<212> TYPE: PRT
<213> ORGANISM: Artificial Sequence
<220> FEATURE:
<223> OTHER INFORMATION: Synthetic peptides

<400> SEQUENCE: 130

Gly Thr Ser Ala Arg Ala Thr Thr Thr Pro Ala Ser Lys Ser Thr Pro
1               5                   10                  15

Phe Ser Ile Pro
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic peptides

<400> SEQUENCE: 131

Ser Asp Thr Pro Thr Thr Leu Ala Ser His Ser Thr Lys Thr Asp Ala
1               5                   10                  15

Ser Ser Thr His
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptides

<400> SEQUENCE: 132

Thr Lys Thr Asp Ala Ser Ser Thr His His Ser Thr Val Pro Pro Leu
1               5                   10                  15

Thr Ser Ser Asn
            20

<210> SEQ ID NO 133
<211> LENGTH: 20
<212> TYPE: PRT
<213> ORGANISM: Artificial Sequence
<220> FEATURE:
<223> OTHER INFORMATION: Synthetic peptides

<400> SEQUENCE: 133

Thr Asp Tyr Tyr Gln Glu Leu Gln Arg Asp Ile Ser Glu Met Phe Leu
1               5                   10                  15

Gln Ile Tyr Lys
            20

<210> SEQ ID NO 134
<211> LENGTH: 20
<212> TYPE: PRT
<213> ORGANISM: Artificial Sequence
<220> FEATURE:
<223> OTHER INFORMATION: Synthetic peptides

<400> SEQUENCE: 134

His Asp Val Glu Thr Gln Phe Asn Gln Tyr Lys Thr Glu Ala Ala Ser
1               5                   10                  15

Arg Tyr Asn Leu
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic peptides

<400> SEQUENCE: 135

Ala Ser Arg Tyr Asn Leu Thr Ile Ser Asp Val Ser Val Ser Asp Val
1               5                   10                  15

Pro Phe Pro Phe
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic peptides

<400> SEQUENCE: 136

Arg Tyr Asn Leu Thr Ile Ser Asp Val Ser Val Ser Asp Val Pro Phe
1               5                   10                  15

Pro Phe Ser Ala
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic peptides

<400> SEQUENCE: 137

Asp Val Ser Val Ser Asp Val Pro Phe Pro Phe Ser Ala Gln Ser Gly
1               5                   10                  15

Ala Gly Val Pro
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic peptides

<400> SEQUENCE: 138

Thr Ala Gly Arg Pro Thr Gly Gln Ser Ser Pro Thr Ser Pro Ser Ala
1               5                   10                  15

Ser Pro Gln Glu

```
<210> SEQ ID NO 139
<211> LENGTH: 20
<212> TYPE: PRT
<213> ORGANISM: Artificial Sequence
<220> FEATURE:
<223> OTHER INFORMATION: Synthetic peptides

<400> SEQUENCE: 139

Ser Leu Ala Ser Gln Ala Thr Asp Thr Phe Ser Val Pro Pro Thr
1               5                   10                  15

Pro Pro Ser Ile
            20

<210> SEQ ID NO 140
<211> LENGTH: 20
<212> TYPE: PRT
<213> ORGANISM: Artificial Sequence
<220> FEATURE:
<223> OTHER INFORMATION: Synthetic peptides

<400> SEQUENCE: 140

Phe Ser Thr Val Pro Pro Thr Pro Pro Ser Ile Thr Ser Thr Gly Leu
1               5                   10                  15

Thr Ser Pro Gln
            20

<210> SEQ ID NO 141
<211> LENGTH: 20
<212> TYPE: PRT
<213> ORGANISM: Artificial Sequence
<220> FEATURE:
<223> OTHER INFORMATION: Synthetic peptides

<400> SEQUENCE: 141

Pro Thr Pro Pro Ser Ile Thr Ser Thr Gly Leu Thr Ser Pro Gln Thr
1               5                   10                  15

Glu Thr His Thr
            20

<210> SEQ ID NO 142
<211> LENGTH: 20
<212> TYPE: PRT
<213> ORGANISM: Artificial Sequence
<220> FEATURE:
<223> OTHER INFORMATION: Synthetic peptides

<400> SEQUENCE: 142

Leu Thr Ser Pro Gln Thr Glu Thr His Thr Leu Ser Pro Ser Gly Ser
1               5                   10                  15

Gly Lys Thr Phe
            20

<210> SEQ ID NO 143
<211> LENGTH: 20
<212> TYPE: PRT
<213> ORGANISM: Artificial Sequence
<220> FEATURE:
<223> OTHER INFORMATION: Synthetic peptides

<400> SEQUENCE: 143

Thr Asp Thr Ser Ser Ala Ser Thr Gly His Ala Thr Pro Leu Pro Val
1               5                   10                  15
```

```
<210> SEQ ID NO 144
<211> LENGTH: 20
<212> TYPE: PRT
<213> ORGANISM: Artificial Sequence
<220> FEATURE:
<223> OTHER INFORMATION: Synthetic peptides

<400> SEQUENCE: 144

His Ala Thr Pro Leu Ala Val Ser Ser Ala Thr Ser Ala Ser Thr Val
1               5                   10                  15

Ser Ser Asp Ser
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic peptides

<400> SEQUENCE: 145

Val Pro Val Thr Arg Pro Ala Leu Gly Ser Thr Thr Pro Pro Ala His
1               5                   10                  15

Asp Val Thr Ser
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic peptides

<400> SEQUENCE: 146

Ser Leu Ala Ser Gln Ala Thr Asp Thr Phe Ser Thr Val Pro Pro Thr
1               5                   10                  15

Pro Pro Ser Ile
            20
```

METHODS OF IDENTIFYING GLYCOPEPTIDES RECOGNIZED BY DISEASE-ASSOCIATED AUTO-ANTIBODIES

CROSS REFERENCE TO PRIOR APPLICATION

This application claims the benefit of U.S. Provisional Application Ser. No. 61/293,583 filed Jan. 8, 2010 and 61/294,477 filed Jan. 12, 2010, both of which are incorporated by reference herein in their entirety.

FIELD OF THE INVENTION

The present invention is related to methods for identifying glycopeptides and more particularly glycopeptide epitopes that are specifically recognized by disease-associated auto-antibodies. In some aspects the auto-antibodies are cancer-associated or autoimmune disease-associated. The invention also relates to methods of diagnosing a patient with cancer or an autoimmune disease, or for eliciting an immune response in a mammalian host directed to a glycopeptide of the invention. The invention also relates to novel individual glycopeptides as well as to panels of glycopeptides (whether individually novel or not) useful for autoantibody detection purposes.

BACKGROUND OF INVENTION

Malignant transformation of cells is virtually always accompanied by alterations in the posttranslational modifications (PTMs) of proteins, and one of the best documented examples is the abundant mucin-type O-glycosylation (hereafter referred to as O-glycosylation) found on mucins and other O-glycoproteins (Tarp and Clausen 2008). Tumor-associated changes in expression of O-glycoproteins and/or in their aberrant glycosylation, create a diverse set of unusual molecular structures found on the surface of cancer cells as well as in secretions. These molecular structures generally represent glycoproteins with truncated immature O-glycans, to which the immune system of man is not normally exposed except, in some cases, as biosynthetic intermediates and then only in the secretory pathway. Therefore, these structures may represent a different form of tumor-associated antigens (one not necessarily based on differential expression level or sequence mutation), to which individuals lack immunological tolerance and thus provoke both auto-antibodies and cell mediated immunity (Anderton 2004; Doyle and Mamula 2005; Doyle and Mamula 2001).

Several mouse antibodies have been isolated and characterized as having unique binding specificity for combined glycopeptide epitopes that include both the peptide sequence as well as the aberrant PTM (hereinafter "APTM") for efficient binding. Examples include monoclonal antibodies that specifically recognize distinct O-glycopeptides from MUC2, MUC1, and other glycoproteins (Reis et al. 1998; Sorensen et al. 2006; Danielczyk et al. 2006; Dian et al. 2009; Li et al. 2009; Takeuchi et al. 2002; Clark et al. 1998).

There exist examples of human antibodies with selective or specific reactivity with PTM-modified proteins, but these are generally limited to inflammatory and autoimmune diseases (Anderton 2004; Doyle and Mamula 2005; Doyle and Mamula 2001). Furthermore, human hydridoma technologies have identified natural IgM antibodies that react with glycoforms of proteins but the nature of the epitopes has not been fully clarified (Rauschert et al. 2008; Vollmers and Brandlein 2009; Brandlein et al. 2004a; Brandlein et al. 2004b; Rasmussen and Ditzel 2009). A major drawback of current technologies to screen for auto-antibodies directed against APTM proteins is the lack of high through-put methods for identifying antigens, more particularly epitopes, for generating pertinent antigens and for screening such antigens.

In principle, cancer-associated auto-antibodies represent appealing potential biomarkers. Auto-antibodies may develop early in carcinogenesis, at the time tumor-associated antigens appear on premalignant or malignant lesions. Antibody responses can produce relatively high concentrations in circulation with a long circulation time, and they can be detected with sensitive and specific methods (see, (Lu et al. 2008; Anderson and Labaer 2005)). In contrast, antigens produced by small premalignant or malignant lesions are generally produced in vanishingly small levels that due to dilution and clearance from blood may not be detectable by conventional techniques. Discovery and characterization of specific auto-antibodies to cancer antigens have been undertaken using different approaches in the past. Classical studies identified such antibodies reactive with tumor cells, tissues, or isolated proteins (Kawabata et al. 2007), but distinct molecular features of binding epitopes have generally not resulted from these approaches.

More recent proteome-wide screening techniques have included expressed cDNA libraries (SEREX) (Sahin et al. 1995), protein and peptide arrays (Stockert et al. 1998; Pereira-Faca et al. 2007), random or designed phage displays (Mintz et al. 2003), and more recently self-assembling protein arrays (Ramachandran et al. 2008; Anderson et al. 2008). Cancer-associated auto-antibodies characterized to date have been found to bind intracellular proteins with functions important in cell cycle regulation, such as GPR78 (Mintz et al. 2003), p53 (Lubin et al. 1993), NY-ESO-1, and CDC25 (Liu et al. 2008), but also some cell membrane glycoproteins such as MUC1 (Snijdewint et al. 1999), HER2 (Chapman et al. 2007) and Mesothelin (Hellstrom et al. 2008).

Auto-antibodies are believed to be induced as a result of altered expression of proteins and altered molecular structure due to mutations, alternative splicing and post-translational events such as protein processing and aberrant enzymatic modifications including glycosylation (Anderton 2004; Doyle and Mamula 2005; Doyle and Mamula 2001). These events induce breakage of tolerance and immunity may result. Surprisingly, however, few disease- or more specifically cancer-associated auto-antibody epitopes have been identified and molecularly defined despite considerable efforts and broad proteome screening. This is due to limitations in methods for identification of such auto-antibodies, in that, before the present invention, the appropriate antigen epitopes have not been determined and hence not tested to lead to identification of disease-associated antibodies, to serve as substrates for the detection of disease or to serve as prototype vaccines for induction of immunity against the epitopes of these autoantibodies.

There are few known examples of disease-associated human antibodies to proteins involving glycosylation. One important example is an immunodominant epitope in type II collagen comprising a glycosylated hydroxylysine residue that is involved in collagen-induced arthritis (Backlund et al. 2002). Glycosylation may also modulate protein processing and hence affect exposure of new epitopes as shown in Rasmussen's encephalitis, where an N-glycan blocks proteolysis of a neuronal glutamate receptor and a short preceding peptide epitope (Gahring et al. 2001). Several human monoclonal antibodies have been shown to be directed to epitopes affected by glycosylation (Rauschert et al. 2008; Vollmers and Brandlein 2009; Brandlein et al. 2004a; Brandlein et al.

2004b; Rasmussen and Ditzel 2009), but the nature of the molecular epitopes remains undefined.

There is therefore a need to develop methods for the identification of PTM-containing peptides, such as aberrant glycopeptides (hereinafter "AGP"), that are specifically recognized by disease-associated auto-antibodies. The present invention provides such methods. There is also a need for improved diagnostic tools, such as AGP, that would permit early detection of disease, notably cancer, for example by being used as substrates to capture disease-associated autoantibodies.

SUMMARY OF INVENTION

In one embodiment, the invention provides a method for identifying glycopeptides reactive with cancer-associated auto-antibodies, the method comprising: providing a panel comprising peptides, at least a plurality of the peptides comprising one or more sites amenable to glycosylation, wherein at least one of the glycosylation sites has been modified with a glycan to form a glycopeptide having a peptide portion and a glycan portion; contacting the panel with an antibody-containing sample from a patient with cancer; and identifying glycopeptides in the panel that (i) are selectively recognized by antibodies in the sample, but not by antibodies in a control sample and (ii) are recognized by such antibodies in the sample through recognition of both the peptide portion and the glycan portion and not through recognition of either the peptide or the glycan alone.

In another embodiment, a panel of the invention comprises a plurality of peptides having an amino acid sequence comprising at least one serine or threonine residue, wherein the residue is a glycosylation site. In yet another embodiment, the at least one serine or threonine residue is at about the middle of the amino acid sequence. In still another embodiment, a panel of the invention comprises mutants of the peptides. The number of peptides in a panel may vary and may be at least 8 peptides, for example between about 8 and about 30 peptides, such as 10, 12, 15 or 20 peptides. A number of peptides in excess of 30 is also within the invention. The upper limit of peptides in a panel is limited by practical considerations (e.g., how many peptides can fit on a substrate) or cost-benefit considerations. Preferably the peptides are selected from the group consisting of SEQ ID NOs 15, 36, 49, and 82-146.

In a specific aspect of the above embodiment, providing a method for identifying glycopeptides reactive with cancer-associated auto-antibodies, the method further comprises identifying cancer-associated glycopeptide epitopes. In another aspect, the method further comprising elucidating the epitope structure of the identified glycopeptide epitopes.

In a specific embodiment, the invention provides a method for determining whether a patient has cancer, the method comprising: contacting an antibody-containing sample from the patient with a panel comprising peptides at least a plurality of which are glycopeptides, each glycopeptide comprising a glycopeptide epitope, the epitope having been previously determined (i) to be selectively recognized by a subset of antibodies in sera from cancer patients, which subset recognizes neither (a) the corresponding naked peptides of the panel when not glycosylated; nor (b) the corresponding glycan when not bound to the peptide; and (ii) not to be recognized by antibodies in control sera; contacting the panel with an antibody-containing sample from the patient; determining if antibodies in the sample are bound to glycopeptides of the panel; and concluding either that the patient has cancer if the sample comprises antibodies that bind to at least one of the glycopeptides in the panel; or that the patient does not have cancer if the sample does not comprise antibodies that bind to at least one glycopeptide in the panel.

In one aspect of the above embodiment providing a method for determining whether a patient has cancer, the patient is newly diagnosed with cancer. In another aspect, the method further comprises concluding either that the patient has cancer if the sample comprises IgG antibodies that bind to at least one of the glycopeptides in the panel; or that the patient does not have cancer if the sample does not comprise IgG antibodies that bind to at least one glycopeptide in the panel. In yet another aspect, the patient is diagnosed with cancer if said sample comprises antibodies that specifically recognize one or more of the glycopeptides having an amino acid sequence selected from the group consisting of: SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

In another embodiment, the invention provides a method for eliciting an immune response in a patient, the method comprising administering to the patient a composition comprising (i) a glycopeptide consisting essentially of an amino acid sequence selected from the group consisting of SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146), in an effective amount for eliciting the immune response; and (ii) a suitable adjuvant.

In a specific aspect of the above embodiment, providing a method for eliciting an immune response in a patient, the immune response comprises an IgG antibody response. In another aspect, the immune response is an anti-cancer immune response. In yet another aspect, the cancer is selected from the group consisting of breast cancer; colon cancer; ovarian cancer; cervical cancer; pancreatic cancer; prostatic cancer; liver cancer; kidney cancer; brain cancer; hematological cancer; testis cancer; head and neck cancer; and lung cancer.

In one aspect of the above embodiment, providing a method for eliciting an immune response in a patient, the glycopeptide is modified with an O-glycan at at least one amino acid residue. In another aspect, the at least one amino acid residue is a serine or threonine residue.

In any of the above embodiments of the invention, each of the peptides in the panel may be about 2 to about 50 amino acid residues in length. In other aspects, each of the peptides in the panel may be about 4 to about 25 amino acid residues in length.

In certain aspects of the above embodiments of the invention, the amino acid sequence of the peptides of the panel is a fragment found in a protein or variant of said protein or a conservative mutant. In some of the above embodiments, the identified glycopeptides of the panel are found in at least one glycoprotein that is aberrantly glycosylated in cancer cells. In yet other of the above embodiments, glycopeptides identified by the methods of the present invention are found in at least one glycoprotein that is overexpressed in cancer cells.

In other aspects, the glycopeptides are synthesized synthetically or chemoenzymatically. In still other of the above aspects, the glycopeptides of the panel are partially glycosylated peptides when immobilized on the panel.

In certain of the above embodiments, the control sample contains pooled samples from a plurality of control individuals.

In certain of the above aspects of the invention, the panel is a microarray slide. In other aspects, the glycopeptides identified by the methods of the invention are selectively recognized by an IgG antibody. In certain of the above embodiments, the panel comprises one or more glycopeptides having an amino acid sequence selected from the group consisting of: SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

In another aspect, the invention provides a glycopeptide comprising an amino acid sequence selected from the group consisting of SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

In yet another aspect, the invention provides a glycopeptide consisting essentially of an amino acid sequence selected from the group consisting of SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

In still another aspect, the invention provides a glycopeptide consisting of an amino acid sequence selected from the group consisting of SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49), LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

In another aspect, the invention provides a pharmaceutical composition comprising one or more glycopeptides selected from the group consisting of SEQ ID NOs 15, 36, 49, and 82-146. Preferably, the pharmaceutical composition comprises one or more glycopeptides selected from the group consisting of LAKMYYSAVEPTKDIFTGLI (SEQ ID NO: 86); TDCGGPKDHPLTDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

In yet another aspect, the invention provides for a panel of glycopeptides comprising at least a plurality of glycopeptides, each glycopeptide comprising a glycopeptide epitope, said epitope having been previously determined (i) to be selectively recognized by a subset of antibodies in sera from cancer patients, which subset recognizes neither (a) the corresponding naked peptides of said panel when not glycosylated; nor (b) the corresponding glycan when not bound to said peptide; and (ii) not to be recognized by antibodies in control sera, said plurality comprising at least 8 glycopeptides selected from the group consisting of glycopeptides having SEQ IDs 15, 36, 49, and 82-146. Preferably, the plurality of glycopeptides comprises SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

In any of the above embodiments of the invention, the glycopeptides of the panel may be glycosylated in situ, in solution, or in vivo by recombinant expression in a host cell. In any of the above embodiments, the glycopeptides of the panel may be treated with one or more exoglycosidases to expose O-glycans. In still other of the above embodiments, the glycan may be an O-glycan. In any of the above embodiments, the O-glycan may be a member selected from the group consisting of: Tn, STn, T, Truncated C3, Truncated C2, Truncated C4, non-capped type1-C3, non-capped type2-C2, non-capped type2-C4, GalNAca-Tn, SA-type1-C3, SLea-C3, LacDiNAc-C3, LacDiNAc-C2, and LacDiNAc-C4.

In certain of the above embodiments, at least one glycopeptide in the panel is not a glycopeptide comprising a glycosylated GSTA motif.

In certain of the above embodiments, none of the glycopeptides in the panel are glycopeptides comprising a glycosylated GSTA motif.

These and other aspects of the present invention will be apparent to those of ordinary skill in the art in light of the present specification, claims and drawings.

BRIEF DESCRIPTION OF THE DRAWINGS

FIG. 1A: GalNAc-T3 untreated array, FIG. 1B: GalNAc-T3 treated array.

FIG. 6 are bar graphs showing 8 selected glycopeptides (i.e., 889, 275a, 585, 893, 931-C3, 852-C3, 873, and 690) reactive with IgG from newly diagnosed cancer patients compared to normal control sera. FIG. 6A: glycopeptides 889 (SEQ ID NO: 134), 275a (SEQ ID NO: 86), and 585 (SEQ ID NO: 109). FIG. 6B: glycopeptides 893 (SEQ ID NO: 135), 931-C3 (SEQ ID NO: 146), and 852-C3 (SEQ ID NO: 145).

DETAILED DESCRIPTION OF THE INVENTION

Figure 1:
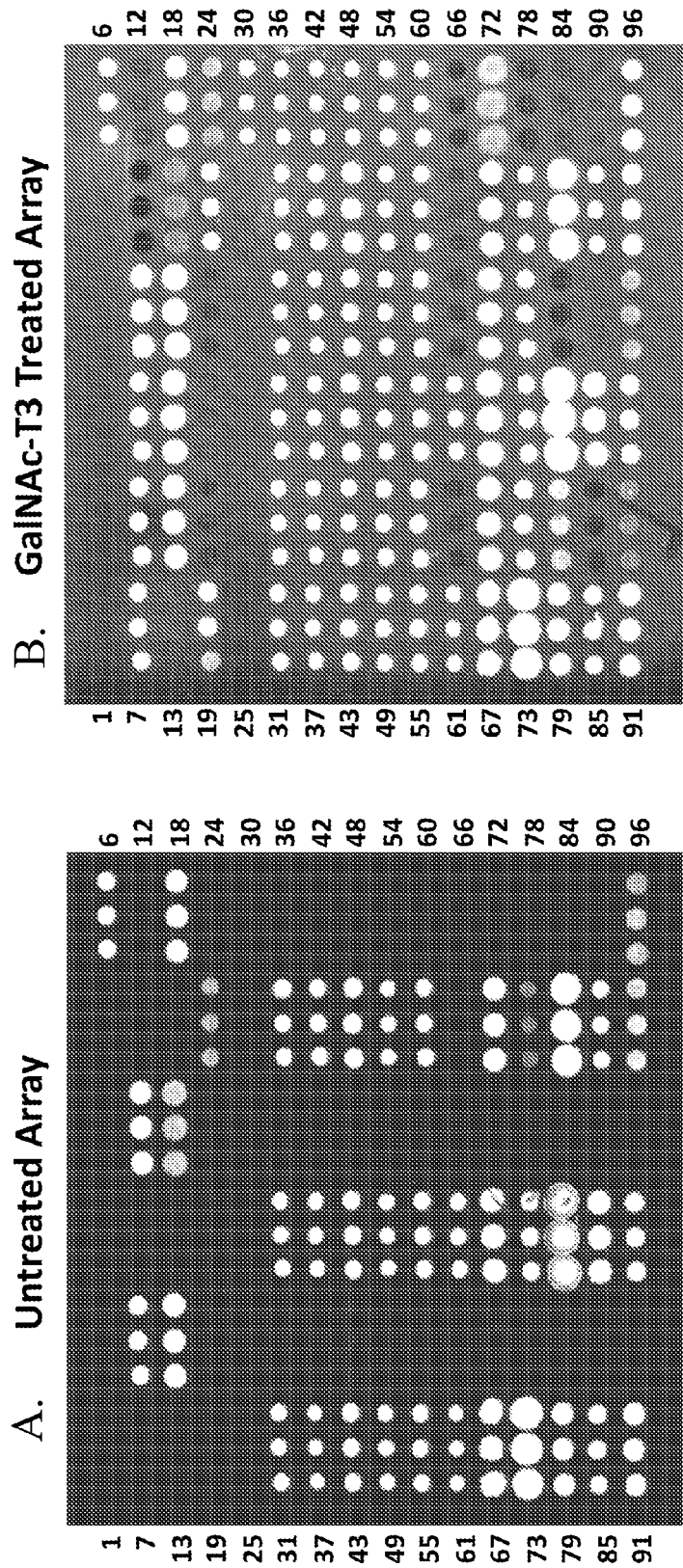
FIG. 1 is an image of a microarray slide and illustrates an example of on-slide (in vitro) glycosylation with a polypeptide GalNAc-transferase, GalNAc-T3, to glycosylate peptides and GalNAc glycopeptides with additional unsubstituted Ser/Thr residues to enhance number of O-glycans.

The present invention provides methods for identification of peptides and peptide epitopes that comprise one or more posttranslational modification(s) (PTM(s)) ("PTM-peptides"/"PTM peptide epitopes") that are selectively recognized and bound by human disease-associated antibodies. These will include peptides that display an aberrant glycosylation pattern either due to an alteration in sequence (mutation) which invites a changed glycosylation pattern, or simply a glycosylation pattern not normally encountered in cancer-free individuals. Such peptides will constitute AGP as the term is introduced and hence defined above. For the removal of doubt, PTM-epitopes are not whole molecules; therefore, any discussion of such epitopes should be construed as applying to glycopeptides harboring such epitopes.

In some aspects, the PTM-peptides of the invention are useful for diagnosing a disease. In a specific embodiment, the present invention provides methods for diagnosing a patient with cancer. In another embodiment, the patient is newly diagnosed with cancer (i.e., diagnosed with cancer for the first time). In still other embodiments, a patient is diagnosed with an autoimmune disease.

In certain embodiments, the methods are useful for identifying PTM-peptides that are useful for eliciting in an individual an immune response directed against PTM-epitopes that are associated with disease, such as cancer. In certain embodiments, the immune response includes an auto-antibody response. In certain aspects, the induction of auto-antibodies to aberrant PTM-modified glycoproteins includes antibodies that specifically recognize O-glycopeptide epitopes.

As discussed, supra, malignant transformation of cells is virtually always accompanied by alterations in the posttranslational modifications (PTMs) of proteins, including O-glycosylation (Tarp and Clausen 2008). Tumor-associated changes in expression of O-glycoproteins and/or in their aberrant glycosylation, create a diverse set of unusual molecular structures found on the surface of cancer cells as well as in secretions. These molecular structures generally represent glycoproteins with truncated immature O-glycans, to which the immune system of man is not normally exposed except, in some cases, as biosynthetic intermediates and then only in the secretory pathway. Thus, one aspect of the PTM-peptides and PTM peptide epitopes identified by the methods of the present invention, i.e., AGP, is that they are not covered by immunological tolerance, and hence are potential targets for immunotherapeutic intervention. The aim of eliciting immune responses in a host using the AGP of the invention is the development of vaccines against the very disease that the AGP or other PTM-peptides are associated with.

Thus, AGP can cause induction of auto-antibodies to PTM-peptide epitopes. One aspect of this invention is the design and production of PTM-peptide libraries that represent or more accurately contain AGP associated with disease. In another aspect of the invention, high through-put methods for screening of disease-associated antibodies using such libraries are provided. In a specific embodiment, the invention relates to aberrant O-glycosylation of glycoproteins and more specifically, of glycopeptides. The present inventors believe one of the reasons why these disease-associated PTM-peptides and epitopes have eluded detection and especially association with disease is that the proteins bearing them in vivo are not or not necessarily mutated or overexpressed and hence would not be detected by ordinary, nontargeted, techniques.

PTM modifications can be the result of the addition of chemical groups to a protein, such as a phosphate group or a sugar moiety (e.g. acetylation of lysine and serine, glycosylation of asparagine, serine, threonine, hydroxyl-proline, lysine, methylation of arginine, histidine, and lysine, phosphorylation of serine, threonine, and tyrosine). They can also be the result of a conversion of an amino acid to a distinct structure, as in the deimination of arginine to citrulline or the deamidation of aspartic acid/asparagine to isoaspartic acid. While this invention is primarily concerned with glycosylation, it is evident that other aberrant posttranslational modifications as described herein may result in altered proteins harboring aberrant PTM-epitopes that may be the target of auto-immunity.

In some aspects of the present invention, the discriminating characteristic of the peptides and peptide epitopes useful in the present invention is that disease-associated antibodies bind selectively with the PTM-containing peptide and not with the same unmodified peptide or the PTM in the context of a different peptide sequence or another unrelated (e.g., artificial) carrier. In terms of AGP having diagnostic and/or immunogenic value, the disease-associated autoantibodies should recognize only the combination of the relevant glycosylated amino acid sequence and not the same glycan on a different peptide nor the same amino acid sequence bearing a different glycan. This will avoid false positives. It will be understood that the construction of peptide libraries and the availability of disease (e.g., cancer) and control sera that can be tested renders it unnecessary to know beforehand which AGP will be recognized by disease-associated antibodies in order to identify these antibodies. Once the disease-associated antibodies have been identified, they, or man-made versions thereof can be used to pinpoint the AGP that pulled relevant autoantibodies out of the sera.

In other aspects, the invention provides methods for the diagnosis of a patient with a disease, such as, e.g., cancer, wherein detection of antibodies in a sample from the patient that selectively recognize one or more combinations of disease-associated PTM-containing peptides is used to predict and diagnose disease. In still other embodiments, methods for treating a patient with cancer using compositions or vaccines comprising PTM-containing peptides or proteins of the invention are provided.

DEFINITIONS

As used herein, the term "immune response" includes an adaptive immune response, including a T cell response and B cell response. Thus, as used herein, the term "eliciting an immune response" means that an adaptive immune response is induced by administration of an appropriate immunogen (antigen or antigen plus carrier).

As used herein, an "anti-cancer immune response" is an immune response that is directed toward cancer cells or products secreted or shed from cancer cells. For example, an anti-cancer immune response may be characterized by tumor-specific antibodies and/or cytotoxic T cells that attack cancer cells or react specifically with a glycoprotein shed from cancer cells.

An "auto-antibody" is an antibody that specifically recognizes an epitope harbored by a self-product such as a protein, carbohydrate or lipid produced by healthy or diseased cells of an individual.

As used herein, the terms "selective binding" and "selective recognition" and their grammatical variants, of an epitope by an antibody means that the antibody binds with significantly greater affinity to the epitope compared to any other sequence or structure.

The term "epitope" refers to the part of an antigen that is specifically recognized and bound by an antibody. The term "glycopeptide epitope" is an epitope that includes both part of a peptide sequence and at least part of a glycan. The term "minimal epitope" or "minimal glycopeptide epitope" refers to the shortest glycopeptide that is recognized by antibodies recognizing the same epitope.

As used herein, the term "corresponding peptide" refers to the unglycosylated form of a glycopeptide of the invention. Thus, a glycopeptide and its corresponding peptide have the same amino acid sequence.

The term "glycan hapten" refers to glycan moiety independent of whether this is conjugated to a carrier, such as a peptide or protein (i.e. binding to the glycan hapten does not depend on the carrier such as protein or peptide to which the glycan is bound).

The terms "linear peptide" and "linear peptide epitope" means that the peptide or peptide epitope is non-conformational (i.e., antibody recognition and binding to the epitope does not depend upon the three-dimensional structure of the peptide).

The term "disease-associated antibody" means an antibody that is detected in a patient sample if the patient has the disease, but is not detected, or is present at significantly reduced levels compared to the patient sample, in a control sample. For example, a cancer-associated antibody is present in an antibody-containing sample from a patient with cancer, but is not present, or is present at significantly reduced levels in a sample from a patient without cancer. A useful distinguishing range of antibody levels is at least two or preferably three 3 fold higher levels in patients compared to healthy control. The term may also apply to groups of patients with a disease, where "disease-associated antibody" means an antibody that is detected with higher prevalence/incidence in the disease group compared to a healthy control group. A useful distinguishing prevalence (=specificity of assay) would be at least 70% and preferably 80 or 90%, The term "aberrant glycosylation" means a glycoform that is not normally present on proteins expressed on the cell surface or secreted/shed from cells. An example of an aberrant glycoform is Tn (GalNAcα1-O-Ser/Thr), sialosyl-Tn (NeuAcα2-8GalNAcα1-O-Ser/Thr), and T (Galβ1-3GalNAcα1-O-Ser/Thr).

As used herein, a "glycosylatable peptide" or a peptide containing a "site amenable to glycosylation" refers to a peptide containing an amino acid residue that can be glycosylated. An example of a site amenable to glycosylation is a peptide site containing a serine or threonine amino acid residue, which can be O-glycosylated with N-acetyl-galactosamine (GalNAc).

As used herein, "variant" in addition to its understood meaning as a term of art includes any changes in a molecule from its wild-type form. For example, alleles, fragments, mutations, substitutions with natural or analog compounds, splice variants, glycosylations, species variants, and the like. The term is not limited to any one type of change or deviation from the wild type form or "normal" molecule. A "variant" also includes a polypeptide or enzyme which has at least 60% amino acid identity as determined by BLAST or FASTA algorithms, preferably at least 75%, most preferably at least 85%, and even more preferably at least 90%, and still more preferably at least 95%, and which has the same or substantially similar properties or functions as the native or parent protein or enzyme to which it is compared.

"Conservative mutants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide.

An "organ-specific glycoprotein" is a glycoprotein which is only or which has substantial preferential expressed in a specific organ type. For example, the protein mucin 16 (MUC16) (SEQ ID NO: 57), is only expressed in epithelium of the female tract such as ovary and endometrium, and it is primarily overexpressed in tumors originating from these epithelia.

The term "clinical debut" refers to the first time a patient is diagnosed with a disease.

The term "immunogenic substitution" means the replacement of an amino acid residue with a different amino acid that causes the antigen to become immunogenic. For example, a substitution of an amino acid in a self protein, such as that which can result from a cancer mutation, or experimentally in a peptide, that renders the self protein immunogenic (i.e., breaks immunogenic tolerance to the self protein) is an immunogenic substitution. As another example, the substitution of a normally unmodified amino acid with a modified amino acid, wherein the modification itself (i.e., as a hapten, such as, e.g., Tn) is immunogenic, can render a protein immunogenic.

The term "subject" or "individual" as used herein refers to an animal having an immune system, preferably a mammal (e.g., rodent, such as mouse). In particular, the term encompasses humans.

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

As used herein, the term "consisting essentially of" means that the glycopeptide sequence is not limited to a length of 20 amino acids, but can be longer or shorter. For example, a glycopeptide can be less than or more than 20 amino acids long as established during the course of optimizing the length of the peptide and efficient positioning of the glycosylated epitope that is specifically recognized by auto-antibodies in patients. Throughout the specification, the length of 20 amino acids is used as a convenient length and to ensure that the entire epitope is encompassed within the peptide. While most epitopes will be on the order of 5-10 amino acid residues, and hence contained within a 20 amino acid peptide, any size peptide is possible if sufficient to contain the epitope for antibody detection. In turn, longer peptides may allow for incorporation of additional epitopes which could provide different selectivity for cancer.

Post-Translational Modification of Peptides

In some aspects, the invention relates to the identification of disease-associated PTM-peptides, wherein the PTM-peptide is selectively recognized by disease-associated antibodies. Preferably, the disease-associated antibodies recognize neither the peptide alone nor the PTM alone or attached to a different peptide. In other words, the antibody epitope comprises both part of the protein backbone and part of the PTM.

The PTM may be one or more modifications of one or more residues of the amino acid sequence. The PTM can be any of the known PTMs involving enzymatic modifications of amino acids including glycosylation, phosphorylation, citrinylation, acetylation, methylation (Anderton 2004; Doyle and Mamula 2005; Doyle and Mamula 2001).

All 20 primary amino acids used by man are capable of undergoing some type of PTM. However, certain factors determine whether those modifications will take place. First, the location of the amino acid within the protein sequence affects both the type and frequency of modifications that may arise. Flanking residues can influence the conformation of the protein, potentially altering whether an enzyme has access to a certain amino acid or is exposed to a certain environment. The cellular location of the modifying enzyme, if required, will determine whether the modification occurs and disease-associated changes in localization of such enzymes may lead to aberrant posttranslational modifications. Previous modifications or proteolytic cleavages within a protein influence subsequent amino acid modifications within the same protein.

An exemplary PTM of the invention is mucin-type O-linked glycosylation ("O-glycosylation" or "O-linked glycosylation"). Examples of O-linked glycosylation include, e.g., the addition of N-acetyl-galactosamine (GalNAc), fucose, glucose, N-acetylglucosamine (GlcNAc), or mannose. GalNAc O-glycosylation is a particularly preferred PTM of the invention. GalNAc O-glycosylation is carried out by specific enzymes; for example, the addition of N-acetyl-galactosamine (GalNAc) to serine or threonine residues is carried out by the enzyme UDP-N-acetyl-D-galactosamine:polypeptide N-acetylgalactosaminyltransferase (EC 2.4.1.41). Other types of O-glycosylation include αMannose, αFucose, βGlucose, βGlcNAc, and βXylose glycosylation. Also contemplated by the present invention are other forms of glycosylation, such as, e.g., N-linked glycosylation, hydroxyl-lysine glycosylation, and C-mannosylation. Biosynthesis and structures of these types of protein glycosylation are reviewed in Essentials of Glycobiology ($2^{nd}$ edtion, eds A. Varki, Cummings, Esko, Freeze, Stanley Bertozzi, Hart, Etzler. CSH Press 2009). It is to be understood that examples of PTM modification provided herein, such as O-glycosylation, are meant to be non-limiting examples which serve to prove the principal of the present methods (i.e., that the presently disclosed methods are useful for identifying PTM-modified peptides or peptide epitopes specifically recognized by disease-associated antibodies). The methods of the invention are also applicable, however, to proteins or peptides modified with other PTMs contemplated by the present invention, such as but not limited to phosphorylation, citrinylation, acetylation, and methylation.

In certain aspects of the invention, glycoproteins, glycopeptides and glycopeptide epitopes that are aberrantly glycosylated are provided. Examples of aberrant forms of O-glycans include, but are not limited to, truncated immature O-glycans such as Tn, T, and STn as well as non-sialylated and non-galactosylated core 2, 3 and 4 structures, shown in Table I below:

TABLE I

Representative mucin-type O-glycan structures on normal and diseased cells[1]

| Name | Hapten Structure (+/−Ser/Thr or artificial linker) | Type of Glycoconjugate | Distribution (main) | No |
|---|---|---|---|---|
| Tn | GalNAcα1-O-Ser/Thr | O-linked | Cancer cells | 1 |
| STn | NeuAcα2-3GalNAcα1-O-Ser/Thr | O-linked | Cancer cells | 2 |
| T | Galβ1-3GalNAcα1-O-Ser/Thr | O-linked | Cancer cells | 3 |
| mSTa | NeuAcA2-3Galβ1-3GalNAcα1-O-Ser/Thr | O-linked | Normal cells | 4 |
| mSTb | NeuAcA2-3Galβ1-3[NeuAcα2-6]GalNAcα1-O-Ser/Thr | O-linked | Normal cells | 5 |
| Truncated C3 | GlcNAcβ1-3GalNAcα1-O-Ser/Thr | O-linked | Cancer cells | 6 |
| Truncated C2 | (NeuAc2-3)$_{+/-}$Galβ1-3[GlcNAcβ1-6]GalNAcα1-O-Ser/Thr | O-linked | Cancer cells | 7 |
| Truncated C4 | GlcNAcβ1-3[GlcNAcβ1-6]GalNAcα1-O-Ser/Thr | O-linked | Cancer cells | 8 |
| Non-capped type1-C3 | Galβ1-3G1cNAcβ1-3GalNAcα1-O-Ser/Thr | O-linked | Cancer cells | 9 |
| Non-capped type2-C2 | (NeuAc2-3)$_{+/-}$Galβ1-3[Galβ1-4GlcNAcβ1-6]GalNAcα1-O-Ser/Thr | O-linked | Cancer cells | 10 |
| Non-capped type2-C4 | (Galβ1-4)GlcNAcβ1-3[Galβ1-4GlcNAcβ1-6]GalNAcα1-O-Ser/Thr | O-linked | Cancer cells | 11 |
| GalNAcα-Tn | GalNAcα1-3GalNAcα1-O-Ser/Thr | O-linked | Cancer cells | 12 |

TABLE I-continued

Representative mucin-type O-glycan structures on normal and diseased cells[1]

| Name | Hapten Structure (+/−Ser/Thr or artificial linker) | Type of Glycoconjugate | Distribution (main) | No |
|---|---|---|---|---|
| SA-type1-C3 | NeuAcα2-3Galβ1-3GlcNAcβ1-3GalNAcα1-O-Ser/Thr | O-linked | Cancer cells | 13 |
| SLe[a]-C3 | NeuAcα2-3Galβ1-3[Fucα1-4]GlcNAcβ1-3GalNAcα1-O-Ser/Thr | O-linked | Cancer cells | 14 |
| LacDiNAc-C3 | GalNAcβ1-3/4G1cNAcβ1-3GalNAcα1-O-Ser/Thr | O-linked | unknown | 15 |
| LacDiNAc-C2 | Galβ1-3[GalNAcβ1-3/4G1cNAcβ1-6]GalNAcα1-O-Ser/Thr | O-linked | unknown | 16 |
| LacDiNAc-C4 | GalNAcβ1-3/4GlcNAcβ1-3[GalNAcβ1-3/4GlcNAcβ1-6]GalNAcα1-O-Ser/Thr | O-linked | unknown | 17 |

[1]Additional modifications such as capping terminal β3/4Gal residues with Fucα1-2 (blood group H) and Gal(NAc)α1-3 (blood group A,B) are generally produced by normal cells. Modifications such as 3/6-O-SO$_3$ of Gal and GalNAc, 9-O-acetylation of NeuAc, NeuGc instead of NeuAc, may also occur in normal and cancer cells.

In some aspects of the invention, the glycopeptide sequences of the invention may be derived from disease-associated proteins, such as, e.g., a glycoprotein specifically expressed on the cell surface of a cancer cell, but not on the surface of a non-malignant cell, or overexpressed on cancer cell surfaces, e.g., mucin 1 (MUC1) (GenBank Accession Nos. NP_002447 (SEQ ID NO: 1); NP_001018016 SEQ ID NO: 2); NP_001018017 (SEQ ID NO: 3); NP_001037855 (SEQ ID NO: 54); NP_001037856 (SEQ ID NO: 55); and NP_001037857 (SEQ ID NO: 56)); MUC16 (GenBank Accession No. NP_078966 (SEQ ID NO: 57); and mesothelin (MSLN) (GenBank Accession Nos. NP_037536 (SEQ ID NO: 58) and NP_005814 (SEQ ID NO: 59). In some embodiments, the glycoproteins are organ-specific glycoproteins. Examples of such glycoproteins include MUC16 (expressed in the female reproductive tract) and mesothelin, which is specifically expressed in the normal lung, but with cancer expression in ovarian and cervical cancers. Specific examples of other glycoproteins of the invention include, but are not limited to, human proteins predicted from the completed human genome containing one or more serine and/or threonine GalNAc O-glycosylation sites as predicted by the NetOGlyc algorithm.

Non-limiting examples of such proteins include cell membrane receptors such as low-density lipoprotein receptor precursor (LDLR) (GenBank Accesion No. NP_000518) (SEQ ID NO: 67)), very low-density lipoprotein receptor precursor (VLDLR) (GenBank Accession Nos. NP_001018066 (SEQ ID NO: 68) and NP_003374 (SEQ ID NO: 69)), and receptor tyrosine-protein kinase erbB-2 precursor (ERBB2) (GenBank Accession Nos. NP_004439 (SEQ ID NO: 70) and NP_001005862 (SEQ ID NO: 71)); chaperones such as heat shock 70 kDa protein 5 (HSPA5) (GenBank Accession No. NP_005338 (SEQ ID NO: 72) and heat shock 70 kDa protein 8 (HSPA8) (GenBank Accession No. NP_694881) (SEQ ID NO: 73) and NP_006588 (SEQ ID NO: 74); secreted cytokines, growth factors and glycoproteins such as interferon alpha-2 precursor (IFNA2) (GenBank Accession No. NP_000596) (SEQ ID NO: 75), interleukin-2 (IL2) (GenBank Accession No. NP_000577) (SEQ ID NO: 76), and inhibin beta B chain precursor (INHBB) (GenBank Accession No. NP_002184) (SEQ ID NO: 77); proteases such as matrix metalloproteinase-14 precursor (MMP14) (GenBank Accession No. NP_004986) (SEQ ID NO: 78); enzymes such as prostatic acid phosphatase precursor (ACPP) (GenBank Accession Noa. NP_001127666) (SEQ ID NO: 79) and NP_001090 (SEQ ID NO: 80); and mucins such as melanoma cell adhesion molecule (MCAM) (GenBank Accession No. NP_006491) (SEQ ID NO: 81).

In other embodiments, glycopeptide mutants are contemplated for use in the present invention. For example, a peptide library can be generated wherein each amino acid in the peptide sequence around one or more sites for PTM modification (e.g., O-glycosylation) is varied by any combination of the 20 amino acids used in human proteins to form additional peptide sequences (i.e. mutants) with the same PTM motif.

In certain embodiments, the present invention further relates to the design of glycopeptide libraries for screening disease-associated antibodies and/or for identifying disease-associated glycopeptides and/or glycopeptide epitopes. In certain aspects, a glycopeptide library of the invention is provided as a glycopeptide panel for identifying glycopeptides reactive with disease-associated auto-antibodies. A "glycopeptide panel" comprises at least two glycopeptides (or indeed entire glycoproteins) and may be used in an antibody binding assay of the invention. In certain aspects, methods for designing both the sequence of the glycopeptide and the specific site(s) for glycosylation are provided.

Preferably, glycopeptides of the glycopeptide libraries of the invention are from about 4 to about 50 amino acids in length. More preferably, such glycopeptides are from about 4 to about 25 amino acid residues in length.

In certain aspects, peptides are designed as fragments of a glycoprotein. A random peptide library encompassing peptides having between about 4 and about 50 amino acids, is provided, wherein each amino acid in each peptide is varied by all 20 amino acids used in human proteins to form different peptide sequences. These random peptides are PTM-modified, e.g., O-glycosylated, on at least one amino acid residue. In other aspects, the peptide library comprises peptides covering all serine and threonine residues in the predicted human protein sequences. In yet another aspect, peptides of the glycopeptide libraries comprise sequences derived from disease-associated proteins and/or organ-specific proteins, as described, supra.

In certain embodiments of the invention, a peptide suitable for testing is a potential acceptor of GalNAc O-glycosylation by polypeptide GalNAc-transferases if: 1) the peptide is a sequence derived from the human proteome, wherein the human proteome may be predicted from the human genome; and 2) the peptide comprises one or more serine and/or threonine residues. Preferably, such peptides are derived from proteins that have a signal sequence. It is also preferred that such peptides have sequences that, in vitro, serve as substrates for one or more human polypeptide GalNAc-transferases, such as, e.g., GalNAc-T1, T2, T3, or T4. The initiating enzymes for other types of O-glycosylation that attaches the first sugar residue to Serine and Threonine residues of polypeptides have been cloned and expressed recombinantly and hence these types of modifications are amiable to the same strategy for testing (Essentials of Glycobiology (2$^{nd}$ edtion, eds A. Varki, Cummings, Esko, Freeze, Stanley Bertozzi, Hart, Etzler. CSH Press 2009).

In certain aspects, it is preferred that the glycopeptides of the invention comprise sequences predicted by the NetOGlyc algorithm. The NetOGlyc algorithm has been developed to predict sites and proteins modified by O-glycosylation and this has been postulated to have a positive prediction rate of 76% (Julenius et al. 2005).

In other embodiments, peptides may be modified with other PTM modifications.

Glycopeptide Synthesis

In some aspects of the invention, the peptide sequence of the glycopeptides of the invention can be synthesized using standard chemical synthesis [Meldal M, Bock K. A general approach to the synthesis of O- and N-linked glycopeptides. Glycoconj J. 1994; 11(2):59-63]. For example, GalNAcα-Ser/Thr-Fmoc, GlcNAcα-Ser/Thr-Fmoc, Manα-Ser/Thr, and Glcβ-Ser/Thr amino acids are commercially available (Sussex Inc (Canada)), and may be incorporated into the peptides during synthesis. The glycopeptides of the invention may be synthesized with and without an N-terminal linker for printing on epoxy or NHS-activated glass slides, respectively. In certain embodiments, glycopeptides may also be synthesized directly on microarray slides ("spot synthesis"). In other embodiments, peptides are previously synthesized and then immobilized or used in solution, according to a method of the present invention.

In certain aspects, the synthesized peptides or glycopeptides are O-glycosylated or further O-glycosylated using enzymatic synthesis of O-glycans at specific sites to form glycopeptides (Tarp and Clausen 2008).

In certain aspects of the present invention, the peptides may be glycosylated by a number of different methods, such as e.g., on-slide glycosylation, in solution glycosylation, or in vivo, e.g., by recombinant expression in appropriate host cells (Tarp et al. Glycobiology 2007).

Glycosylation may be achieved using one or more recombinant glycosyltransferases. such as, e.g., recombinant polypeptide GalNAc-transferases (e.g. GalNAc-T2, -T3 and -T4). See, e.g., U.S. Pat. No. 5,876,716 by Hansen and U.S. Pat. No. 6,465,220 by Hassan; see also, Bennett et al. 1998; Bennett et al. 1996; and White et al. 1995.

Further expansion may also be achieved using a recombinant sialyltransferase, ST6GalNAc-II, to produce STn glycoforms (structure no. 2, Table I) of the GalNAc glycopeptides. T glycoforms may be produced by a recombinant *Drosophila* core1 β3galactosyltransferase, truncated core3 glycoforms (structure no. 6, Table I) may be produced using a recombinant human β3GlcNAc-transferase (Iwai et al. 2002), and non-capped type1-core3 glycoforms (structure no. 9, Table I) may be produced using β3Gal-T5 (see, U.S. Pat. No. 7,332,279).

In other aspects, the glycopeptides and/or glycoproteins of the invention may be derived from recombinant or isolated glycopeptides or glycoproteins and further glycosylated or modified according to the methods of the present invention. For example, commercially available glycoprotein arrays (available, e.g., from Invitrogen), may be treated with exoglycosidases, e.g., neuraminidase, βgalactosidase, βN-acetylglucosaminidase and other enzymes, in order to expose cancer-associated glycans, e.g., Tn or T, to form glycopeptides according to the present invention.

In certain aspects of the invention, the O-glycan is preferably positioned in the center of the peptide. While not intending to be bound by a specific theory, positioning the O-glycan in the center of the peptide may facilitate proper presentation of the O-glycan for specific antibody binding to a glycopeptides epitope. In certain aspects, for example, in a glycopeptide of 20 amino acid residues in length, the O-glycan is preferably attached to a serine or threonine amino acid residue placed at a site from about residue 6 to about residue 15 and more preferably from about residue 8 to about residue 13. For example, in the present Examples, glycopeptides were designed with a single GalNAc at position 12 (of the 20-mer) to allow optimal exposure of peptide sequence flanking the O-glycan, taking into consideration that the glycopeptides will be covalently linked primarily through the N-terminal amino acid.

In certain aspects, the O-glycans to be presented on a glycopeptide library of the invention may include all known O-glycan structures. In preferred embodiments, the glycopeptides comprise glycans known to be disease-associated, such as Tn, STn, T, Truncated C3, Truncated C2, Truncated C4, non-capped type1-C3, non-capped type2-C2, non-capped type2-C4, GalNAcα-Tn, SA-type1-C3, SLea-C3, LacDiNAc-C3, LacDiNAc-C2, and LacDiNAc-C4 (see Table I for additional non-limiting examples of such glycans). Further the O-glycans may be substituted with sulfation or other immunogenic substitutions including acetylation and artificial chemical groups.

Screening Assays

In certain embodiments, the present invention provides methods for identifying glycopeptides and/or glycopeptide epitopes reactive with disease-associated auto-antibodies using an assay comprising one or more glycopeptide panels. Preferably, such auto-antibodies bind glycopeptide epitopes through recognition of both the peptide portion and the glycan portion, but not through recognition of either the peptide or the glycan alone. The panel is contacted with a sample containing the disease-associated antibodies (e.g., sera obtained from an individual with the disease).

In a specific embodiment, the invention provides a method for identifying glycopeptides reactive with cancer-associated auto-antibodies, wherein the method comprises: (a) providing a panel comprising glycopeptides having a peptide portion and a glycan portion; (b) contacting the panel with an antibody-containing sample from a patient with cancer; and (c) identifying glycopeptides in the panel that (i) are selectively recognized by antibodies in the sample, but not by antibodies in a control sample, and (ii) are recognized by such antibodies in the sample through recognition of both the peptide portion and the glycan portion, but not through recognition of either the peptide or the glycan alone.

Non-limiting examples of suitable antibody-containing samples for the assays of the present invention include serum, plasma, body fluids such as milk, saliva, mucosal secretions, feces, urine, cells and tissues, and any antibody preparations thereof.

Further, in order to develop the glycopeptide screening assays of the present invention, a control sample is used. By "control sample", it is meant a sample containing pooled sera obtained from apparently disease-free or healthy individuals (i.e., individuals who do not have the disease-associated antibodies in their serum because they do not have the relevant disease), or, it is meant multiple control samples, wherein each sample is obtained from a single apparently healthy (disease-free) individual, and then data obtained in the assay for the tested control samples are compared in order to exclude any samples from control individuals who are suspected to in fact not be healthy, based on the presence of auto-antibodies not present in a statistically significant fraction of the control population.

In certain aspects, the present invention provides methods for identifying cancer-associated glycopeptide epitopes, wherein the epitope includes both part of the glycan of the glycopeptide and part of the peptide amino acid sequence. Such methods can comprise the following steps: (a) providing a panel comprising glycopeptides having a peptide portion and a glycan portion; wherein the peptide amino acid sequences of the glycopeptides are serially shifted 1-5 residues in either direction, to provide a series of overlapping peptide sequences; (b) contacting the panel with an antibody-containing sample from a patient with cancer; (c) identifying glycopeptides in the panel that (i) are selectively recognized by antibodies in the sample, but not by antibodies in a control sample, and (ii) are recognized by such antibodies in the sample through recognition of both the peptide portion and the glycan portion, but not through recognition of either the peptide or the glycan alone; and (d) mapping the minimal glycopeptide epitope based on the pattern of antibody binding to the overlapping glycopeptide sequences.

"Epitope mapping" may be carried out as follows: A glycopeptide epitope comprising e.g., a 20-mer glycopeptide with a single glycan attached to position 12 can be "mapped" in terms of peptide sequence requirement by synthesis of a panel of 20-mer glycopeptides in which each amino acid around the glycan site is modified one by one to an amino acid different from the one present in the identified glycopeptide, e.g. alanine or valine. Analysis of antibody binding to this panel of "walking" alanine or valine residues through the peptide sequence will demonstrate which residues abrogate binding, and thus provide information of the necessary peptide sequence backbone around the glycosylation site required for antibody binding.

In certain aspects of the invention, the minimum glycopeptide epitope is preferably about 2 to about 7 amino acid residues in length, but can extend to up to about 15 residues, and comprises a portion of an O-glycan modifying the glycopeptide epitope. In certain embodiments, the minimal glycopeptide epitope spans about 3 to about 4, about 2 to about 3, or about 1 to about 2 amino acid residues on each side of the O-glycan that is part of the minimal epitope identified by the methods of the present invention. In other embodiments, a greater number of amino acids may be present on one side of the O-glycan compared to the number of amino acids of the minimal epitope on the other side of the O-glycan. The minimum glycopeptide epitope can be, for example, a "minimum cancer-associated glycopeptide epitope," which is the minimum glycopeptide epitope identified by the methods of the present invention to be specifically recognized by a cancer-associated auto-antibody.

In certain embodiments, the epitope structure of the glycopeptide epitopes identified by the present methods is determined by mass spectrometry.

In some aspects, determining whether glycopeptides and/or glycopeptide epitopes are selectively recognized by antibodies in a sample through recognition of both the peptide portion and the glycan portion, wherein the antibodies do not recognize either portion alone, may be achieved as follows: an additional panel may be provided, in which the unglycosylated forms of the glycopeptides are provided (i.e., the corresponding peptides) and antibody binding is determined. In order for a glycopeptide to be selectively recognized by an antibody in the sample, antibody binding to the corresponding peptide should be partially or preferably completely abrogated. Preferably, antibody binding to the corresponding peptide is diminished by at least about 40%, preferably at least about 50%, more preferably at least about 60%, even more preferably at least about 70%, still more preferably at least about 80%, more preferably at least about 85%, still more preferably at least about 90%, and most preferably 95% to 100% compared to antibody binding to the glycopeptide.

In other aspects of the present invention, methods of determining the presence of auto-antibodies binding O-glycopeptides, may also comprise the step of contacting the panel with a peptide inhibitor in order to exclude antibodies that recognize the non-glycosylated form of the glycopeptide. Peptide inhibitors are typically a peptide of the same amino acid sequence as the glycopeptide, however, without any glycosylations.

In other embodiments, antibodies that recognize only the hapten glycan or the glycan-conjugated to a different peptide or artificial carrier may be excluded, in order to prevent identification of epitopes that consist only of the glycan hapten. This can be achieved in several ways. For example, in certain embodiments, hapten-specific antibodies may be removed from the sample prior to analysis.

In some embodiments, hapten-specific antibodies may be removed by affinity chromatography with an appropriate resin with covalently linked carbohydrate haptens, or by inhibition with carbohydrate haptens in solution during binding assays. An example of preferable resin is GalNAc-Sepharose or other appropriate resins that would be able to bind anti-Tn hapten antibodies. Other preferable resins are GlcNAc-Sepharose, Man-Sepharose, Glc-Sepharose or Fuc-Sepharose and without limitations corresponding di- and trisaccharides in the biosynthetic pathways bound resins.

In other embodiments, hapten-specific antibodies may excluded from binding to glycopeptides in the binding assays of the present invention using a carbohydrate inhibitor. In some embodiments, the carbohydrate inhibitor comprises a normal occurring O-glycan such as sialylated or fucosylated core 2, 3, or 4 O-glycan, as is typically present in normal cells. In some aspects, the carbohydrate inhibitor may be Tn, STn, T or other truncated O-glycan structures based on core 3 or 4. Also preferred are polyvalent PAA (polyacrylamide) conjugates (GlycoTech, US) of the aforementioned carbohydrates. Still in another embodiment, the carbohydrate inhibitor is a monosaccharide such as GalNAc, GlcNAc, Gal, Glc, Fuc, Man, Xyl and NeuAc. It will be apparent to the skilled artisan that other combinations of carbohydrates will have the same effect.

The above-described methods, as well as other methods that may be readily determined by a skilled artisan and used to achieve the same effect, may be used to exclude antibodies in a sample that do not specifically recognize the glycopeptide (i.e., through both the peptide and the glycan). In certain embodiments of the invention, exclusion of such antibodies from the analysis is necessary in order to identify the glycopeptides and glycopeptide epitopes that are specifically recognized by disease-associated antibodies.

In certain embodiments, a peptide inhibitor and/or an O-glycan inhibitor may be immobilized on a solid support, which is used to remove antibodies that interact with the peptide inhibitor and/or with the O-glycan carbohydrate inhibitor from a sample, prior to use of the sample according to a method of the present invention.

In some aspects, the screening assays of the present invention involve immobilized glycopeptides; however, in solution assays such as polarization, inhibition and competitive binding assays are also contemplated for use in the present invention. [See, e.g., Smith D S, Eremin S A. Fluorescence polarization immunoassays and related methods for simple, highthroughput screening of small molecules. Anal Bioanal Chem. 2008; 391(5):1499-507.]

Non-limiting examples of screening assays involving immobilized glycopeptides contemplated for use in the present invention include antibody-binding assays, such as enzyme-linked immunosorbent assay (ELISA), multiplex bead arrays (see, Elshal et al., (2006) Methods; 38(4):317-323); BiaCore SPR analysis where binding affinities can be evaluated and microarray platforms.

In a preferred embodiment, glycopeptide libraries of the invention are immobilized on microarray slides. The glycopeptides may be printed on microarray slides, such as, e.g., Corning, Scineion or Nexterion® Slide H or Schott Nexterion® Slide H MPX 16 (Schott AG, Mainz, Germany) by JPT (Germany). Printing may be carried out using MicroGrid, ArrayIT or similar according to the methods described in (Blixt O, Head S, Mondala T, Scanlan C, Huflejt M E, Alvarez R, Bryan M C, Fazio F, Calarese D, Stevens J, Razi N, Stevens D J, Skehel J J, van Die I, Burton D R, Wilson I A, Cummings R, Bovin N, Wong C H, Paulson J C. Printed covalent glycan array for ligand profiling of diverse glycan binding proteins. Proc Natl Acad Sci USA. 2004; 101(49):17033-8)

Microarray slides of the invention may also be prepared by companies such as Schott (Louisville, Ky.), ArrayIt Corp. (Sunnyvale, Calif.), or Scineon (Germany).

In certain embodiments, assays for large scale screening include, e.g., multiplex bead or array formats where many targets can be assayed simultaneously with very little consumption of antibody. For example, a small volume (50 μl) of an antibody-containing sample (e.g. serum or diluted serum) may be incubated with a solution of beads, wherein each bead is coated with a specific glycopeptide, and each bead possesses a distinguishing characteristic (e.g., size) that allows it to be differentiated from other beads in the sample. If an antibody is present in the sample that recognizes a glycopeptide on one of the beads, it will bind to the bead. Then, specific binding of antibodies to each glycopeptide in the sample may be detected using a detecting reagent, such as, e.g., biotinylated anti-Ig antibody followed by fluorescently-labeled streptavidin. The concentration of antibody in the sample that is specific for each glycopeptide on the bead may then be quantified using a bead analyzer, such as, e.g., the Luminex® 200™ System (Invitrogen).

In yet another embodiment of the invention, the detection of auto-antibodies can be limited to distinct human Ig isotypes and subclasses. Most human natural carbohydrate antibodies are of IgM isotype and it is the detection of auto-antibodies of IgG isotype and subclasses is preferred. More specifically, detection of binding of human IgG antibodies, or IgG1, 2, 3, and 4 individually, with appropriate anti-human antibodies avoid most reactivity with truncated O-glycan haptens such as Tn, STn, T core3, and other truncated structures to which IgM antibodies are found in control samples.

Methods of Diagnosing

In some aspects, the present invention provides methods for diagnosing a patient with a disease. For example, disease-associated glycopeptides and glycopeptide epitopes identified by the methods of the present invention may be used for detection of disease-associated auto-antibodies with the purpose of determining diagnosis and/or prognosis.

For example, in certain embodiments, a patient may be diagnosed as having cancer or as not having cancer, based on the presence or absence, respectively, of specific, cancer-associated glycopeptide-reactive auto-antibodies. In a specific embodiment, the method comprises contacting an antibody-containing sample from a patient with a panel comprising peptides, wherein at least a plurality of the peptides are glycopeptides. Further, each glycopeptide comprises a glycopeptide epitope that has been previously determined (i) to be selectively recognized by a subset of antibodies in sera from cancer patients, which subset recognizes neither (a) the corresponding naked peptides of said panel when not glycosylated; nor (b) the corresponding glycan when not bound to said peptide; and (ii) not to be recognized by antibodies in control sera. It is then determined if antibodies in the sample are bound to glycopeptides of said panel; and concluded either that the patient has cancer if the sample comprises antibodies that bind to at least one of the glycopeptides in the panel; or that the patient does not have cancer if the sample does not comprise antibodies that bind to at least one glycopeptide in the panel.

In certain aspects, the specific type of cancer that may be diagnosed or treated by a method of the present invention without limitation may be selected from the group consisting of breast cancer, colon cancer, ovarian cancer, cervical cancer, pancreatic cancer, prostatic cancer, liver cancer, kidney cancer, brain cancer, hematological cancers, testis cancer, head and neck cancers, and lung cancer.

In yet another embodiment, the diagnostic panel comprises glycopeptides comprising one or more and preferably at least 8 of the amino acid sequences selected from the group consisting of SEQ ID NOs. 15, 36, 49, and 82-146.

In yet another specific embodiment, the diagnostic panel comprises glycopeptides comprising one or more of the amino acid sequences selected from the group consisting of SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146). Furthermore, these glycopeptides may be O-glycosylated at one or more sites according to the methods of the present invention.

In yet another embodiment, the diagnostic panel comprises at least 8 glycopeptides, for example between about 8 and about 30 glycopeptides, such as 10, 12, 15, or 20 glycopeptides. A number of glycopeptides in excess of 30 is also within the invention. The upper limit of glycopeptides in a panel is limited by practical considerations (e.g., how many glycopeptides can fit on a substrate) or cost-benefit considerations. Preferably the glycopeptides are selected from the group consisting of SEQ ID NOs 15, 36, 49, and 82-146.

In yet other aspects, a patient may be diagnosed as having an autoimmune disease. In certain embodiments, the autoimmune disease is selected from the group consisting of coeliac disease, type I diabetes, multiple sclerosis, thyroiditis, Grave's disease, systemic lupus erythematosus, scleroderma, psoriasis, rheumatoid arthritis, alopecia greata, ankylosing spondylitis, Churg-Strauss Syndrome, autoimmune hemolytic anemia, autoimmune hepatitis, Behcet's disease, Crohn's disease, dermatomyositis, glomerulonephritis, Guillain-Barre syndrome, inflammatory bowel disease (IBD), lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis.

Thus, in some embodiments, a diagnostic panel of the invention comprises glycopeptide epitopes determined by the methods of the present invention to be associated with an autoimmune disease. For example, in certain embodiments, a patient may be diagnosed as having an autoimmune disease or as not having an autoimmune disease, based on the presence or absence, respectively, of specific, autoimmune disease-associated glycopeptide-reactive auto-antibodies. In a specific embodiment, the method comprises contacting an antibody-containing sample from a patient with a panel comprising peptides, wherein at least a plurality of the peptides are glycopeptides. Further, each glycopeptide comprises a glycopeptide epitope that has been previously determined (i) to be selectively recognized by a subset of antibodies in sera from patients with a specific autoimmune disease, which subset recognizes neither (a) the corresponding naked peptides of said panel when not glycosylated; nor (b) the corresponding glycan when not bound to said peptide; and (ii) not to be recognized by antibodies in control sera. It is then determined if antibodies in the sample are bound to glycopeptides of said panel; and concluded either that the patient has the autoimmune disease if the sample comprises antibodies that bind to at least one of the glycopeptides in the panel; or that the patient does not have the autoimmune disease if the sample does not comprise antibodies that bind to at least one glycopeptide in the panel.

Preparation of Antibodies

Other aspects of the present invention are antibodies prepared using one or more glycopeptides identified using the methods of the present invention, methods for preparation of these antibodies, and the use of such antibodies in therapy and diagnosis.

Yet another aspect of the present invention is a method for the preparation of hybridoma cells, which secrete monoclonal antibodies specific for the glycopeptides of the invention. One such method involves immunizing a suitable mammal with a glycopeptide of the invention; fusing antibody-producing cells of the mammal with cells of a continuous cell line; the hybrid cells obtained in the fusion are cloned; and cell clones secreting the desired antibodies are selected.

Still another aspect is a monoclonal antibody selected from the group consisting of: a monoclonal antibody produced by the hybridoma cells prepared by the method described above; and a monoclonal antibody prepared by molecular display techniques, such as mRNA display, ribosome display, phage display and covalent display against a glycopeptide of the invention.

For preparation of monoclonal antibodies, any technique that provides for the production of antibody molecules by continuous cell lines in culture may be used. These include but are not limited to the hybridoma technique originally developed by Kohler and Milstein (Nature, 1975; 256:495-497), as well as the trioma technique, the human B-cell hybridoma technique (Kozbor et al., Immunology Today, 1983; 4:72, Cote et al., Proc. Natl. Acad. Sci. U.S.A., 1983; 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec., 1989).

According to the invention, techniques described for the production of single chain antibodies (U.S. Pat. Nos. 5,476,786 and 5,132,405 to Huston; U.S. Pat. No. 4,946,778) can be adapted to produce glycopeptide-specific single chain antibodies. Indeed, these genes can be delivered for expression in vivo to, e.g., express a glycopeptide-specific antibody. An additional embodiment of the invention utilizes the techniques described for the construction of Fab expression libraries (Huse et al., Science, 1989; 246:1275-1281) to allow rapid and easy identification of monoclonal Fab fragments with the desired specificity for a glycopeptide or glycopeptide epitope of the invention.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In other embodiments, alternative techniques such as mRNA display, ribosome display, phage display and covalent display may also be used. These are all display techniques where a peptide library is selected against the glycopeptide. Such techniques can e.g. be used to identify humanized or fully human antibodies.

In a preferred embodiment, the monoclonal antibody binds an O-glycoprotein containing the O-glycopeptide epitope on cancer cells but not on a non-malignant counterpart.

In another preferred embodiment, the monoclonal antibody binds preferentially to the O-glycoprotein that is aberrantly glycosylated and expressed on cancer cells.

In still another embodiment, the monoclonal antibody binds to or at least interacts directly with the O-glycopeptide.

In a preferred embodiment, the antibody prepared using a glycopeptide of the invention is humanized or fully human, such as to decrease the immunogenicity of the antibody in humans. This is typically desirable if the antibody is used as a therapeutic. However, in some situations a rapid clearance may be desired, wherefore non-humanized antibodies are also of interest as therapeutics. One such situation can, e.g., be when administering antibody conjugates where antibodies are coupled to toxins or radioisotopes. Such conjugated antibodies should either find their target rapidly or be cleared as they have a general toxic effect. Thus, one embodiment of the invention is conjugated antibodies. Non-limiting examples of antibody conjugates include radioisotopes, such as $^{131}$I, $^{90}$Y, $^{177}$Leutitium ($^{177}$Lu) and $^{67}$Copper ($^{67}$Cu); toxins, such as the fungal toxin maytansanoid (DM-1); and antibiotics, such as e.g., calicheamicin [See, Ross et al. Antibody-based therapeutics: Focus on prostate cancer. Cancer and Metastasis Reviews 24: 521-537, 2005].

Compositions and Uses

In certain embodiments, the present invention provides compositions comprising one or more disease-associated glycopeptides and/or glycopeptide epitopes identified by the methods of the present invention. In certain aspects, such disease-associated glycopeptides comprise epitopes specifically recognized and bound by disease-associated antibodies.

In a specific embodiment, a composition of the invention comprises one or more of a glycoprotein or glycopeptide comprising an amino acid sequence selected from the group consisting of SEQ IDs 15, 36, 49, and 82-146. Preferably, the composition comprises one or more of a glycoprotein or glycopeptides comprising an amino acid sequence selected from the group consisting of SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGG-PKDHPLTCDDPRFQA (SEQ ID NO: 109); PGTSTTPSQP-NSAGVQDTEM (SEQ ID NO: 116); TKTDASSTHH-STVPPLTSSN (SEQ ID NO: 132); HDVETQFNQYKTEAASRYNL (SEQ ID NO: 134); ASRYNLTISDVSVSDVPFPF (SEQ ID NO: 135); VPVTR-PALGSTTPPAHDVTS (SEQ ID NO: 145); and SLASQAT-DTFSTVPPTPPSI (SEQ ID NO: 146). In certain embodiments, such glycoproteins or glycopeptides are further modified at at least one amino acid residue, with an O-glycan. Preferably, the amino acid residue is serine or threonine residue.

In some aspects, the invention provides methods for eliciting an immune response in an individual, wherein the immune responses is specific for one or more glycopeptides or glycoproteins identified by the methods of the present invention.

One aspect of the invention is a method of treating cancer or an autoimmune disease comprising administering a pharmaceutical composition of the invention. In a specific embodiment, a cancer patient is treated by eliciting an anti-cancer immune response that attacks cancer cells (e.g., tumors). In any of the aspects of the invention, the immune response elicited by a pharmaceutical composition of the invention may be an adaptive T and/or B cell response (e.g., either a cytotoxic T cell response or an antibody response, or both) directed against the cancer cells, which results in reduction or elimination of the cancer cells.

"Treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms.

The benefit to an individual to be treated is either statistically significant or at least perceptible to the patient or to the physician.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one composition of the invention, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine.

Pharmaceutical Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin (1990, Mack Publishing Co., Easton, Pa. 18042).

Vaccines

In certain aspects, a disease-associated glycopeptide or glycoprotein of the present invention is provided in a vaccine. Thus, in certain aspects, such a disease-associated glycopeptide or glycoprotein is provided as an "immunogen" for inducing an immune response. In some aspects, a vaccine of the present invention is useful for treating cancer by inducing an "anti-cancer immune response." Preferably, a vaccine of the present invention in effective for inducing an adaptive immune response that selectively target cancer cells and has minimal reactivity with normal cells.

In certain embodiments, the glycopeptide epitopes identified by the methods of the present invention are targets for spontaneously-induced human auto-antibodies. Thus, it is evident that these epitopes are not generally covered by immunological tolerance. Accordingly, in certain aspects of the invention, a vaccine comprising a glycopeptide immunogen identified by the present methods does not require an adjuvant.

In other embodiments, a vaccine comprising a glycopeptide immunogen of the invention may additionally contain adjuvants to induce or enhance the desired immune response, such as, e.g., an anti-cancer immune response. Exemplary adjuvants include, but are not limited to, cholera toxin, fragments and mutants or derivatives with adjuvant properties, *E. coli* heat-labile enterotoxin, fragments and mutants or derivatives with adjuvant properties, oil-in-water and water-in-oil emulsions, toll-like receptor ligands such as muramyl dipeptide, *E. coli* LPS, oligonucleotides comprised of unmethylated DNA, poly I:C, lipoteichoic acid, peptidoglycan. Enterotoxins and their adjuvant active derivatives such as cholera toxin, heat-labile *E. coli* enterotoxin, pertussis toxin, shiga toxin and analogs. Other adjuvants can be used such as complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and *Corynebacterium parvum*. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Where the vaccine is intended for use in human subjects, the adjuvant should be pharmaceutically acceptable.

Formulations

The compositions, vaccines and formulations of the present invention may comprise pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. See, e.g., Remington's Pharmaceutical Sciences, 18th Ed. (1990, Mack Publishing Co., Easton, Pa. 18042) pages 1435 1712 which are herein incorporated by reference.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Administration and Dosage

The compositions (e.g., pharmaceutical or vaccine compositions) and formulations of the present invention can be administered topically, parenterally, orally, by inhalation, as a suppository, or by other methods known in the art. The term "parenteral" includes injection (for example, intravenous, intraperitoneal, epidural, intrathecal, intramuscular, intraluminal, intratracheal or subcutaneous). The preferred routes of administration are subcutaneous and intravenous.

The compositions and formulations of the present invention may be administered to an animal, preferably a mammal, and most preferably a human.

The dosage of the compositions or formulations of the present invention will vary widely, depending upon the nature of the disease, the patient's medical history, age, body weight, sex, sensitivity, the frequency of administration, the manner and route of administration, the clearance of the agent from the host, dosage period, drugs used in combination, and the like. The initial dose may be larger, followed by smaller maintenance doses.

For any composition or formulation used in the methods of the invention, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical studies.

Toxicity and therapeutic efficacy of the compositions, vaccines, and formulations of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

The data obtained from the animal studies can be used in formulating a range of doses for use in humans. The therapeutically effective doses of in humans lay preferably within a range of circulating concentrations that include the $ED_{50}$ with little or no toxicity. The dosage can vary within this range depending upon the dosage form employed and the route of administration utilized. Ideally, a single dose of each drug should be used daily.

The compositions of the invention will typically contain an effective amount of the compositions for achieving the desired effect. As used herein, an "effective amount of a glycopeptide" is an amount that elicits the desired response upon administration, e.g., an amount that elicits an immune response in a mammal.

Administration of the compositions or formulations of the invention may be once a day, twice a day, or more often, but frequency may be decreased during a maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

In certain embodiments of the invention, use of an appropriate vaccine design and immunization scheme will therefore elicit immunity to a glycopeptide epitope of the immunogen and efficiency of the immunization can be monitored by immunoassays, e.g., by detecting the presence of immunogen-specific antibodies in an antibody-containing sample from an immunized patient by ELISA or other assay suitable for detecting antigen-specific antibodies.

Keeping the above description in mind, typical dosages of the glycopeptide-containing compositions of the invention are 5-50 µg glycopeptides conjugated to e.g. KLH (keyhole-Limpet Hemocyanin) given subcutaneously 3-5 times with 2-3 weeks apart. Maintenance vaccine could be extended with monthly or bi-monthly dosing for extended periods.

Kits

In some embodiments, the invention relates to a kit comprising one or more glycopeptides identified by the present methods. In certain aspects the kit comprises a panel of two or more glycopeptides identified by the present methods. In other aspects, the kit further provides instructions for use. In a specific embodiment, the kit provides a diagnostic assay for diagnosing cancer, comprising a panel of cancer-associated glycopeptides, assay buffers, and instructions for use.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

EXAMPLES

The present invention is described further below in working examples which are intended to further describe the invention without limiting the scope therein.

Example 1

Development of a Cancer-Associated O-Glycopeptide Library for Microarray Display GalNAc-Ser/Thr-Fmoc amino acids were synthesized by Sussex Inc (Canada) and 20-mer peptides and corresponding glycopeptides with one GalNAc O-glycan synthesized and printed on epoxy activated glass slides by JPT Peptide Technologies (Berlin, Germany). A total of 48 paired peptides and 48 GalNAc-glycopeptides were synthesized and printed (Table II).

TABLE II

Synthetic 96 paired glycopeptide 20-mer library derived from confirmed O-glycoproteins*

| SEQ ID NO: | Peptide No. | |
|---|---|---|
| 4 | 1 | TSAPDTRPAPGSTAPPAHGV |
| 4 | 2 | TSAPDTRPAPG_S_TAPPAHGV |
| 5 | 3 | SAPDTRPAPGSTAPPAHGVT |
| 5 | 4 | SAPDTRPAPGS_T_APPAHGVT |
| 6 | 5 | PGSTAPPAHGVTSAPDTRPA |
| 6 | 6 | PGSTAPPAHGV_T_SAPDTRPA |
| 7 | 7 | GSTAPPAHGVTSAPDTRPAP |
| 7 | 8 | GSTAPPAHGVT_S_APDTRPAP |
| 8 | 9 | PPAHGVTSAPDTRPAPGSTA |
| 8 | 10 | PPAHGVTSAPD_T_RPAPGSTA |
| 9 | 11 | FYLAMPFATPMEAELARRSL |
| 10 | 12 | KFSEFWDLDPEVRPTSAVAA |
| 11 | 13 | PLVEQGRVAATVGSLAGQP |
| 11 | 14 | PLVEQGRVAA_T_VGSLAGQP |
| 12 | 15 | LWSLCWSLAIATPLPPTSAH |
| 12 | 16 | LWSLCWSLAIA_T_PLPPTSAH |
| 13 | 17 | LEACVIQGVGVTETPLMKED |
| 13 | 18 | LEACVIQGVGV_T_ETPLMKED |
| 14 | 19 | KKWVQDSMKYLDQKSPTPKP |
| 15 | 20 | SHHSDESDELVTDFPTDLPA |
| 15 | 21 | SHHSDESDELV_T_DFPTDLPA |
| 16 | 22 | DESDELVTDFPTDLPATEVF |
| 16 | 23 | DESDELVTDF_P_TDLPATEVF |
| 17 | 24 | FPTDFPTDLPATEVFTPVVP |
| 17 | 25 | FPTDFPTDLPA_T_EVFTPVVP |
| 18 | 26 | FPTDLPATEVFTPVVPTVDT |
| 18 | 27 | FPTDLPATEVF_T_PVVPTVDT |
| 19 | 28 | PATEVFTPVVPTVDTYDGRG |
| 19 | 29 | PATEVFTPVVP_T_VDTYDGRG |
| 20 | 30 | PGAQGLPGVGLTPSAAQTAR |
| 20 | 31 | PGAQGLPGVGL_T_PSAAQTAR |
| 21 | 32 | RGETRCEQDRPSPTTAPPAP |
| 21 | 33 | RGETRCEQDRP_S_PTTAPPAP |
| 22 | 34 | ETRCEQDRPSPTTAPPAPPS |
| 22 | 35 | ETRCEQDRPSP_T_TAPPAPPS |
| 23 | 36 | TRCEQDRPSPTTAPPAPPSP |
| 23 | 37 | TRCEQDRPSP_T_TAPPAPPSP |
| 24 | 38 | PSPTTAPPAPPSPSPSPVPK |
| 24 | 39 | PSPTTAPPAPP_S_PSPSPVPK |
| 25 | 40 | PTTAPPAPPSPSPSPVPKSP |
| 25 | 41 | PTTAPPAPPSP_S_PSPVPKSP |
| 26 | 42 | TAPPAPPSPSPSPVPKSPSV |
| 26 | 43 | TAPPAPPSPSP_S_PVPKSPSV |
| 27 | 44 | STNEFLCDKDKTSTVAPTIH |
| 27 | 45 | STNEFLCDKDK_T_STVAPTIH |
| 28 | 46 | NEFLCDKDKTSTVAPTIHTT |
| 28 | 47 | NEFLCDKDKTS_T_VAPTIHTT |
| 29 | 48 | CDKDKTSTVAPTIHTTVPSP |
| 29 | 49 | CDKDKTSTVAP_T_IHTTVPSP |
| 30 | 50 | DKTSTVAPTIHTTVPSPTTT |
| 30 | 51 | DKTSTVAPTIH_T_TVPSPTTT |
| 31 | 52 | KTSTVAPTIHTTVPSPTTTP |
| 31 | 53 | KTSTVAPTIHT_T_VPSPTTTP |
| 32 | 54 | TVAPTIHTTVPSPTTTPTPK |
| 32 | 55 | TVAPTIHTTVP_S_PTTTPTPK |
| 33 | 56 | APTIHTTVPSPTTTPTPKEK |
| 33 | 57 | APTIHTTVPSP_T_TTPTPKEK |
| 34 | 58 | PTIHTTVPSPTTTPTPKEKP |
| 34 | 59 | PTIHTTVPSPT_T_TPTPKEKP |
| 35 | 60 | TIHTTVPSPTTTPTPKEKPE |
| 35 | 61 | TIHTTVPSPTT_T_PTPKEKPE |
| 36 | 62 | TPTPKEKPEAGTYSVNNGND |
| 36 | 63 | TPTPKEKPEAG_T_YSVNNGND |
| 37 | 64 | ACLAVSAGPVPTPPDNIQVQ |
| 37 | 65 | ACLAVSAGPVP_T_PPDNIQVQ |
| 38 | 66 | RRAVLPQEEEGSGGGQLVTE |
| 38 | 67 | RRAVLPQEEEG_S_GGGQLVTE |
| 39 | 68 | LNAVNNSLTPQSTKVPSLFE |
| 39 | 69 | LNAVNNSLTPQ_S_TKVPSLFE |
| 40 | 70 | NAVNNSLTPQSTKVPSLFEF |
| 40 | 71 | NAVNNSLTPQS_T_KVPSLFEF |
| 41 | 72 | TFVLSALQPSPTHSSSNTQR |
| 41 | 73 | TFVLSALQPSP_T_HSSSNTQR |
| 42 | 74 | RQGWALRPVLPTQSAHDPPA |
| 42 | 75 | RQGWALRPVLP_T_QSAHDPPA |
| 43 | 76 | QKKAKNLDAITTPDPTTNAS |
| 43 | 77 | QKKAKNLDAIT_T_PDPTTNAS |
| 44 | 78 | FLSLSQGQESQTELPNPRIS |
| 44 | 79 | FLSLSQGQESQ_T_ELPNPRIS |
| 45 | 80 | LSLALVTNSAPTSSSTKKTQ |
| 45 | 81 | LSLALVTNSAP_T_SSSTKKTQ |
| 46 | 82 | LISPLAQAVRSSSRTPSDKP |
| 46 | 83 | LISPLAQAVRS_S_RTPSDKP |
| 47 | 84 | DDENTAQFVHVSESFPHPGF |
| 47 | 85 | DDENTAQFVHV_S_ESFPHPGF |
| 48 | 86 | SESFPHPGFNMSLLENHTRQ |
| 48 | 87 | SESFPHPGFNM_S_LLENHTRQ |
| 49 | 88 | SGWGSIEPENFSFPDDLQCV |
| 49 | 89 | SGWGSIEPENF_S_FPDDLQCV |
| 50 | 90 | RIQRGPGRAFVTIGKIGNMR |
| 50 | 91 | RIQRGPGRAFV_T_IGKIGNMR |
| 51 | 92 | EMSRHSLEQKPTDAPPKVLT |
| 51 | 93 | EMSRHSLEQKP_T_DAPPKVLT |
| 52 | 94 | CSESLELEDPSSGLGVTKQD |
| 52 | 95 | CSESLELEDPS_S_GLGVTKQD |
| 53 | 96 | LLEFYLAMPFA_T_PMEAELAR |

*Indicates attachment site of GalNAc residues to Ser/Thr (bold, underlined).

Glycopeptides were synthesized with and without N-terminal linker for printing on epoxy or NHS-activated glass slides, respectively. Peptides were designed based on known O-glycoproteins using the algorithm NetOGlyc for selection of O-glycosylation sites (Julenius et al. 2005), which in most cases coincides with experimentally determined O-glycosylation found on isolated proteins, as these glycoproteins have served as a training set for the algorithm. Glycopeptides were designed with a single GalNAc at position 12 to allow optimal exposure of peptide sequence flanking the O-glycan taking into consideration that the glycopeptides will be covalently linked primarily through the N-terminal amino acid. Glycopeptides were synthesized at 100 nmol scale using step-wise blocking by acetylation and printing directly with theoretical excess of 50 fold onto slides.

In one group, the paired peptide and single GalNAc glycopeptide library was further expanded by on-slide glycosylation with one or more recombinant glycosyltransferases to enhance the number of GalNAc O-glycosylation sites using one or more recombinant polypeptide GalNAc-transferases (e.g., GalNAc-T2, -T3 and -T4) (see, U.S. Pat. Nos. 5,876, 716 and 6,465,220) (Bennett et al. 1998; Bennett et al. 1996; White et al. 1995)(see also, FIG. 1). Further expansion was achieved by use of a recombinant sialyltransferase, ST6GalNAc-II, to produce STn glycoforms (structure no. 2, Table I) of the GalNAc glycopeptides. T glycoforms were produced by a recombinant *Drosophila* core1 β3galactosyltransferase, truncated core3 glycoforms (structure no. 6, Table I) were produced with a recombinant human β3GlcNAc-transferase (Iwai et al. 2002), and non-capped type1-core3 glycoforms (structure no. 9, Table I) were produced using β3Gal-T5 (see, U.S. Pat. No. 7,332,279).

Recombinant enzymes were expressed in insect cells using the baculo-virus system and used after semi-purification by Ni-chromatography (when HIS-tagged) or by ion exchange chromatographies. Glycosylation was monitored by staining of slides with lectins (HPA, VVA) (Sigma) and monoclonal antibodies to Tn (HBTn1, HBSTn1, HBT1) (Dako, Denmark). On-slide glycosylation was performed as follows: slides were quenched for 1 hr in 50 mM ethanolamine in 100 mM sodium borate pH 8, washed extensively in de-ionized water, and spun dry. Slides were blocked for 1 h with 1% BSA in PBS, pH 7.4, and in some cases with NP40 (1%) to reduce background. Slides were washed in PBS/0.05% Tween and enzyme reaction mixtures with BSA and detergent were applied and incubated 1-2 hrs at 37° C. Reaction mixtures for polypeptide GalNAc-transferases included MES buffer 125 mM, pH 7.4, 1% NP40, 1% BSA, 250 µM UDP-GalNAc, 2 mM $MnCl_2$ and 20 µg/mL enzyme. Reaction mixtures for galactosyltransferases included UDP-Gal, sialyltransferases CMP-NeuAc, GlcNAc-transferases UDP-GlcNAc. Following on-slide glycosylation slides were washed with PBS/Tween and processed with antibodies and lectins as described below.

It will be clear to one of ordinary skill in the art that on-slide glycosylation serves as a method to screen for additional glycoforms of peptides which may be recognized by autoantibodies present in patients. Once a particular glycoform of a given peptide is found to react with an autoantibody from a patient, the glycopeptide can be resynthesized in solution using the same enzymes used for on-slide glycosylation and the glycan structure and sites of attachment in the peptide confirmed by mass spectrometry (Tarp et al. 2007). The validated glycopeptide can then be incorporated into diagnostic panels as described throughout the specification and in Example 4.

FIG. 1 illustrates an example of on-slide glycosylation with the polypeptide GalNAc-transferase, GalNAc-T3, to glycosylate peptides and GalNAc glycopeptides having additional unsubstituted Ser/Thr residues to enhance the number of O-glycans. A library of 96 paired GalNAc-glycopeptides/peptides (20-mers with and without a single GalNAc residue at position 12), as designated in Table II, supra, were printed in triplicates (horizontal) on Scineon 16-well slides by JPT (Germany). In each pair in Table II, the glycopeptide of the pair contains a bold, underlined amino acid residue, indicating the site of attachment of GalNAc. Peptide pairs by peptide number are as follows: 1/2, 3/4, 5/6 . . . etc. The slide was reacted with the anti-Tn lectin HPA (1 µg/ml) without (FIG. 1A) and with (FIG. 1B) prior treatment with recombinant polypeptide GalNAc-T3 enzyme for on-slide GalNAc-glycosylation of available unglycosylated sites on peptides and glycopeptides.

The HPA lectin did not react with all GalNAc-glycopeptides (e.g., glycopeptide nos. 1-5 and 25-29), which is partly due to failure in synthesis and/or printing at these positions, as well as some restrictions of specificity of the GalNAc-binding lectin. The GalNAc-glycopeptides 1-5 did react with the HPA lectin in other experiments, and it was therefore concluded that there was a print failure. Conversion of peptides to GalNAc-glycopeptides by on-slide reaction with a polypeptide GalNAc-transferase is also expected to be dependent on the substrate specificity of the enzyme used, and, e.g., use of GalNAc-T2 rather than T3 may give a partly different labeling pattern.

Regardless, it is evident that most of the GalNAc-glycopeptides were labeled with HPA (FIG. 1A) and that most of the corresponding paired peptides were labeled only after GalNAc-T3 on-slide glycosylation (FIG. 1B). While HPA may not be expected to react with all GalNAc-glycopeptides, this lectin and other Tn reactive lectins such as HAA, VVA and DBA, as well as monoclonal anti-Tn antibodies (Dako) provide excellent controls for determining the quality of peptide synthesis and printing.

Example 2

High Through-Put Screening of Glycopeptide Microarrays with Human Serum for Identification of Glycopeptides Recognized by Cancer-Associated Auto-Antibodies Sera Origin and Handling:

A panel of human sera was obtained from CHTN (Cooperative Human Tissue Network) and Asterand Inc., under the guidelines of approved agreements by the providers. Sera obtained were from control individuals ("normal") (n=31) and from newly diagnosed cancer patients (n=147) with pancreatic, breast, colon, lung, prostate or ovary primary cancers. Briefly, for cancer sera, all blood samples were obtained on or near date of diagnosis, and serum was processed immediately, flash frozen and stored at −70° C. until shipment. Serum samples received from the providers as frozen aliquots generally of 1-2 mL were brought to room temperature, vortexed and distributed into 20-100 µL aliquots in closeable Eppendorf tubes (vWR) (pre-labeled), and immediately frozen and stored at −70° C. until use.

Glycopeptide Microarray Method:

Glycopeptides (20-mers with and without a single GalNAc residue at position 12) and control structures (corresponding unglycosylated peptides) were printed on Corning (Corning, N.Y.), Scienion (Germany) or Schott Nexterion® Slide H or Schott Nexterion® Slide H MPX 16 (Schott AG, Mainz, Germany) by JPT (Germany). Triplicates or quadruplicates of all compounds were printed at optimal concentrations (1-50 µM) or 50× excess relative to scale of synthesis for spot-synthesized glycopeptides printed without purification. After printing, slides were incubated for 1 hour (h) in a humidified hybridization chamber with 70-100% relative humidity and stored until use at 4° C. Unspotted slide areas were blocked for 1 h with 25 mM ethanolamine in 100 mM sodium borate pH 8.5. If an enzyme step was needed either to increase sites of GalNac attachments in peptides or extend O-glycans to T, STn, core 3 or other structures, addition of the enzyme reaction mixture in 25-35 µL was made in appropriate wells and the slide incubated at 37° C. for 1 h, after which it was washed in PBS/0.05% Tween and then PBS, and then spun dry.

Human sera (usually diluted 1:25), monoclonal antibodies, lectins and the like were added in 25 µL and the slide left at room temperature for 2 h in a moist, humid chamber after which it was washed as above and spun dry (if no superstructure). Secondary antibodies were added at appropriate concentrations (for human sera, usually 1:1500 for anti-human IgG with a Cy3 chromophore). In some cases, for some controls, lectin-Cy3 was used directly as final step. The final step was washing as above, with a brief de-ionized water wash and the slide spun dry for scanning Analysis was made on a GenePix 4200AL Scanner at PMT 400 and power mode 10-50. Data were analyzed and plotted using Microsoft Excel.

Figure 2:
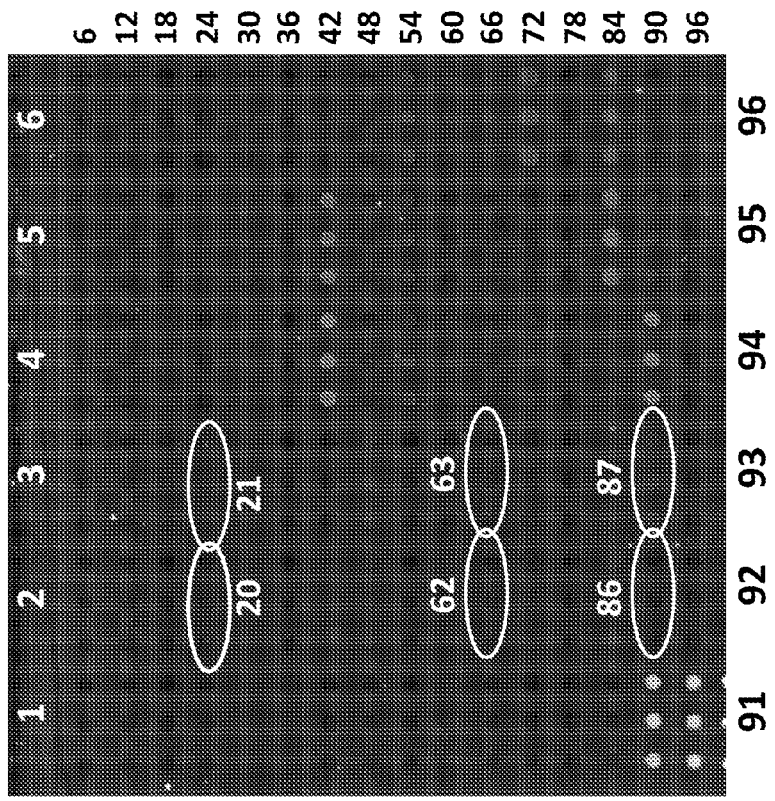
FIG. 2 is an image of a microarray slide and illustrates reactivities of serum (1:25 dilution) from a newly diagnosed prostate cancer patient (#762 in FIG. 2A) and a normal control serum from an individual that does not have prostate cancer (#174 in FIG. 2B) on the library of 96 paired peptides/GalNAc-glycopeptides as designated in Table II.
Figure 2:
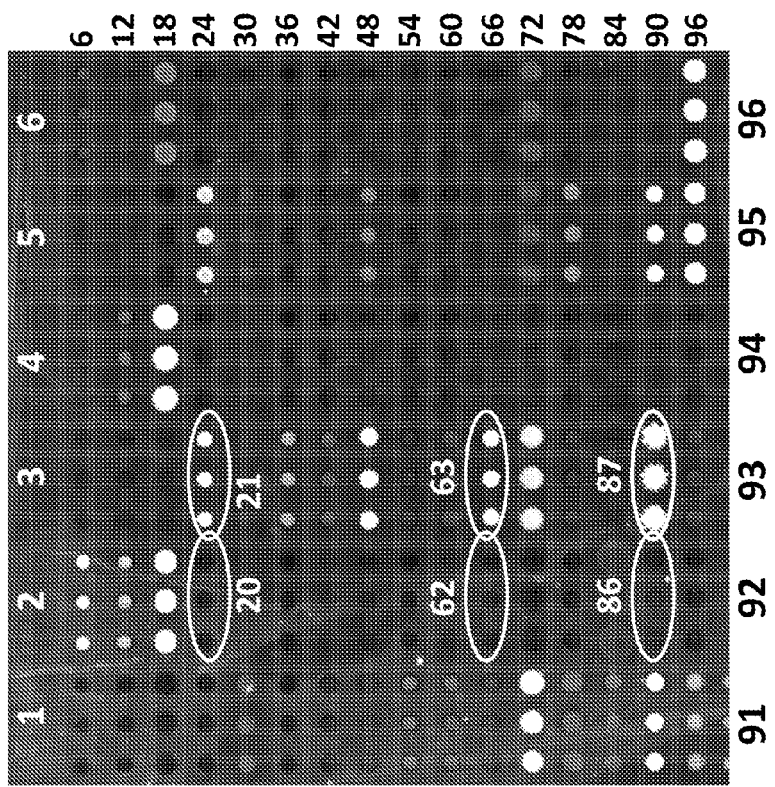

Identification of Cancer-Associated Auto-Antibodies to GalNAc-Glycopeptide Epitopes:

Glycopeptides (20-mers with and without a single GalNAc residue at position 12) were printed in triplicates (horizontal) on Scineon 16-well slides by JPT (Germany) and bound human IgG antibodies detected by a labeled secondary anti-human IgG antibody. FIG. 2 illustrates examples of reactivities of serum (1:25 dilution) from a newly diagnosed prostate cancer patient (#762 in Panel A) and a normal control serum from a healthy individual (#174 in Panel B) on the library of 96 paired peptides/GalNAc-glycopeptides as designated in Table II. Candidate cancer-associated IgG antibodies identified in the cancer serum directed to GalNAc glycopeptide epitopes are indicated by open circles labeled 20/21, 62/63, and 86/87 for the paired peptide and GalNAc glycopeptides, respectively. The analysis demonstrates that serum of cancer patient contain IgG antibodies specifically reacting with epitopes found on GalNAc glycopeptides 21, 63, and 87, and since these antibodies do not react with the corresponding unglycosylated peptides 20, 62, and 86, it may be concluded that the epitopes are comprised of a GalNAc-peptide epitope including both the O-glycan part as well as part of the peptide sequence.

Human IgG antibodies from several cancers were shown to bind selectively to several GalNAc-glycopeptides and not the corresponding peptide, and such antibodies were not detected in healthy individuals. An example of this is shown in FIG. 2, where a prostate cancer serum (prca#762) labels three GalNAc-glycopeptides (#21, 63, and 87), and not the corresponding peptide (#20, 62, and 86). These three candidates were also identified in other cancer sera but not in the controls as shown in FIGS. 3-5, and described, infra.

Figure 3:
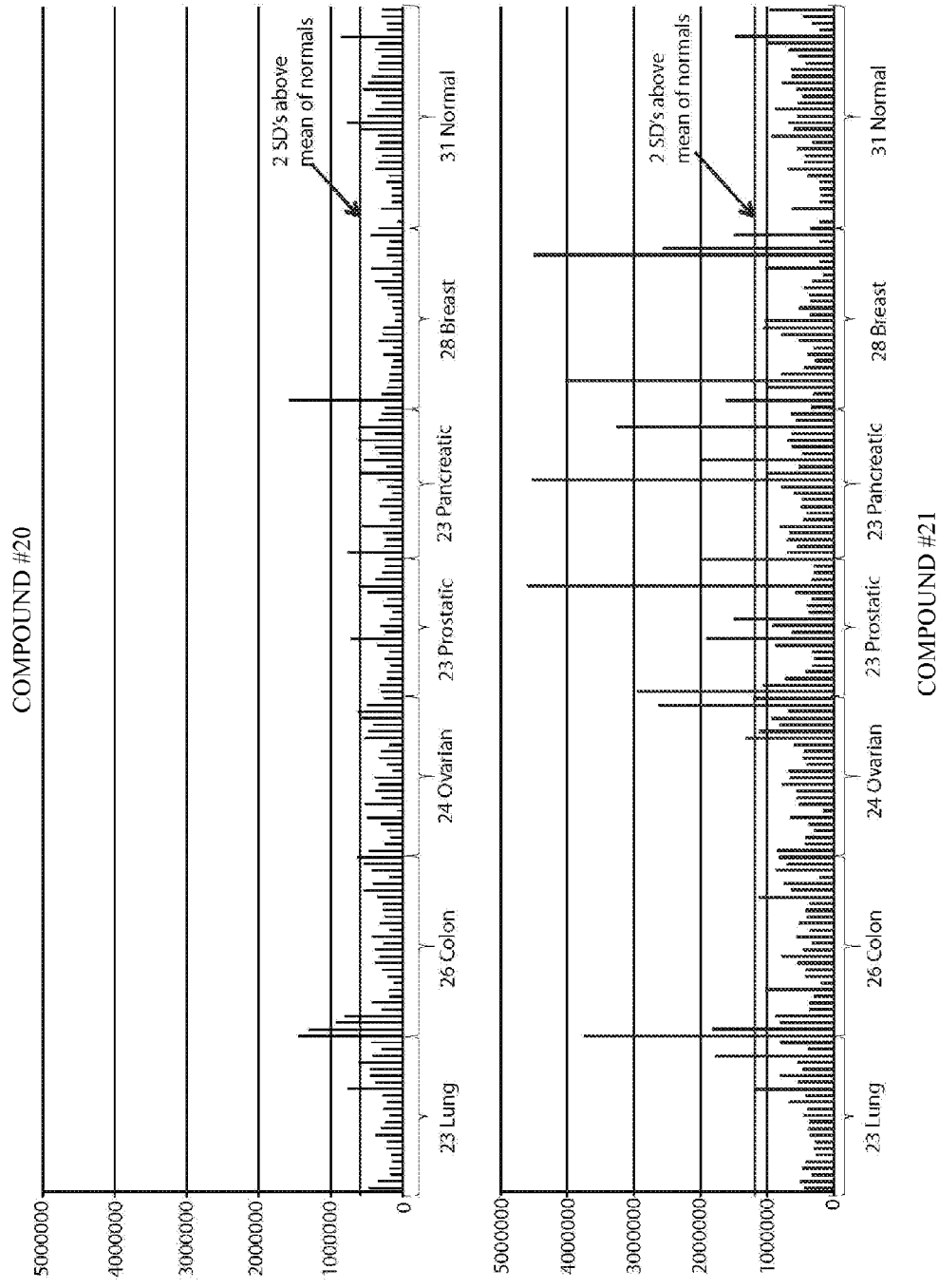
FIGS. 3-5 are bar graphs and illustrate microarray screening results from 147 cancer and 31 control sera on the glycopeptide pairs identified herein as #20/21 (FIG. 3), #62/63 (FIG. 4), or #86/87 (FIG. 5).

FIG. 3 illustrates results of screening 147 cancer sera and 31 control sera (normal sera) on the glycopeptide pair #20/21. Sera obtained from newly diagnosed cancer patients with lung, colon, ovary, prostate, pancreas or breast tumors as well as controls (as indicated) were reacted with the 96-peptide array on Scineon 16-well slides (1:25 dilution) followed by cy3 labeled anti-human IgG (diluted to 1:1500). Arrays were analyzed on GenePix 4200 scanner at 400 pmt with 50 power and relative intensities graphed.

Figure 4:
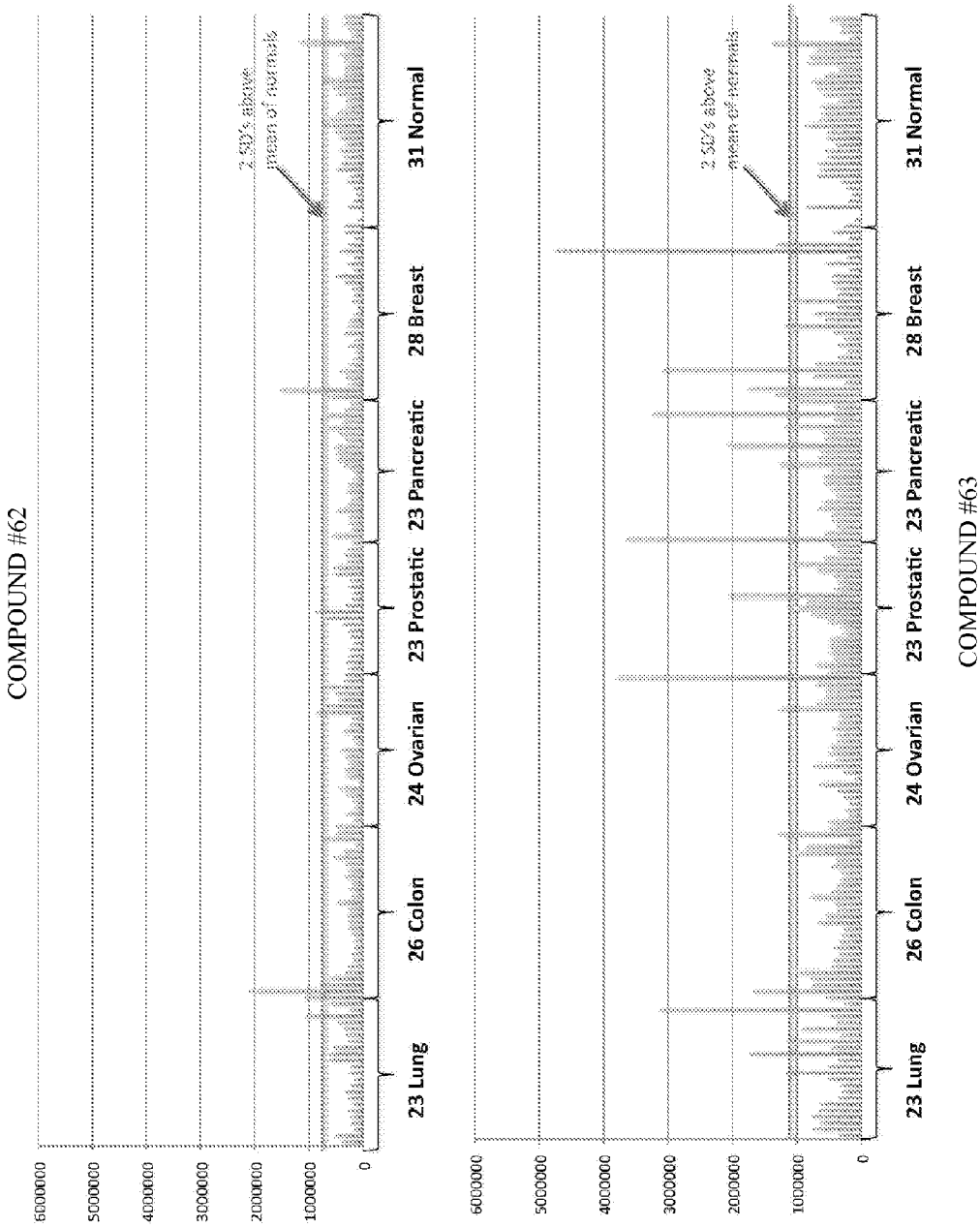
Figure 5:
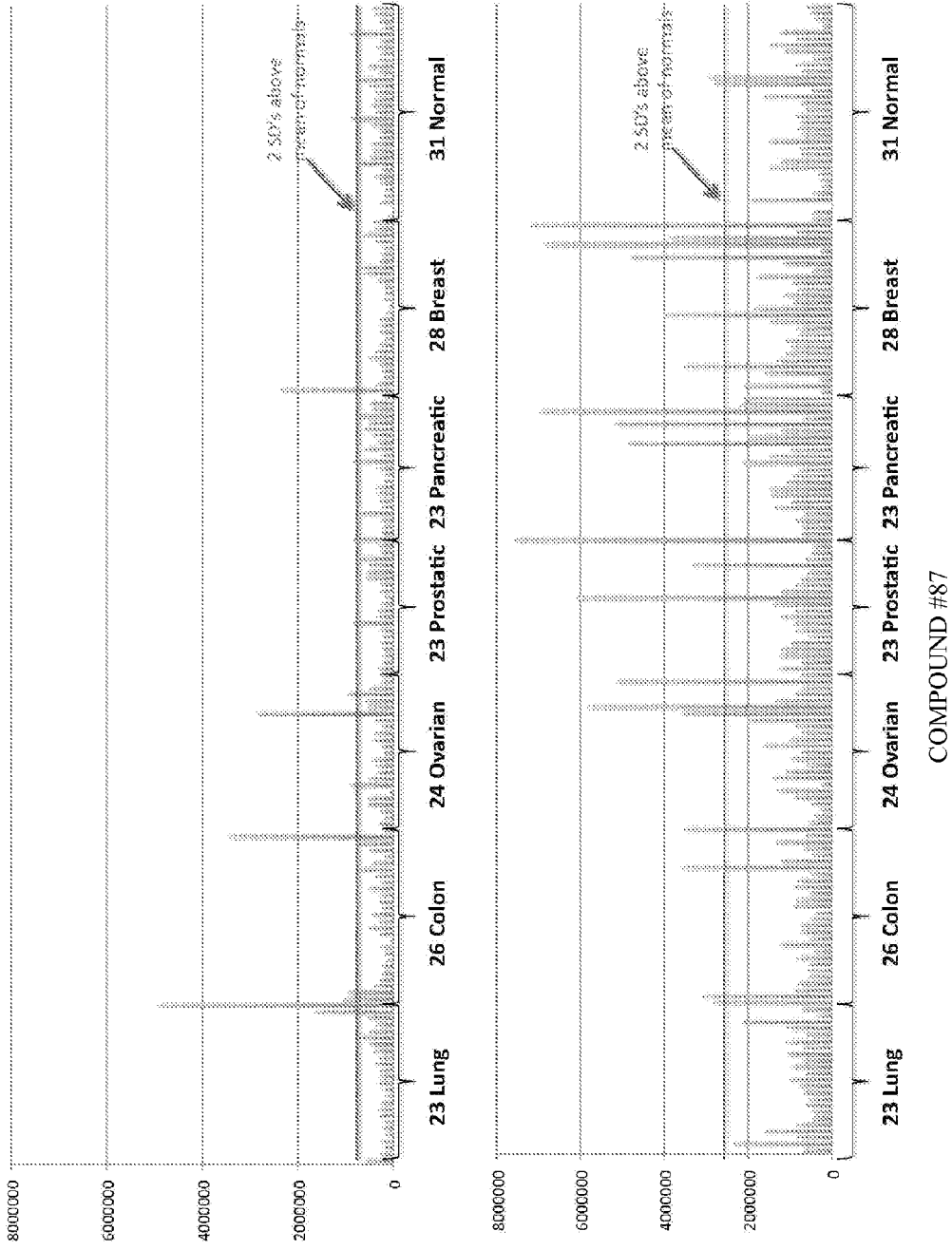

FIG. 4 illustrates results of screening 147 cancer sera and 31 normal sera on the glycopeptide pair #62/63. FIG. 5 illustrates results of screening 147 cancer sera and 31 normal sera on the glycopeptide pair #86/87.

Peptides 20/21, each having the sequence identified as SEQ ID NO: 15, are derived from SPP1 (Ensg00000118785) GenBank Accession No. NP_001035147 (SEQ ID NO: 61), peptides 62/63, each having the sequence identified as SEQ ID NO: 36 are derived from LAMP2 (Ensg00000005893) (ENST00000200639) protein (ENSP00000200639) GenBank Accession No. NP_002285 (SEQ ID NO: 64), and peptides 86/87, each having the sequence identified as SEQ ID NO: 49, are derived from KLK1 (gene: Ensg00000167748) (transcript: ENST00000301420) (protein: ENSP00000301420) (GenBank Accession No. NP_002248) (SEQ ID NO: 66). These proteins have broad expression patterns in tissues and hence may induce antibodies in many cancers.

The presented method using a limited glycopeptide library identified three candidate targets for human disease-associated auto-antibodies. These auto-antibody targets were defined by the discriminating factor that cancer-associated IgG antibodies reacted selectively with a glycopeptide and not the corresponding peptide or other glycopeptides with the same O-glycan or the O-glycan presented as a hapten on an artificial carrier.

Example 3

Generation of Antibodies to Identified Auto-Antibody Targets for Diagnostic Use

Monoclonal or polyclonal antibodies may be generated to the identified glycopeptide antigens by known methods (Takeuchi et al. 2002; Hanisch et al. 1995; Reis et al. 1998; Sorensen et al. 2006). Briefly, the following procedure serves as an example for generation of antibodies with the desired glycopeptides specificity but other procedures leading to the same result will be known to the skilled in the art.

Immunization Protocol:

Glycopeptides are coupled to keyhole limpet hemocyanin (KLH) (Pierce, Rockford, Ill.) using glutaraldehyde. Efficiency of conjugation is assessed by analyzing the reaction by size exclusion chromatography on a PD-10 column, where the conjugate/glycopeptides ratio can be determined by ELISA using appropriate reagents such as antibodies and lectins detecting the glycopeptides. Essentially all reactivity with a Tn reactive lectin (HPA) is found with the excluded fraction and insignificant reactivity in the included fractions expected to contain peptides. Titration analysis of the KLH conjugate with the corresponding glycopeptide in ELISA indicated conjugation ratio KLH to glycopeptide of approximately 1:200. Female Balb/c (Jackson Labs) wild type mice are injected subcutaneously with 10 or 15 µg of glycopeptide-KLH in a total volume of 200 µl (1:1 mix with Freunds adjuvant, Sigma). Mice received four immunizations 2-4 wks apart, and blood samples are obtained by tail or eye bleeding 1 wk following the third and fourth immunization.

Hybridoma Production:

Mouse hybridomas are produced by fusion of splenocytes to NS-1 followed by selection in HAT/HT (Hypoxanthine, Aminopterin, Thymidine). Hybridomas are selected by initial screening by ELISA with GalNAc-glycopeptides and corresponding peptides as well as irrelevant control compounds. Further characterization is done on glycopeptides microarrays as well as on a panel of human cancer cell lines expressing the corresponding aberrant glycoprotein.

Enzyme-linked immunosorbent assays (ELISA) are performed using 96-well MaxiSorp™ plates (Nunc). Plates are coated overnight at 4° C. with 1 µg/ml of glycopeptides in bicarbonate-carbonate buffer (pH 9.5), blocked with 5% BSA in PBS, followed by incubation with sera (diluted in PBS) or monoclonal antibodies for 2 hours (hrs) at room temperature. Bound antibodies are detected with peroxidase-conjugated rabbit anti-mouse immunoglobulins (Dako, Denmark) or isotype specific antibodies peroxidase-conjugated goat anti-mouse IgM, IgG1, IgG2a, IgG2b, or IgG3 (Southern Biotechnology Associates, USA). Plates are developed with o-phenylenediamine tablets (Dako, Denmark) and read at 492 nm. Control antibodies included anti-carbohydrate antibodies HBTn–1 (Tn) and HBSTn–1 (STn) (Dako) and lectins HPA, VVA and HAA (Sigma). Control sera included mice immunized with irrelevant peptides linked to KLH. Human cancer cell lines from different cancers are all obtained from ATCC and cultured as recommended by ATCC.

Immunocytochemical staining of cells are performed as follows: cells are harvested by trypsination, washed and plated onto multi-well glass slides and fixed for 10 minutes (min) in ice cold acetone or in methanol acetone. Fixed cells are incubated overnight at 4° C. with mouse sera (1:200/1:400/1:800) or hybridoma antibodies, followed by incubation for 45 min at room temperature with FITC-conjugated rabbit anti-mouse immunoglobulins (Dako, Denmark). Slides are mounted in glycerol containing p-phenylenediamine and examined in a fluorescence microscope.

For further determination of expression of glycopeptides epitope in human cancers immunohistochemistry of fixed and frozen tissue samples are performed. Frozen sections are fixed for 10 min in cold methanol/acetone (50:50). Formalin fixed, paraffin wax embedded tissues of different carcinoma and healthy tissues are obtained from Origine (US) and stained by immunofluorescence or peroxidase techniques. Paraffin sections are dewaxed, rehydrated, and treated with 0.5% $H_2O_2$ in methanol for 30 min. Section are rinsed in TBS and incubated for 20 min with rabbit nonimmune serum. Sections are rinsed and incubated overnight at 4° C. with primary antibody. Sections are rinsed and incubated with biotin-labeled rabbit anti-mouse serum (Dako, Denmark) diluted 1:200 in TBS for 30 min, rinsed with TBS, and incubated for 1 h with avidin-biotin-peroxidase complex (Dako, Denmark). Sections are rinsed with TBS and developed with 0.05% 3,3'-diaminobenzidine tetrahydrochloride freshly prepared in 0.05 M TBS containing 0.1% $H_2O_2$. Sections are stained with hematoxylin, dehydrated and mounted.

Example 4

Broad Discovery of O-Glycopeptide Epitopes

Figure 6A:
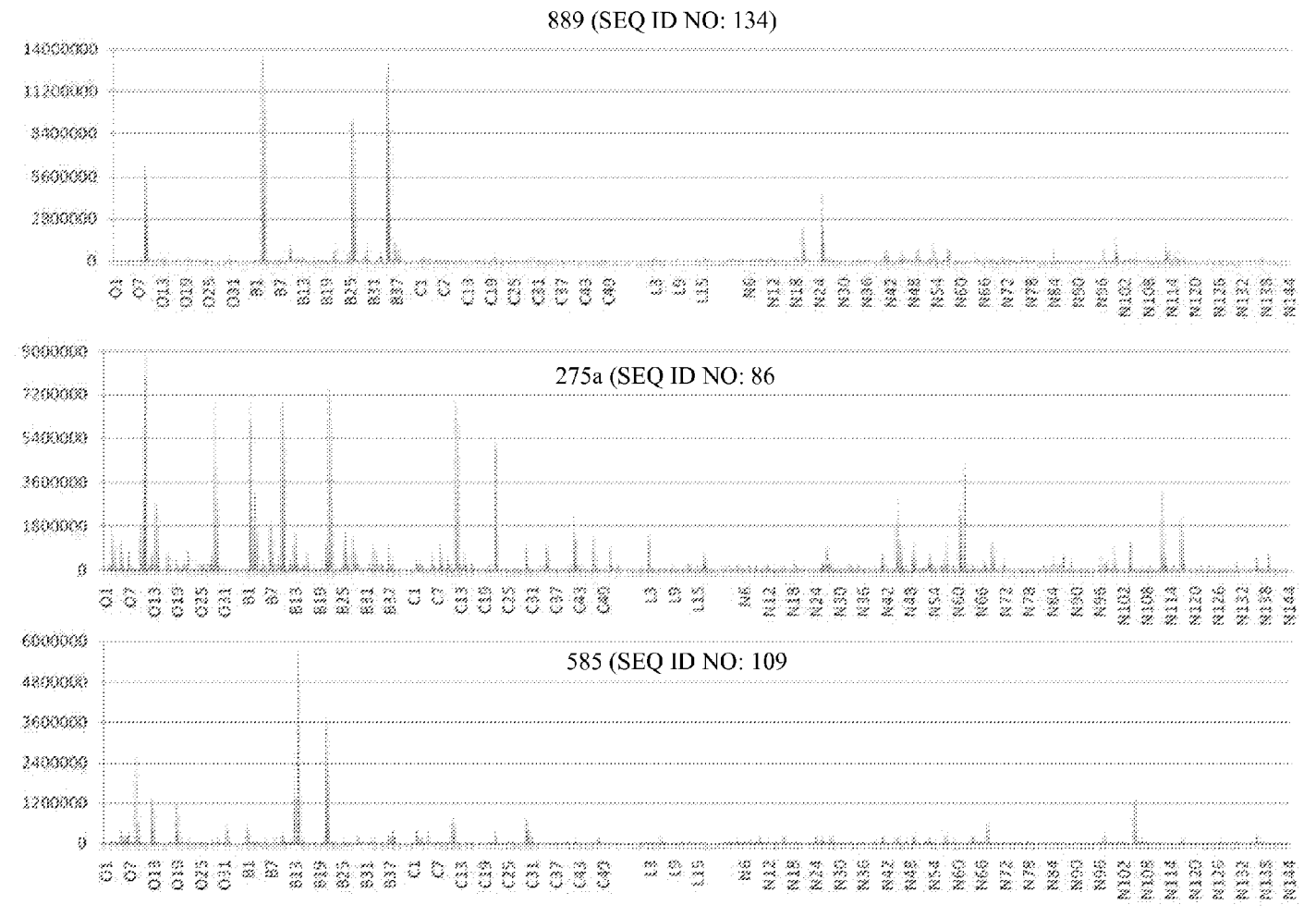
Figure 6B:
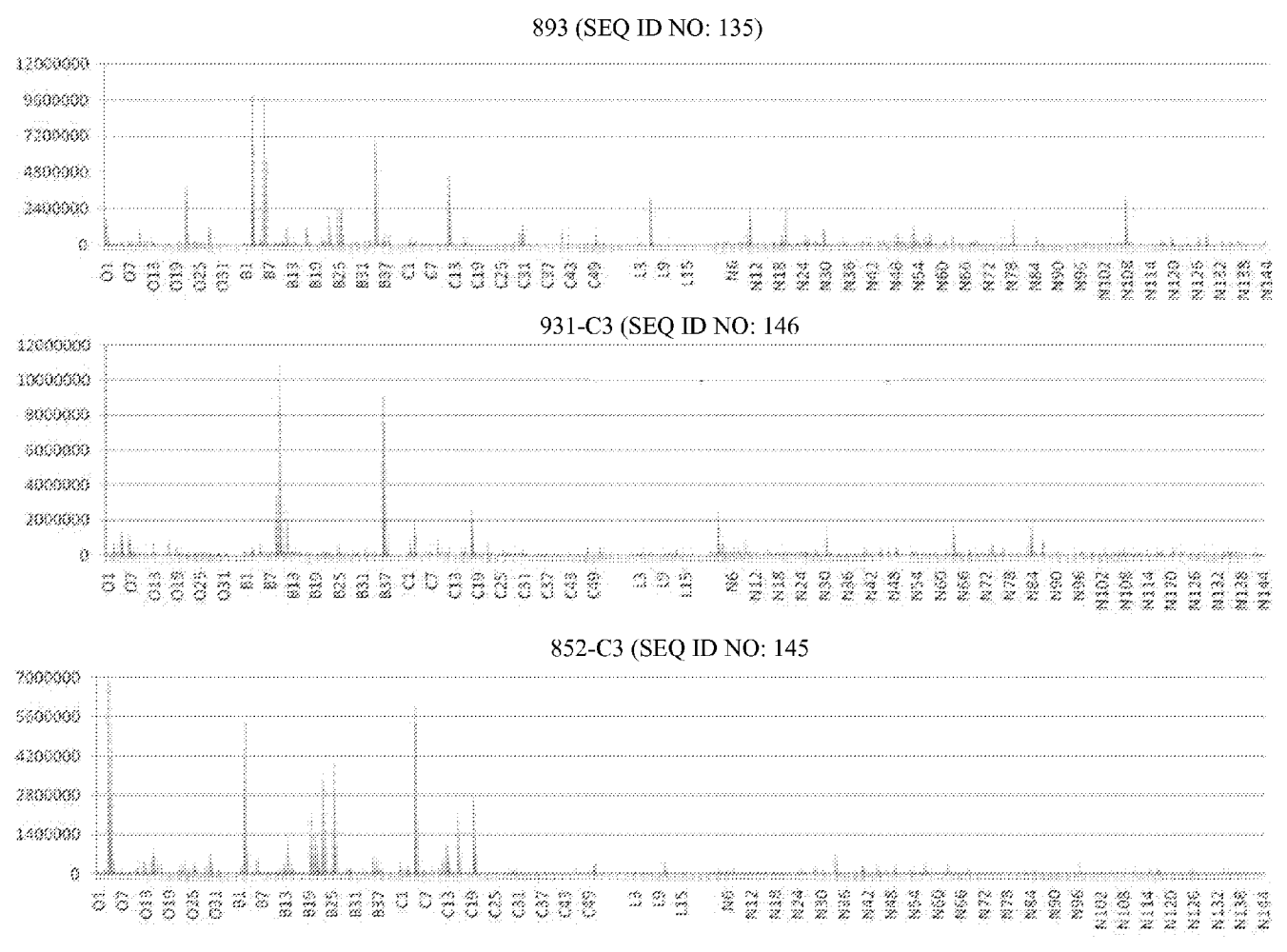
Figure 6C:
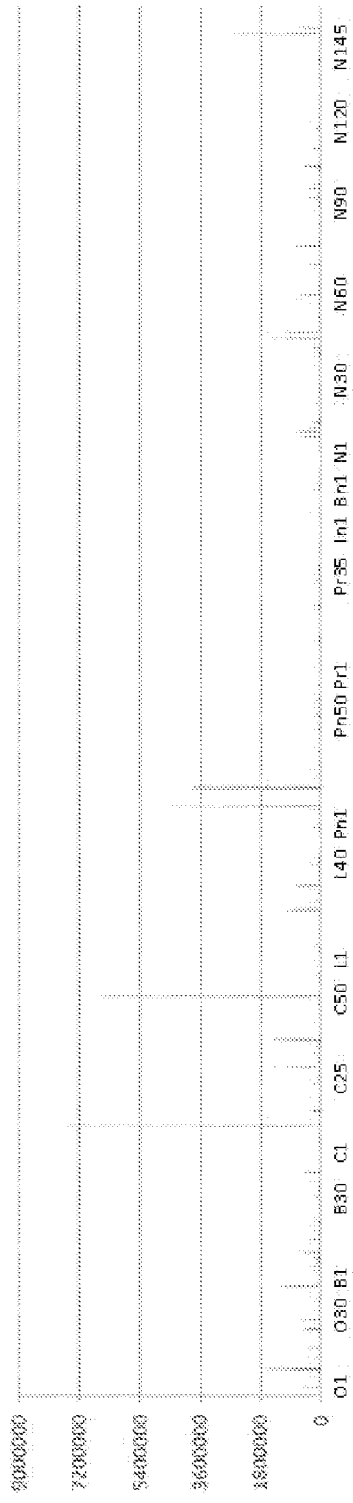
FIG. 6C: gycopeptides 873 (SEQ ID NO: 132) and 690 (SEQ ID NO: 116). The following human sera were used for FIGS. 6A and 6B: 32 ovarian cancer (O), 38 breast cancer (B), 54 colon cancer (C), 17 lung cancer (L), as well as 145 normal sera (N) (Asterand Corp). The following sera were used for FIG. 6C: 32 ovarian cancer (O), 38 breast cancer (O), 54 colon cancer (C), 42 lung cancer (L), 52 pancreactic cancer (Pn), 35 prostatic cancer (Pr), 8 inflammatory disease (In), 8 benign controls (Bn), and 145 healthy controls (N). Sera were screened at 1:20 dilution. Anti-human-IgG conjugated to Cy3 was used as the secondary detection unit and slides were scanned with a GenePix 4200AL Microarray Scanner.
Figure 6C:
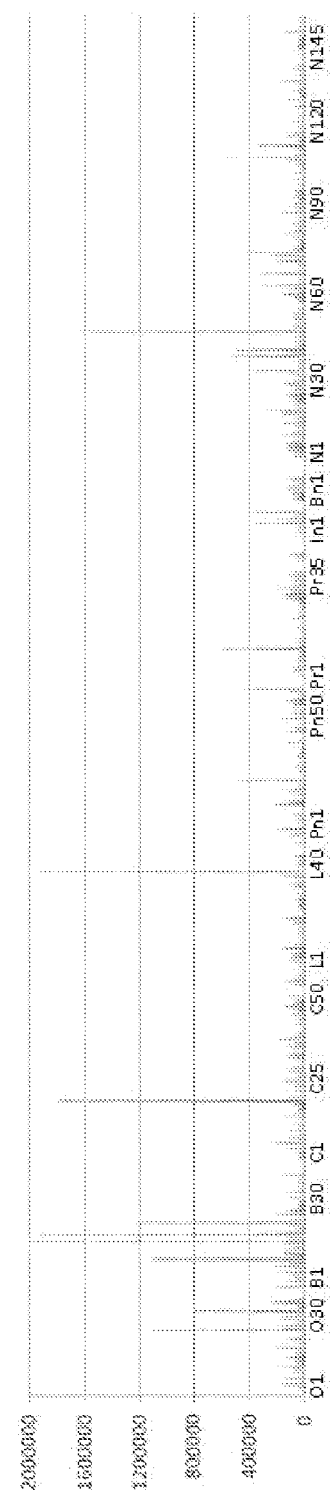

A larger library of GalNAc O-glycopeptides designed with GalNAc linked to serine or threonine at position 12 in 20-mer peptides was produced as described in Example 1. Peptides were selected among cell membrane and secreted human proteins that contain serine and threonine residues that are predicted to be O-glycosylated by the NetOGlyc algorithm (Julenius et al. 2005). A total of 960 GalNAc glycopeptides were synthesized at 0.5 mg scale (Sigma) and printed on microarray hydrogel slides (Schott Nexterion) as described in Example 1. Slides were reacted with human cancer sera (ovarian, breast, colon, lung, pancreas, prostate, 235 total sera) and control sera (145 healthy, 20 inflammatory, 20 benign tumor). Glycopeptides preferentially reactive with human IgG antibodies from cancer patients compared to controls were selected for resynthesis at 5 mg scale with amidated C-terminus (New England Peptide (Gardner, Mass.) (Table III). Resynthesized glycopeptides were reprinted on microarray slides at 50 µM and reacted with human cancer sera (Total 286 sera: 32 ovarian cancer (O), 38 breast cancer (B), 54 colon cancer (C), 17 lung cancer (L), and 145 age and sex matched control normal sera as described in Example 1. Table III lists glycopeptides exclusively or preferentially reactive with human IgG from cancer patients compared to controls and examples of reactivities are shown in FIG. 6.

TABLE III

Glycopeptides reactive with IgG antibodies from human cancer sera

| Peptide number | Sequence ID | Protein | Sequence |
| --- | --- | --- | --- |
| 166 | 82 | Oncostatin | H2N-TKAGRGASQPPTPTPASDAF-amide |
| 113 | 83 | gp95 | H2N-EEEPEETAEDTTEDTEQDED-amide |
| 218 | 84 | MUC13 | H2N-TASTTANTPFPTATSPAPPI-amide |
| 225 | 85 | MUC13 | H2N-PAPPIISTHSSSTIPTPAPP-amide |
| 275a | 86 | Ceruplasm | H2N-LAKMYYSAVEPTKDIFTGLI-amide |
| 284 | 87 | CD46 | H2N-PSSTKPPALSHSVSTSSTTK-amide |
| 308 | 88 | EBAG9 | H2N-LEPDYFKDMTPTIRKTQKIV-amide |
| 318a | 89 | MUC17 | H2N-STMPVVSSEASTHSTTPVDT-amide |
| 324 | 90 | MUC17 | H2N-STHSTTPVDTSTPVTTSTEA-amide |
| 370 | 91 | IL6-R | H2N-IPPEDTASTRSSFTVQDLKP-amide |
| 382 | 92 | R-PTP-alpha | H2N-EAKTSNPTSSLTSLSVAPTF-amide |
| 389 | 93 | R-PTP-alpha | H2N-ARTEPWEGNSSTAATTPETF-amide |
| 443 | 94 | ODAM | H2N-VDPLQLQTPPQTQPGPSHVM-amide |
| 450 | 95 | ODAM | H2N-SPKPSTTNVFTSAVDQTITP-amide |
| 456 | 96 | IGFB-3 | H2N-PAPPAPGNASESEEDRSAGS-amide |
| 458 | 97 | IGFB-3 | H2N-ASESEEDRSAGSVESPSVSS-amide |
| 465 | 98 | MUC15 | H2N-ANLNSDKENITTSNLKASHS-amide |
| 484 | 99 | MUC15 | H2N-LTTNSDSFTGFTPYQEKTTL-amide |
| 485 | 100 | MUC15 | H2N-SFTGFTPYQEKTTLQPTLKF-amide |
| 485a | 101 | MUC15 | H2N-SFTGFTPYQEKTTLQPTLKF-amide |
| 505 | 102 | TPBG Trophob | H2N-SPTSSASSFSSSAPFLASAV-amide |
| 522 | 103 | IgA1 hinge | H2N-TVPCPVPSTPPTPSPSTPPT-amide |
| 524 | 104 | IgA1 hinge | H2N-VPSTPPTPSPSTPPTPSPSC-amide |
| 544 | 105 | R-PTP-N | H2N-SEPPKAARPPVTPVLLEKKS-amide |
| 546 | 106 | R-PTP-N | H2N-GQSQPTVAGQPSARPAAEEY-amide |

TABLE III-continued

Glycopeptides reactive with IgG antibodies from human cancer sera

| Peptide number | Sequence ID | Protein | Sequence |
|---|---|---|---|
| 558 | 107 | CMRF35 | H2N-TPASITAAKTSTITTAFPPV-amide |
| 569 | 108 | TNF-RSF1B | H2N-GNASMDAVCTSTSPTRSMAP-amide |
| 585 | 109 | CGB2 | H2N-TDCGGPKDHPLTCDDPRFQA-amide |
| 587 | 110 | CGB2 | H2N-AQAS SSSKAPPPSLPSPSRLP-amide |
| 592 | 111 | Acrosomal SP Cadherin 1 | H2N-PLSELESGEQPSDEQPSGEH-amide |
| 601 | 112 | (CD) | H2N-PQRSSTAILQVSVTDTNDNH-amide |
| 605 | 113 | CD Ovomorolin | H2N-GALPGTSVMEVTATDADDDV-amide |
| 612 | 114 | CD Mucin like | H2N-EQEPPSTDVPPSPEAGGTTG-amide |
| 676 | 115 | Inhibin alpha | H2N-RPEATPFLVAHTRTRPPSGG-amide |
| 690 | 116 | IGF-BP-6 | H2N-PGTSTTPSQPNSAGVQDTEM-amide |
| 739 | 117 | LTBP1 | H2N-EVAPEASTSSASQVIAPTQV-amide |
| 752 | 118 | CD 248 Endosialin | H2N-QPPDFALAYRPSFPEDREPQ-amide |
| 755 | 119 | CD 248 Endosialin | H2N-LSVTRPVVVSATHPTLPSAH-amide |
| 757 | 120 | CD 248 Endosialin | H2N-PSAHQPPVIPATHPALSRDH-amide |
| 765 | 121 | CD 248 Endosialin | H2N-APDALVLRTQATQLPIIPTA-amide |
| 823 | 122 | ICAM-1 | H2N-GALFPGPGNAQTSVSPSKVI-amide |
| 827 | 123 | ICAM-1 | H2N-HLALGDQRLNPTVTYGNDSF-amide |
| 827a | 124 | ICAM-1 | H2N-HLALGDQRLNPTVTYGNDSF-amide |
| 848 | 125 | MUC1 | H2N-PATEPASGSAATWGQDVTSV-amide |
| 852 | 126 | MUC1 | H2N-VPVTRPALGSTTPPAHDVTS-amide |
| 859 | 127 | MUC1 | H2N-NVTSASGSASGSASTLVHNG-amide |
| 859a | 128 | MUC1 | H2N-NVTSASGSASGSASTLVHNG-amide |
| 863 | 129 | MUC1 | H2N-GTSARATTTPASKSTPFSIP-amide |
| 863a | 130 | MUC1 | H2N-GTSARATTTPASKSTPFSIP-amide |
| 870 | 131 | MUC1 | H2N-SDTPTTLASHSTKTDASSTH-amide |
| 873 | 132 | MUC1 | H2N-TKTDASSTHHSTVPPLTSSN-amide |
| 883 | 133 | MUC1 | H2N-TDYYQELQRDISEMFLQIYK-amide |
| 889 | 134 | MUC1 | H2N-HDVETQFNQYKTEAASRYNL-amide |
| 893 | 135 | MUC1 | H2N-ASRYNLTISDVSVSDVPFPF-amide |
| 894 | 136 | MUC1 | H2N-RYNLTISDVSVSDVPFPFSA-amide |
| 895 | 137 | MUC1 | H2N-DVSVSDVPFPFSAQSGAGVP-amide |
| 914 | 138 | MUC4 | H2N-TAGRPTGQSSPTSPSASPQE-amide |
| 931 | 139 | MUC4 | H2N-SLASQATDIFSTVPPTPPSI-amide |
| 934 | 140 | MUC4 | H2N-FSTVPPTPPSITSTGLTSPQ-amide |
| 936 | 141 | MUC4 | H2N-PTPPSITSTGLTSPQTETHT-amide |
| 941 | 142 | MUC4 | H2N-LTSPQTETHTLSPSGSGKTF-amide |
| 977 | 143 | MUC4 | H2N-TDTSSASTGHATPLPVTSLS-amide |
| 983 | 144 | MUC4 | H2N-HATPLAVSSATSASTVSSDS-amide |
| 852-C3 | 145 | MUC1 | H2N-VPVTRPALGSTT[GlcNAc]PPAHDVTS-amide |
| 931-C3 | 146 | MUC4 | H2N-SLASQATDIFST[GlcNAc]VPPTPPSI-amide |

*Bold S or T indicates attachment site of GalNAc residues to Ser/Thr; Bold [GlcNAc]indicates an addition of glucosamine attached to GalNAc (in bold). Bold, underlined name indicates peptide assayed in graphs in FIG. 6.

Since IgG antibodies reactive with glycopeptides epitopes recognize both the peptide sequence in close proximity to the O-glycan (i.e., one to five or even eighth residues N- and C-terminal of the O-glycan) as well as the O-glycan structure, it is clear that different glycoforms of one glycopeptide may be recognized by different IgG antibodies and these antibodies may be found in different cancer patients. In this Example, GalNAc-glycopeptides from MUC1 and MUC4 were also produced as the core 3 GlcNAcβ1-3GalNAcα1-O-Ser/Thr glycoform with a recombinant core 3 synthase as described in Example 1. Two core 3 glycopeptides (#852-C3 and #931-C3) were identified as exclusively recognized by IgG antibodies in sera from cancer patients.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

LITERATURE CITED

Anderson K S, Labaer J (2005) The sentinel within: exploiting the immune system for cancer biomarkers. J Proteome Res 4:1123-1133.

Anderson K S, Ramachandran N, Wong J, Raphael J V, Hainsworth E, Demirkan G, Cramer D, Aronzon D, Hodi F S, Harris L, Logvinenko T, Labaer J (2008) Application of protein microarrays for multiplexed detection of antibodies to tumor antigens in breast cancer. J Proteome Res 7:1490-1499.

Anderton S M (2004) Post-translational modifications of self antigens: implications for autoimmunity. Curr Opin Immunol 16:753-758.

Backlund J, Treschow A, Bockermann R, Holm B, Holm L, Issazadeh-Navikas S, Kihlberg J, Holmdahl R (2002) Glycosylation of type II collagen is of major importance for T cell tolerance and pathology in collagen-induced arthritis. Eur J Immunol 32:3776-3784.

Bennett E P, Hassan H, Clausen H (1996) cDNA cloning and expression of a novel human UDP-N-acetyl-alpha-D-galactosamine-Polypeptide N-acetylgalactosaminyltransferase, GalNAc-T3. Journal of Biological Chemistry 271: 17006-17012.

Bennett E P, Hassan H, Mandel U, Mirgorodskaya E, Roepstorff P, Burchell J, Taylor-Papadimitriou J, Hollingsworth M A, Merkx G, van Kessel A G, Eiberg H, Steffensen R, Clausen H (1998) Cloning of a human UDP-N-acetyl-alpha-D-Galactosamine:polypeptide N-acetylgalactosaminyltransferase that complements other GalNAc-transferases in complete O-glycosylation of the MUC1 tandem repeat. J Biol Chem 273:30472-30481.

Brandlein S, Eck M, Strobel P, Wozniak E, Muller-Hermelink H K, Hensel F, Vollmers H P (2004a) PAM-1, a natural human IgM antibody as new tool for detection of breast and prostate precursors. Hum Antibodies 13:97-104.

Brandlein S, Pohle T, Vollmers C, Wozniak E, Ruoff N, Muller-Hermelink H K, Vollmers H P (2004b) CFR-1 receptor as target for tumor-specific apoptosis induced by the natural human monoclonal antibody PAM-1. Oncol Rep 11:777-784.

Chapman C, Murray A, Chakrabarti J, Thorpe A, Woolston C, Sahin U, Barnes A, Robertson J (2007) Autoantibodies in breast cancer: their use as an aid to early diagnosis. Ann Oncol 18:868-873.

Clark R A, Fuhlbrigge R C, Springer T A (1998) L-Selectin ligands that are O-glycoprotease resistant and distinct from MECA-79 antigen are sufficient for tethering and rolling of lymphocytes on human high endothelial venules. J Cell Biol 140:721-731.

Danielczyk A, Stahn R, Faulstich D, Loffler A, Marten A, Karsten U, Goletz S (2006) PankoMab: a potent new generation anti-tumour MUC1 antibody. Cancer Immunol Immunother 55:1337-1347.

Dian D, Janni W, Kuhn C, Mayr D, Karsten U, Mylonas I, Friese K, Jeschke U (2009) Evaluation of a novel anti-mucin 1 (MUC1) antibody (PankoMab) as a potential diagnostic tool in human ductal breast cancer; comparison with two established antibodies. Onkologie 32:238-244.

Doyle H A, Mamula M J (2001) Post-translational protein modifications in antigen recognition and autoimmunity. Trends Immunol 22:443-449.

Doyle H A, Mamula M J (2005) Posttranslational modifications of self-antigens Ann N Y Acad Sci 1050:1-9.

Gahring L, Carlson N G, Meyer E L, Rogers S W (2001) Granzyme B proteolysis of a neuronal glutamate receptor generates an autoantigen and is modulated by glycosylation. J Immunol 166:1433-1438.

Hanisch F G, Stadie T, Bosslet K (1995) Monoclonal-Antibody Bw835 Defines A Site-Specific Thomsen-Friedenreich Disaccharide Linked to Threonine Within the Vtsa Motif of Muc1 Tandem Repeats. Cancer Research 55:4036-4040

Hassan H, Bennett E P, Mandel U, Hollingsworth M A, Clausen H (2000) Carbohydrates in Chemistry and Biology—a Comprehension Handbook. Wiley-VCH, pp. 273-292.

Hellstrom I, Friedman E, Verch T, Yang Y, Korach J, Jaffar J, Swisher E, Zhang B, Ben Baruch G, Tan M C, Goedegebuure P, Hellstrom K E (2008) Anti-mesothelin antibodies and circulating mesothelin relate to the clinical state in ovarian cancer patients. Cancer Epidemiol Biomarkers Prev 17:1520-1526.

Iwai T, Inaba N, Naundorf A, Zhang Y, Gotoh M, Iwasaki H, Kudo T, Togayachi A, Ishizuka Y, Nakanishi H, Narimatsu H (2002) Molecular cloning and characterization of a novel UDP-GlcNAc:GalNAc-peptide beta1,3-N-acetylglucosaminyltransferase (beta 3Gn-T6), an enzyme synthesizing the core 3 structure of O-glycans. J Biol Chem 277:12802-12809.

Julenius K, Molgaard A, Gupta R, Brunak S (2005) Prediction, conservation analysis, and structural characterization of mammalian mucin-type O-glycosylation sites. Glycobiology 15:153-164.

Kawabata R, Wada H, Isobe M, Saika T, Sato S, Uenaka A, Miyata H, Yasuda T, Doki Y, Noguchi Y, Kumon H, Tsuji K, Iwatsuki K, Shiku H, Ritter G, Murphy R, Hoffman E, Old L J, Monden M, Nakayama E (2007) Antibody response against NY-ESO-1 in CHP-NY-ESO-1 vaccinated patients. Int J Cancer 120:2178-2184.

Li J, Sullivan C A, Harris L (2009) Where do we place PankoMab in the reagents used to study the MUC1 superfamily? Onkologie 32:235-237

Liu W L, Zhang G, Wang J Y, Cao J Y, Guo X Z, Xu L H, Li M Z, Song L B, Huang W L, Zeng M S (2008) Proteomics-based identification of autoantibody against CDC25B as a novel serum marker in esophageal squamous cell carcinoma. Biochem Biophys Res Commun 375:440-445.

Lu H, Goodell V, Disis M L (2008) Humoral immunity directed against tumor-associated antigens as potential biomarkers for the early diagnosis of cancer. J Proteome Res 7:1388-1394.

Lubin R, Schlichtholz B, Bengoufa D, Zalcman G, Tredaniel J, Hirsch A, de Fromentel C C, Preudhomme C, Fenaux P, Fournier G, Mangin P, Laurent-Puig P, Pelletier G, Schlumberger M, Desgrandchamps F, Le Duc A, Peyrat J P, Janin N, Bressac B, Soussi T. (1993) Analysis of p53 antibodies in patients with various cancers define B-cell epitopes of human p53: distribution on primary structure and exposure on protein surface. Cancer Res 53:5872-5876.

Mintz P J, Kim J, Do K A, Wang X, Zinner R G, Cristofanilli M, Arap M A, Hong W K, Troncoso P, Logothetis C J, Pasqualini R, Arap W (2003) Fingerprinting the circulating repertoire of antibodies from cancer patients. Nat Biotechnol 21:57-63.

Pereira-Faca S R, Kuick R, Purays E, Zhang Q, Krasnoselsky A L, Phanstiel D, Qiu J, Misek D E, Hinderer R, Tammemagi M, Landi M T, Caporaso N, Pfeiffer R, Edelstein C, Goodman G, Barnett M, Thornquist M, Brenner D, Hanash S M (2007) Identification of 14-3-3 theta as an antigen that induces a humoral response in lung cancer. Cancer Res 67:12000-12006.

Ramachandran N, Raphael J V, Hainsworth E, Demirkan G, Fuentes M G, Rolfs A, Hu Y, Labaer J (2008) Next-generation high-density self-assembling functional protein arrays. Nat Methods 5:535-538.

Rasmussen N, Ditzel H J (2009) Identification of the specificity of isolated phage display single-chain antibodies using yeast two-hybrid screens. Methods Mol Biol 562: 165-176.

Rauschert N, Brandlein S, Holzinger E, Hensel F, Muller-Hermelink H K, Vollmers H P (2008) A new tumor-specific variant of GRP78 as target for antibody-based therapy. Lab Invest 88:375-386.

Reis C A, Sorensen T, Mandel U, David L, Mirgorodskaya E, Roepstorff P, Kihlberg J, Hansen J E, Clausen H (1998) Development and characterization of an antibody directed to an alpha-N-acetyl-D-galactosamine glycosylated MUC2 peptide. Glycoconj J 15:51-62.

Sabbatini P J, Ragupathi G, Hood C, Aghajanian C A, Juretzka M, Iasonos A, Hensley M L, Spassova M K, Ouerfelli O, Spriggs D R, Tew W P, Konner J, Clausen H, Abu R N, Dansihefsky S J, Livingston P O (2007) Pilot study of a heptavalent vaccine-keyhole limpet hemocyanin conjugate plus QS21 in patients with epithelial ovarian, fallopian tube, or peritoneal cancer. Clin Cancer Res 13:4170-4177.

Sahin U, Tureci O, Schmitt H, Cochlovius B, Johannes T, Schmits R, Stenner F, Luo G, Schobert I, Pfreundschuh M (1995) Human neoplasms elicit multiple specific immune responses in the autologous host. Proc Natl Acad Sci USA 92:11810-11813.

Schietinger A, Philip M, Yoshida B A, Azadi P, Liu H, Meredith S C, Schreiber H (2006) A mutant chaperone converts a wild-type protein into a tumor-specific antigen. Science 314:304-308.

Snijdewint F G M, Mensdorff-Pouilly S, Karuntu-Wanamarta A H, Verstraeten A A, Zanten-Przybysz I, Hummel P, Nijman H W, Kenemans P, Hilgers J (1999) Cellular and humoral immune responses to MUC1 mucin and tandem-repeat peptides in ovarian cancer patients and controls. Cancer Immunology Immunotherapy 48:47-55.

Sorensen A L, Reis C A, Tarp M A, Mandel U, Ramachandran K, Sankaranarayanan V, Schwientek T, Graham R, Taylor-Papadimitriou J, Hollingsworth M A, Burchell J, Clausen H (2006) Chemoenzymatically synthesized multimeric Tn/STn MUC1 glycopeptides elicit cancer-specific anti-MUC1 antibody responses and override tolerance. Glycobiology 16:96-107.

Springer G F (1984) T and Tn, General Carcinoma Auto-Antigens. Science 224:1198-1206.

Springer G F, Tegtmeyer H (1980) On the origin of anti-Thomsen-Friedenreich (T) antibodies. Naturwissenschaften 67:317-318.

Stockert E, Jager E, Chen Y T, Scanlan M J, Gout I, Karbach J, Arand M, Knuth A, Old L J (1998) A survey of the humoral immune response of cancer patients to a panel of human tumor antigens. J Exp Med 187:1349-1354.

Takeuchi H, Kato K, Denda-Nagai K, Hanisch F G, Clausen H, Irimura T (2002) The epitope recognized by the unique anti-MUC1 monoclonal antibody MY.1E12 involves sialyl alpha 2-3galactosyl beta 1-3N-acetylgalactosaminide linked to a distinct threonine residue in the MUC1 tandem repeat. Journal of Immunological Methods 270:199-209.

Tarp M A, Clausen H (2008) Mucin-type O-glycosylation and its potential use in drug and vaccine development. Biochim Biophys Acta 1780:546-563.

Tarp M A, Sorensen A L, Mandel U, Paulsen H, Burchell J, Taylor-Papadimitriou J, Clausen H (2007) Identification of a novel cancer-specific immunodominant glycopeptide epitope in the MUC1 tandem repeat. Glycobiology 17:197-209.

Vollmers H P, Brandlein S (2009) Natural antibodies and cancer. N Biotechnol 25:294-298.

White T, Bennett E P, Takio K, Sorensen T, Bonding N, Clausen H (1995) Purification and cDNA cloning of a human UDP-N-acetyl-alpha-D-galactosamine:polypeptide N-acetylgalactosaminyltransferase. J Biol Chem 270: 24156-24165.

---

What is claimed is:

1. A panel of glycopeptides comprising at least a plurality of isolated glycopeptides, each isolated glycopeptide comprising a glycopeptide epitope, said epitope having been previously determined (i) to be selectively recognized by a subset of antibodies in sera from cancer patients, which subset recognizes neither (a) the corresponding naked peptides of said panel when not glycosylated; nor (b) the corresponding glycan when not bound to said peptide; and (ii) not to be recognized by antibodies in control sera, said plurality comprising at least 8 isolated glycopeptides, wherein said plurality comprises isolated glycopeptides comprising amino acid sequences of SEQ ID NOs: 86, 109, 116, 132, 134, 135, 145, and 146, wherein said glycopeptides are immobilized on said panel.

2. The panel of glycopeptides of claim 1, wherein the plurality of isolated glycopeptides comprises SHHSDESDELVTDFPTDLPA (SEQ ID NO: 15); TPTPKEKPEAGTYSVNNGND (SEQ ID NO: 36); SESFPHPGFNMSLLENHTRQ (SEQ ID NO: 49); LAKMYYSAVEPTKDIFTGLI (SEQ ID NO: 86); TDCGGPKDHPLTCDDPRFQA (SEQ ID NO: 109); PGTSTTPSQPNSAGVQDTEM (SEQ ID NO: 116); TKTDASSTHHSTVPPLTSSN (SEQ ID NO: 132); HDVETQFNQYKTEAASRYNL (SEQ ID NO: 134); ASRYNLTISDVSVSDVPFPF (SEQ ID NO: 135); VPVTRPALGSTTPPAHDVTS (SEQ ID NO: 145); and SLASQATDTFSTVPPTPPSI (SEQ ID NO: 146).

3. The panel of glycopeptides of claim 1, wherein the plurality comprises at least 8 and up to 30 isolated glycopeptides, wherein the plurality comprises isolated glycopeptides having amino acid sequences SEQ ID NOs: 86, 109, 116, 132, 134, 135, 145, and 146.

* * * * *